US008101576B2

(12) United States Patent
Bloom

(10) Patent No.: US 8,101,576 B2
(45) Date of Patent: *Jan. 24, 2012

(54) COMPOUNDS AND THEIR EFFECTS ON FEEDING BEHAVIOUR

(75) Inventor: Stephen Robert Bloom, Hampstead (GB)

(73) Assignee: Imperial Innovations Limited (GB)

( * ) Notice: Subject to any disclaimer, the term of this patent is extended or adjusted under 35 U.S.C. 154(b) by 904 days.

This patent is subject to a terminal disclaimer.

(21) Appl. No.: 11/956,266

(22) Filed: Dec. 13, 2007

(65) Prior Publication Data

US 2009/0181885 A1    Jul. 16, 2009

(30) Foreign Application Priority Data

Dec. 13, 2006 (GB) ................... 0624868.6
Dec. 21, 2006 (GB) ................... 0625667.1
Jan. 17, 2007 (GB) ................... 0700897.2

(51) Int. Cl.
*A61K 38/16* (2006.01)
*A61K 31/00* (2006.01)

(52) U.S. Cl. ...... 514/21.3; 530/324; 514/4.9; 424/78.01

(58) Field of Classification Search ........................ None
See application file for complete search history.

(56) References Cited

U.S. PATENT DOCUMENTS

| | | | |
|---|---|---|---|
| 3,773,919 A | 11/1973 | Boswell et al. |
| 4,002,531 A | 1/1977 | Royer |
| 4,175,122 A | 11/1979 | Lazarus |
| 4,179,337 A | 12/1979 | Davis |
| 4,220,653 A | 9/1980 | Vivino |
| 4,223,017 A | 9/1980 | Lazarus |
| 4,355,025 A | 10/1982 | Lazarus |
| 4,485,045 A | 11/1984 | Regen |
| 4,544,545 A | 10/1985 | Ryan et al. |
| 4,619,794 A | 10/1986 | Hauser |
| 4,698,327 A | 10/1987 | Nagarajan |
| 4,701,441 A | 10/1987 | Kalra |
| 4,829,076 A | 5/1989 | Szilagyi et al. |
| 5,021,234 A | 6/1991 | Ehrenfeld |
| 5,026,685 A | 6/1991 | Boublik et al. |
| 5,122,614 A | 6/1992 | Zalipsky |
| 5,284,839 A | 2/1994 | Siren et al. |
| 5,349,052 A | 9/1994 | Delgado et al. |
| 5,428,128 A | 6/1995 | Mensi-Fattohi et al. |
| 5,432,156 A | 7/1995 | Matsuno |
| 5,512,549 A | 4/1996 | Chen et al. |
| 5,574,010 A | 11/1996 | McFadden |
| 5,604,203 A | 2/1997 | Balasubramaniam |
| 5,635,503 A | 6/1997 | Poindexter et al. |
| 5,643,575 A | 7/1997 | Martinez et al. |
| 5,696,093 A | 12/1997 | Tseng et al. |
| 5,700,486 A | 12/1997 | Canal et al. |
| 5,728,396 A | 3/1998 | Peery et al. |
| 5,858,975 A | 1/1999 | Yano |
| 5,880,131 A | 3/1999 | Greenwald et al. |
| 5,889,016 A | 3/1999 | Bruce et al. |
| 5,912,227 A | 6/1999 | Croom et al. |
| 5,919,901 A | 7/1999 | Hu et al. |
| 5,936,092 A | 8/1999 | Shen |
| 5,939,380 A | 8/1999 | Wang |
| 5,965,392 A | 10/1999 | Hu et al. |
| 5,989,920 A | 11/1999 | Gerald et al. |
| 5,993,414 A | 11/1999 | Haller |
| 6,001,836 A | 12/1999 | Poindexter et al. |
| 6,001,970 A | 12/1999 | Cascieri et al. |
| 6,046,167 A | 4/2000 | Balsurbramaniam |
| 6,048,900 A | 4/2000 | Connell et al. |
| 6,093,692 A | 7/2000 | Shen |
| 6,127,355 A | 10/2000 | Greenwald et al. |
| 6,140,354 A | 10/2000 | Dax et al. |
| 6,191,102 B1 | 2/2001 | Dimarchi et al. |
| 6,201,025 B1 | 3/2001 | Dax et al. |
| 6,218,408 B1 | 4/2001 | Marzabadi et al. |
| 6,225,330 B1 | 5/2001 | Marzabadi et al. |
| 6,225,445 B1 | 5/2001 | Shen et al. |
| 6,268,343 B1 | 7/2001 | Knudsen |
| 6,316,203 B1 | 11/2001 | Gerald et al. |
| 6,340,683 B1 | 1/2002 | Marzabadi et al. |
| 6,348,472 B1 | 2/2002 | Poindexter et al. |
| 6,355,478 B1 | 3/2002 | Baez et al. |
| 6,372,743 B1 | 4/2002 | Darrow et al. |
| 6,380,224 B1 | 4/2002 | Dax et al. |
| 6,391,877 B1 | 5/2002 | Islam et al. |
| 6,391,881 B2 | 5/2002 | Sit |
| 6,399,631 B1 | 6/2002 | Elliott et al. |
| 6,407,120 B1 | 6/2002 | Carpino et al. |
| 6,410,707 B2 | 6/2002 | Wagner |
| 6,410,792 B1 | 6/2002 | Connell et al. |
| 6,420,532 B1 | 7/2002 | Gerald et al. |

(Continued)

FOREIGN PATENT DOCUMENTS

CA    2431800 A1    6/2002

(Continued)

OTHER PUBLICATIONS

U.S. Appl. No. 60/256,216, filed Dec. 14, 2000, Pittner, et al.
U.S. Appl. No. 60/324,406, filed Sep. 24, 2001, Cowley, et al.
"Clinical Guidelines on the Identification, Evaluation, and treatment of Overweight and Obesity in Adults-The Evidence Report", National Institutes of health, Obesity Research, 6(Suppl2):51S-209S (1998).
"Oxyntomodulin" Internet Document http://www.glucagon.com/oxyntomodulin.htm> Mar. 3, 2001 2 pages, accessed Aug. 30, 2006.
"The Wonders of Weight Loss", American Fitness, Jan./Feb. (2006) p. 18.
Adrian, "Distribution and postprandial release of procine peptide YY", J. Endocr., 113:11 (1987).
Adrian, "Effect of Peptide YY on Gastric, Pancreatic, and Biliary Function in Humans", Gastroenterology, 89:494 (1985).
Adrian, "Elevated Plasma Peptide YY in Human Neonates and Infants," Pediatric Research, 20(12):1225-1227 (1986).
Adrian, "Human distribution and release of a putative new gut hormone, peptide YY", Gastroenterology, 89:1070-1077 (1985).

(Continued)

*Primary Examiner* — Cecilia J Tsang
*Assistant Examiner* — Satyanarayana Gudibande
(74) *Attorney, Agent, or Firm* — Lando & Anastasi LLP

(57) ABSTRACT

The invention features peptides for the treatment or prevention of obesity, diabetes or co-morbidities of obesity; for reduction of appetite, food intake, calorie intake, body weight, or body weight gain; and for increase of energy expenditure in a subject.

41 Claims, 27 Drawing Sheets

U.S. PATENT DOCUMENTS

Figure 2:
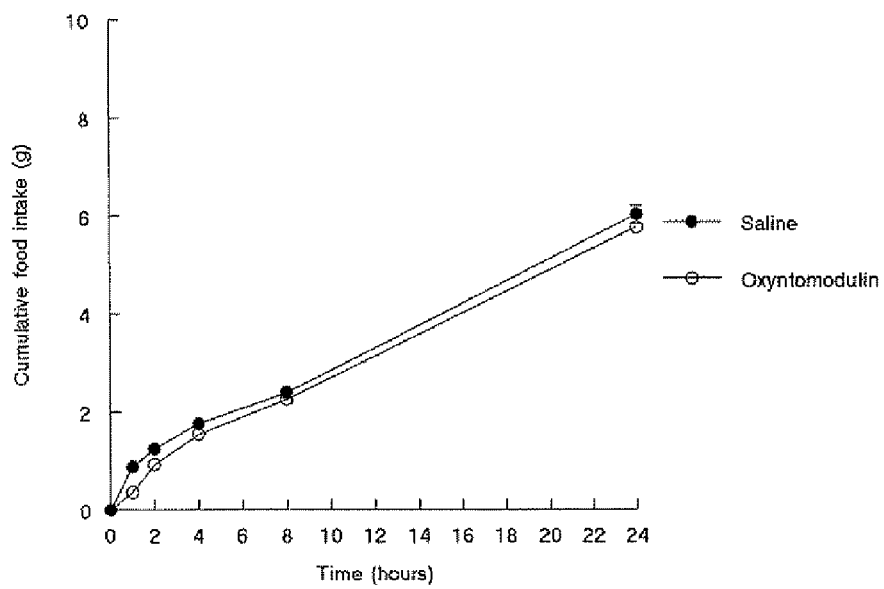

| | | | |
|---|---|---|---|
| 6,432,960 B2 | 8/2002 | Sit et al. |
| 6,436,091 B1 | 8/2002 | Harper |
| 6,444,675 B2 | 9/2002 | Sit |
| 6,447,743 B1 | 9/2002 | Devic |
| 6,447,753 B2 | 9/2002 | Edwards et al. |
| 6,458,924 B2 | 10/2002 | Knudsen |
| 6,583,111 B1 | 6/2003 | DiMarchi et al. |
| 6,586,403 B1 | 7/2003 | Mathison |
| 6,608,098 B1 | 8/2003 | Nagase et al. |
| 6,620,910 B1 | 9/2003 | Calas et al. |
| 6,645,774 B1 | 11/2003 | Gerald et al. |
| 6,667,319 B2 | 12/2003 | Stamford et al. |
| 6,699,891 B1 | 3/2004 | Kawanishi et al. |
| 6,890,898 B2 | 5/2005 | Bachovchin et al. |
| 6,956,026 B2 | 10/2005 | Beeley et al. |
| 7,078,381 B2 | 7/2006 | Bachovchin et al. |
| 7,157,429 B1 | 1/2007 | Bachovchin et al. |
| 7,166,575 B2 | 1/2007 | Quay |
| 7,265,125 B2 | 9/2007 | Breu et al. |
| 7,396,809 B1 | 7/2008 | Lu et al. |
| 7,459,432 B2 | 12/2008 | Cowley et al. |
| 2001/0011071 A1 | 8/2001 | Knudsen |
| 2001/0046956 A1 | 11/2001 | Hadcock |
| 2002/0141985 A1 | 10/2002 | Pittner et al. |
| 2002/0156010 A1 | 10/2002 | Lustig |
| 2004/0018975 A1 | 1/2004 | DiMarchi et al. |
| 2005/0070469 A1 | 3/2005 | Bloom et al. |
| 2005/0176630 A1 | 8/2005 | Cowley et al. |
| 2005/0176643 A1 | 8/2005 | Bridon et al. |
| 2006/0014678 A1 | 1/2006 | Cowley et al. |
| 2006/0171920 A1 | 8/2006 | Shecther |
| 2006/0189522 A1 | 8/2006 | Bloom et al. |
| 2008/0064636 A1 | 3/2008 | Bloom et al. |
| 2009/0181885 A1 | 7/2009 | Bloom |
| 2009/0209461 A1 | 8/2009 | Cowley et al. |

FOREIGN PATENT DOCUMENTS

| | | |
|---|---|---|
| CN | 1490333 A | 4/2004 |
| DE | 3218121 A1 | 11/1983 |
| EP | 0036676 A1 | 9/1981 |
| EP | 0052322 A2 | 5/1982 |
| EP | 0058481 A1 | 8/1982 |
| EP | 0088046 A2 | 9/1983 |
| EP | 0102324 A2 | 3/1984 |
| EP | 0133988 A2 | 3/1985 |
| EP | 0142641 A2 | 5/1985 |
| EP | 0143949 A1 | 6/1985 |
| EP | 0267050 A2 | 5/1988 |
| EP | 0401384 A1 | 12/1990 |
| EP | 0619332 A1 | 10/1994 |
| EP | 0708179 A2 | 4/1996 |
| EP | 0795562 A1 | 9/1997 |
| EP | 0920864 A1 | 6/1999 |
| EP | 0955314 A2 | 11/1999 |
| EP | 1499277 A2 | 1/2005 |
| JP | 60-007934 A | 1/1985 |
| JP | 11-228447 A | 8/1999 |
| JP | 2001-011095 A | 1/2001 |
| WO | 80/01882 A1 | 9/1980 |
| WO | 93/09227 A1 | 5/1993 |
| WO | 93/19175 A1 | 9/1993 |
| WO | 94/27431 A1 | 10/1994 |
| WO | 95/06058 A1 | 3/1995 |
| WO | 96/22783 A1 | 8/1996 |
| WO | 97/37998 A2 | 10/1997 |
| WO | 97/46579 A1 | 12/1997 |
| WO | 98/20885 A1 | 5/1998 |
| WO | 98/20895 A1 | 5/1998 |
| WO | 98/30231 | 7/1998 |
| WO | 98/32466 A1 | 7/1998 |
| WO | 99/39291 | 8/1999 |
| WO | 99/43707 A1 | 9/1999 |
| WO | 00/34236 A1 | 6/2000 |
| WO | 00/42026 A1 | 7/2000 |
| WO | 00/47219 A2 | 8/2000 |
| WO | 00/59887 A1 | 10/2000 |
| WO | 00/68197 A1 | 11/2000 |
| WO | 00/78333 A2 | 12/2000 |
| WO | 01/04156 A1 | 1/2001 |
| WO | 01/14368 A1 | 3/2001 |
| WO | 01/14386 A1 | 3/2001 |
| WO | 01/35988 A1 | 5/2001 |
| WO | 01/51078 A1 | 7/2001 |
| WO | 01/66135 A1 | 9/2001 |
| WO | 01/68699 A2 | 9/2001 |
| WO | 01/76631 A2 | 10/2001 |
| WO | 01/087335 A2 | 11/2001 |
| WO | 01/89554 A2 | 11/2001 |
| WO | 02/03978 A2 | 1/2002 |
| WO | 02/47712 A2 | 6/2002 |
| WO | 02/066479 A1 | 8/2002 |
| WO | 02/067918 A1 | 9/2002 |
| WO | 03/022304 A1 | 3/2003 |
| WO | 03026591 A2 | 4/2003 |
| WO | 03057235 A2 | 7/2003 |
| WO | 2004/062685 A2 | 7/2004 |
| WO | 2005/035761 A1 | 4/2005 |
| WO | 2005/118642 A2 | 12/2005 |
| WO | 2006/082517 A1 | 8/2006 |
| WO | 2006/095166 A1 | 9/2006 |
| WO | 2006134340 A2 | 12/2006 |
| WO | 2007/056362 A2 | 5/2007 |
| WO | 2007/100535 A2 | 9/2007 |
| WO | 2007/146038 A2 | 12/2007 |
| WO | 2008003947 A1 | 1/2008 |
| WO | 2008071972 A1 | 6/2008 |

OTHER PUBLICATIONS

Adrian, "Peptide YY Abnormalities in Gastrointestinal Diseases", Gastroenterology, 90:379 (1986).

Adrian, "Plasma Peptide YY (PYY) in Dumping Syndrome", Digestive Diseases &Sciences, 30(12):1145 (1985).

Adrian, "Release of peptide YY (PYY) after resection of small bowel, colon, or pancreas in man," Surgery, 101 (6),715 (1987).

Allen, "Effects of Peptide YY and Neuropeptide Y on Gastric Emptying in Man", Digestion, 30:255 (1984).

Allen, "Radioimmunoassay of neuropeptide Y", Regulatory Peptides, 8:61-70 (1984).

Allen, "Two novel related peptides, neuropeptide Y (NPY) and Peptide YY (PYY) inhibit the contraction of the electrically stimulated mouse vas deferens", Neuropeptides, 3:71-77 (1982).

Andersen, "Cimetidine and obesity: Conflicting evidence", Intl. J. Obesity 23:550 (1999).

Asakawa, "Mouse pancreatic polypeptide modulates food intake, while not influencing anxiety in mice", Peptides, 20:1445 (1999).

Assuncao, "Weight gain management in patients with schizophrenia during treatment with olanzapine in association with nizalidine", Rev. Bras. Psiquiatr 28(4):270-276 (2006).

Aubuchowski, "Cancer therapy with chemically modified enzymes. I. Antitumor properties of polyethylene glycol-asparaginase conjugates", Cancer Biochem. Biophys., 7:175-86 (1984).

Bado, "Neurotensin and oxyntomodulin-(30-37) potentiate PYY regulation of gastric acid and somatostatin secretions", Am. J. Physiol., 265:G113-7 (1993).

Bagger, "Nasal bioavailability of peptide T in rabbits: Absorption enhancement by sodium glycocholate and glycofurol" Eur. J. Pharm. Sci., 14:69-74 (2001).

Bagnol, "Anatomy of an Endogenous Antagonist: Relationship between Agouti-Related Protein and Proopiomelanocortin in Brain", J. Neurosci. (Online), 19:1-7; RC26 (1999).

Balasubramaniam, "Syntheses and receptor affinities of partial sequences of peptide YY (PYY)", Peptide Research, 1(1):32-5 (1998).

Barlow and Dietz, "Obesity evaluation and treatment: Expert Committee recommendations", Pediatrics, 102 (3):1-11 (1998).

Barrachina, "Leptin-induced decrease in food intake is not associated with changes in gastric emptying in lean mice", Am. J. Physiol., 272:1007-11 (1997).

Barsh, Genetics of body-weight regulation,—Nature, 404, 644 (2000).

Batterham, "Gut hormone PYY3-36 physiologically inhibits food intake", Nature, 418:650-4 (2002).

Bays, "Current and investigational antiobesity agents and obesity therapeutic treatment targets", Obes Res, 12 (8):1197-1211 (2004).
Beck-Sickinger and Jung, "Structure-activity relationships of neuropeptide Y analogues with respect to Y1 and Y2 receptors", Biopolymers, 37:123-142 (1995).
Beer, "The effect of a 72-h fast on plasma levels of pituitary, adrenal, thyroid, pancreatic and gastrointestinal hormones in healthy men and women," J. Endocr., 120;337 (1989).
Berglund, "Binding Properties of Three Neuropeptide Y Receptor Subtypes from Zebrafish: Comparison with Mammalian Y1 Receptors", Biochem. Pharmacol., 60:1815-22, (2000).
Bowie, "Deciphering the message in protein sequences: tolerance to amino acid substitutions", Science, 247:1306-1310 (1990).
Broberger, "Subtypes Y1 and Y2 of the neuropeptlde Y receptor are respectively expressed in pro-opiomelanocortin-and neuropeptide-Y-containing neurons of the rat hypothalamic arcuate nucleus", Neuroendocrinology, 66:393-408 (1997).
Buchwald, "Long-term, continuous intravenous heparin administration by an implantable infusion pump in ambulatory patients with recurrent venous thrombosis", Surgery, 88:507-516 (1980).
Buse, "Effects of exenatide (exendin-4) on glycemic control over 30 weeks in sulfonylurea-treated patients with type 2 diabetes", Diabetes Care, 27(11):2628-2635 (2004).
Butler, "A Unique Metabolic Syndrome Causes Obesity in the Melanocortin-3 Receptor-Deficient Mouse", Endocrinology, 141:3518 (2000).
Butler, "Melanocortin-4 receptor is required for acute homeostatic responses to increased dietary fat", Nature Neuroscience, 4:605-611 (2001).
CAA27627 (gi762941): "unnamed protein product [*Homo sapiens*]", NCBI Record dated Dec. 3, 2009, (Database Medline [online], Bethesda, MD, USA: US National Library of Medicine (NLM), retrieved from internet using <URL:http://www.ncbi.nlm.nih.gov/protein/762941, NCBI Accession No. CAA27627 (gi762941).
Cabrele, "Molecular characterization of the ligand-receptor interaction of the neuropeptide Y family", J. Pept. Sci, 6:97-122 (2000).
Calam, "Regional Differences in Concentrations of Regulatory Peptides in Human Colon Mucosal Biopsy", Digestive Diseases & Sciences, 34(8):1193 (1989).
Caliceti, "Biopharmaceutical properties of uricase conjugated to neutral and amphiphilic polymers", Bioconjug. Chem., 10:638-46 (1999).
Campbell, "Oxygen-dependent K+ influxes in Mg2+-clamped equine red blood cells", J. Physiol. (Lond.) 515.2, 431-437 (1999).
Campfield, "Recombinant Mouse OB Protein: Evidence for a Peripheral Signal Linking Adiposity and Central Neural Networks", Science, 269:546 (1995).
Chelikani, "Intravenous infusion of peptide YY(3-36) potently inhibits food intake in rats", Endocrinology, 146 (2):879-88 (2005).
Clapham, "Anti-obesity drugs: a critical review of current therapies and future opportunities", Pharmacol.. & Ther., 89:81-121 (2001).
Cohen, Oxyntomodulin suppresses appetite and reduces food intake in humans, J. Clin, Endocrinol. & Metab., 88 (10):4696-4701 (2003).
Comuzzie, "A major quantitative trait locus determining serum leptin levels and fat mass is located on human chromosome 2", Nature Genetics, 15:273 (1997).
Cone, "The Central Melanocortin System and Energy Homeostasis", TEM, 10(6); 211-216 (1999).
Cowley, "Integration of NPY, AGRP, and Melanocortin Signals in the Hypothalamic Paraventricular Nucleus: Evidence of a Cellular Basis for the Adipostat," Neuron, 24, 155 (1999).
Cowley, "Leptin activates anorexigenic POMC neurons through a neural network in the arcuate nucleus", Nature, 411:480-484 (2001).
Cox and Randich, "Enhancement of feeding suppression by PYY3-36 in rats with area postrema ablations", Peptides, 25:985-9 (2004).
Csiffart, "Neuropeptide Y Innerveration of ACTH-immunoreactive neurons in the arcuate nucleus of rats: a correlated light and electron microscopic double immunolabeling study", Brain Research, 506:215-222 (1990).
Hakansson, "leptin receptor immunoreactivity in chemically defined target neurons of the hypothalamus", J. Neurosci., 18:559-72 (1998).

Hammer, "Pituitary-Specific and Hormonally Regulated Gene Expression Directed by the Rat Proopiomelanocortin Promoter in Transgenic Mice," Mol. Endocrin., 4(11):1689 (1990).
Harding, "Identification and Characterization of the Emetic Effects of Peptide YY", Peptides, 10:21 (1989).
Haynes, "Interactions Between the Melanocortin System and leptin in Control of Sympathetic Nerve Traffic", Hypertension, 33[part II], 542 (1999).
Haynes, "Receptor-mediated Regional Sympathetic Nerve Activation by Leptin", J. Clin. Invest., 100:270 (1997).
Heisler, "Activation of Central Melanocortin Pathways by Fenfluramine", Science, 297:609 (2002).
Hoffman, "c-Fos and Related Immediate Early Gene Products as Markers of Activity in Neuroendocrine Systems", Front. Neuroendocrinol., 14:173 (1993).
Holst, "Enteroglucagon", Ann. Rev. Physiol., 59:257-271 (1997).
Holz and Habener, "Black widow spider alpha-latrotoxin: a presynaptic neurotoxin that shares structural homology with the glucagon-like peptide-1 family of insulin secretagogic hormones", Comp. Biochem. Physiol., Part B, 121:177-184 (1998).
Horvath, "Gabaergic and Catecholaminergic Innervation of Mediobasal Hypothalamic b-Endorphin Cells Projecting to the Medial Preoptic Area", Neuroscience, 51:391 (1992).
Horvath, "Heterogeneity in the neuropeptlde Y-containing neurons of the rat arcuate nucleus: GABAergic and non-GABAergic subpopulations", Brain Res., 756, 283-286 (1997).
Hwang, "Hepatic uptake and degradation of unilamellar sphingomyelin/cholesterol liposomes: A kinetic study", Proc. Natl. Acad. Sci. U.S.A., 77:4030-4034 (1980).
International Preliminary Examination Report dated Jan. 28, 2005 from International Application No. PCT/US02/31944.
Iyengar, "Characterization of Neuropeptide Y-Induced Feeding in Mice: Do Y1-Y6 Receptor Subtypes Mediate Feeding?" J. of Pharmacology and Experimental Therapeutics, 289(2),1031 (1999).
Jequier, "Energy, obesity, and body weight standards", Am. J. Clin. Nutr., 45:1035-47 (1987).
Kalra, "Interacting appetite-regulating pathways in the hypothalamic regulation of body weight", Endocr. Rev., 20:68-100 (1999).
Kanatani, "L-152,804: Orally active and selective neuropeptide Y Y5 receptor antagonist", Biochem. Biophys. Res. Commun., 272:169-73 (2000).
Kawana, "Nasal immunization of mice with peptide having a cross-neutralization epitope on minor capsid protein L2 of human papillomavirus type 16 elicit systemic and mucosal antibodies" Vaccine 19:1496-1502 (2001).
Keire, et al., "Primary structures of PYY, [Pro34]PYY, and PYY-(3-36) confer different conformations and receptor selectivity," Am. J. Physiol. Gastrointest. Liver Physiol., 279, G126 (2000).
Kelly, "Opioids Hyperpolarize b-Endorphin Neurons via m-Receptor Activation of a Potassium Conductance", Neuroendocrinology, 52:268 (1990).
Kenchaiah, "Obesity and the risk of heart failure", N. Engl. J. Med., 347(5):305-13 (2002).
Kim, "Hypothalamic localization of the feeding effect of agouti-related peptide and alpha-melanocyte-stimulating hormone", Diabetes, 49:177-182 (2000).
Kim, "The central melanocortin system affects the hypothalamopituitary thyroid axis and may mediate the effect of leptin", J. Clin. Invest., 105:1005-1011 (2000).
Kimmel, "Isolation and characterization of chicken insulin", Endocrinology, 83:1323-30 (1968).
King, "Regulation of neuropeptlde Y release by neuropeptide Y receptor ligands calcium channel antagonists in hypothalamic slices", J. Neurochem., 73:641-6 (1999).
Kirby, "Defining Structural Requirements for Neuropeptide Y Receptors Using Truncated and Conformationally Restricted Analogues", J. Med. Chem., 36:385-393 (1993).
Kirby, "Neuropeptide Y: Y1 and Y2 affinities of the complete series of analogues with single D-residue substitutions", J. Med. Chem., 36:3802-3808 (1993).
Kirby, "Y1 and Y2 receptor selective neuropeptide Y analogues: Evidence for a Y1 receptor subclass", J. Med. Chem., 38:4579-4586 (1993).

Kopelman, "Obesity as a medical problem", Nature, 404:635-43 (2000).

Kreymann, "Developmental Patterns of Glucagon—Like Peptide-I-(7-36) Amide and Peptide-YY in Rat Pancreas and Gut", Endocrinology, 129:1001 (1991).

Kreymann, "Glucagon-like peptide-1 7-36: a physiological incretin in man", Lancet, 1300-1304 (1987).

Krude, "Implications of Proopiomelanocortin (POMC) Mutations in Humans: The POMC Deficiency Syndrome", Trends Endocrinol. Metab., 11(1):15 (2000).

Krude, "Severe early-onset obesity, adrenal insufficiency and red hair pigmentation caused by POMC mutations in humans", Nature Genetics, 19:155 (1998).

Langer, "Biocompatibility of polymeric delivery systems for macromolecules", J. Biomed. Mater. Res.,15:267-277 (1981).

Langer, "Controlled release of macromolecules", Chem. Tech., 12:98-105 (1982).

Langer, "New methods of drug delivery", Science, 249:1527-1533 (1990).

Leban, "Novel modified carboxy terminal fragments of neuropeptlde Y with high affinity for Y2-type receptors and potent functional antagonism at a Y1-type receptor", J. Med. Chem., 38:1150-57 (1995).

Leger, "Identification of CJC-1131-Albumin Bioconjugate as a Stable and Bioactive GLP-1(7-36) Analog", Bioorganic & Medicinal Chemistry Letters, Oxford, GB, 14 (2004) 4395-4398.

Liu, "DNA elements with AT-rich core sequences direct pituitary cell-specific expression of the pro-opiomelanocortin gene in transgenic mice", Biochem. J., 312, 827-832 (1995).

Lloyd, "Inhibitory effect of PYY on vagally stimulated acid secretion is mediated predominantly by Y1 receptors", American Journal of Physiology, 270(1):123-127 (Jan. 1996).

Liu, "Identification of DNA Elements Cooperatively Activating Proopiomelanocortin Gene Expression in the Pituitary Glands of Transgenic Mice", Mol & Cell Biol., 12(9):3978-3990 (1992).

Liu, "Synthetic peptide YY analog binds to a cell membrane receptor and delivers fluorescent dye to pancreatic cancer cells", J. Gastrointest. Surg., 5(2):147-52 (2001).

Low, et al., "Post-translational Processing of Proopiomelanocortin (pOMC) in Mouse Pituitary Melanotroph Tumors Induced by a POMC-Simian Virus 40 Large T Antigen Transgene," J. Biol. Chem 268 (33), 24967-24975 (1993).

Lundberg and Modin, "Inhibition of sympathetic vasoconstriction in pigs in vivo by the neuropeptide Y-Y1 receptor antagonist BIBP 3226", Br. J. Pharmacol., 116(7):2971-82 (1995).

Lyznicki, "Obesity: Assessment and Management in Primary Care", Amer. Family Phys., 63(11):2185-2196 (2001).

Malaisse-Lagae, "Pancreatic polypeptide: A possible role in the regulation of food intake in the mouse. Hypothesis", Experientia, 33(7):915 (1977).

Malik, "Polyethylene glycol (PEG)-modified granulocyte-macrophage colony-stimulating factor (GM-CSF) with conserved biological activity", Exp. Hematol., 20(8):1028-35 (1992).

Malmstrom, "Existence of both neuropeptide Y, Y1 and Y2 receptors in pig spleen evidence using subtype-selective antagonists in vivo", Life Sci., 69:1999-2005 (2001).

Malmstrom, "Pharmacology of H 394/84, a dihydropyridine neuropeptide Y Y1 receptor antagonist, in vivo", Eur. J. Pharmacol., 418:95-104 (2001).

Marks, et al., "Role of the Central Melanocortin System in Cachexia", Cancer Research, 61:1432 (2001).

Cummings, "A preprandial rise in plasma ghrelin levels suggest a role in meal initiation in humans", Diabetes, 50:1714-1719 (2001).

Dakin, "Novel Actions of Oxyntomodulin in the Central Nervous System", Dept. of Endocrinology & Metabolism, Imperial College School Medicine, Hammersmith Hospital, Du Cane Road, London. W12 ONN, Journal of Endocrinology, Mar. 2000, vol. 164 Supplement (Abstract #181).

Dakin, "Novel Actions of Oxyntomodulin in the Central Nervous System", Dept. of Endocrinology & Metabolism, Imperial College School Medicine, Hammersmith Hospital, Du Cane Road, London. W12 ONN. UK presented at 19th Joint Meeting of the British Endocrine Societies, with the European Federation of Endocrine Societies, Mar. 13-16, 2000.

Dakin, "Oxyntomodulin inhibits food intake in the rat", Endocrinology, 142:4244-4250 (2001).

Dakin, "Peripheral oxyntomodulin reduces food intake and body weight gain in rats", Endocrinology, 145:2687-2695 (2004).

Dakin, "Repeated ICV administration of oxyntomodulin causes a greater reduction in body weight gain than in pair-fed rats", Am. J. Physiol. Endocrinol. Metab., 283:E1173-E1177(2002).

Delgado, "The uses and properties of PEG-linked proteins", Crit. Rev. Ther. Drug Carrier Syst., 9(3-4):249-304 (1992).

Donckier, "Age-related changes in regulatory peptides in rectal mucosa", Acta Gastro-Enterologica Belgica vol. L Juillet-Aout, 405 (1987).

Doods, "Pharmacological characterization of the selective nonpeptide neuropeptide Y Y1 receptor antagonist BIBP 3226", J. Pharmacol. Exp. Ther., 275(1):136-42 (1995).

Dreborg, "Immunotherapy with monomethoxypolyethylene glycol modified allergens", Crit. Rev. Ther. Drug Carrier Syst 6(4):315-65 (1990).

Dumont, "Characterization of a selective neuropeptide Y/peptide YY Y2 receptor radioligand: [125I]PYY3-36", Society for Neuroscience Abstracts, 19:726 (1993).

Eberlein, "A new molecular form of PYY: structural characterization of human PYY(3-36) and PYY(1-36)", Peptides, 10:797-803 (1989).

Edwards, "Exendin-4 reduces fasting and postprandial glucose and decreases energy intake in healthy volunteers", Am, J, Physiol. Endocrinol . Metab 281: E155-E161 (2001).

Ekblad, "Distribution of pancreatic polypeptide and peptide YY," Peptides, 23:251 (2002).

Elias, "Leptin Differentially Regulates NPY and POMC Neurons Projecting to the Lateral Hypothalamic Area", Neuron, 23:775 (1999).

Eng, "Isolation and characterization of exendin-4, an exendin-3 analogue, from Heloderma suspectum venom. Further evidence for an exendin receptor on dispersed acini from guinea pig pancreas", J. Biol. Chem., 267(11):7402-5 (1992).

English, "Food fails to suppress ghrelin levels in obese humans", J Clin Endocrinol Metab, 87:2984-87 (2002).

Epstein, "Biological activity of liposome-encapsulated murine interferon gamma is mediated by a cell membrane receptor", Proc. Natl. Acad, Sci. U.S.A. 82:3688-3692 (1985).

Examiner Interview Summary Record (PTOL-413) dated Nov. 26, 2008 from U.S. Appl. No. 10/490,776.

ExPasy Proteomics Tools, Compute pl/MW, http://ca.expasy.org/cgi-bin/pi_tool, printed on Apr. 10, 2007.

Fan, "Role of melanocortinergic neurons in feeding and the agouti obesity syndrome," Nature, 385,165 (1997).

Farooqi, "Effects of Recombinant Leptin Therapy in a Child with Congenital Leptin Deficiency", New England J. Med., 341 :879 (1999).

Ferri, "Intramural distribution of regulatory peptides in the sigmoid-recto-anal region of the human gut", Gut, 29,762 (1988).

Fournier, "Conformational and biological studies of neuropeptide Y analogs containing structural alterations", Mol. Pharmacol., 45:93-101 (1994).

Francis, "PEGylation of cytokines and other therapeutic proteins and peptides: the importance of biological optimisation of coupling techniques", Int. J. Hematol., 68:1-18 (1998).

Fried, "Temporal Relationships of Cholecystokinin Release, Pancreatobiliary Secretion, and Gastric Emptying of a Mixed Meal", Gastroenterology, 95:1344 (1988).

Fuebl, et al., "Peptide YY in Diabetes Treated Chronically with an Intestinal Gluosidase Inhibitor," Klinische Wochenschrift, 66985 (1988).

Fuessl, "The effect of a long-acting somatostatin analogue (SMS 201-995) on intermediary metabolism and gut hormones after a test meal in normal subjects", Aliment. Pharmacol. Therap., 1:321 (1987).

Gantz, "Efficacy and safety of intranasal peptide PYY3-36 for weight reduction in obese adults", J Clin Endocrinol & Metabol, 92(5):1754-1757 (2007).

Garrow, "Does cimetidine cause weight loss?", BMJ., 306(6885):1084 (1993).
Gehlert, "Multiple receptors for the pancreatic polypeptide (PP-fold) family: Physiological implications (44263)", Proc. Soc. Exp. Biol. Med., 218:7-22 (1998).
Ghatei, "Fermentable dietary fibre, intestinal microflora and plasma hormones in the rat", Clinical Science, 93:109 (1997).
Ghatei, "Molecular forms of human enteroglucagon in tissue and plasma: plasma responses to nutrient stimuli in health and in disorders of the upper gastrointestinal tract", J. Clin. Endocrinol . Metab.., 57:488-495 (1983).
Glaum, "Leptin, the Obese Gene Product, Rapidly Modulates Synaptic Transmission in the Hypothalamus", Mol. Pharmacol., 50: 230 (1996).
Goodlad, "Does the response of the intestinal epithelium to keratinocyte growth factor vary according to the method of administration?", Regulatory Peptides, 87, 83 (2000).
Goodlad, "Effects of an elemental diet, inert bulk and different types of dietary fibre on the response of the intestinal epithelium to refeeding in the rat and relationship to plasma gastrin, enteroglucagon, and PYY concentrations", Gut, 28:171 (1987).
Goodlad, "Glucagon 1-21 Reduces Intestinal Epithelial Cell Proliferation in Parenterally Fed Rats", Experimental Physiology, 76:943 (1991).
Goodlad, "Insulin and Intestinal Epithelial Cell Proliferation", Experimental Physiology, 78;697 (1993).
Goodlad, "Is Peptide YY Trophic to the Intestinal Epithelium of Parentally Fed Rats?", Digestion, 46(suppl 2):177 (1990).
Goodlad, "Plasma Enteroglucagon, Gastrin and Peptide YY in Conventional and Germ-Free Rats Refed with a Fibre-Free or Fibre-Supplemented Diet", Quarterly Journal of Experimental Physiology, 74:437 (1989).
Goodlad, "Proliferative effects of 'fibre' on the intestinal epithelium: relationship to gastrin, enteroglucagon and PYY", Gut 28(S1):221 (1987).
Graffner, "Effects of Physiological Increases of Plasma Noradrenaline on Gastric Acid Secretion and Gastrointestinal Hormones", Digestive Diseases & Sciences, 32(7):715 (1987).
Grandt, "Characterization of two forms of peptide YY, PYY(1-36) and PYY(3-36), in the rabbit", Peptides, vol. 15, No. 5, 815-820 (1994).
Grandt, "Neuropeptide Y 3-36 is an endogenous ligand selective for Y2 receptors", Regulatory Peptides, 67:33-37 (1996)>.
Grandt, "Two molecular forms of peptide YY (PYY) are abundant in human blood: characterization of a radioimmunoassay recognizing PYY 1-36 and PYY 3-36", Regulatory Peptides, 51:151-159 (1994).
Grieco, "D-Amino Acid Scan of g-Melanocyte-Stimulating Hormone: Importance of Trp8 on Human MC3 Receptor Selectivity", J. Med. Chem., 43:4998 (2000).
Grove, "Neuropeptide Y Y5 receptor protein in the cortical/limbic system and brainstem of the rat: expression on g-aminobutyric acid and corticotropin-releasing hormone neurons", Neuroscience, 100(4):731-740 (2000).
Grundemar, "Ligand binding and functional effects of systematic double D-amino acid residue substituted neuropeptide Y analogs on Y1 and Y2 receptor types", Regulatory Peptides, 62:131-136 (1996).
Hagan, "Peptide YY; a key mediator of orexigenic behavior," Peptides, 23, 377 (2002).
Hager, "A genome-wide scan for human obesity genes reveals a major susceptibility locus on chromosome 10", Nature Genetics, 20:304 (1998).
Search Report dated Sep. 19, 2003 from International Application No. PCT/GB03/00062.
Sefton, "Implantable pumps", CRC Crit. Ref. Biomed. Eng., 14:201 (1987).
Senel, "Drug permeation enhancement via buccal route: possibilities and limitations", J. Control Release, 72 (1-3):133-144 (2001).
Sheikh "Neuropeptide Y and peptide YY: major modulators of gastrointestinal blood flow and function", Am. Physiol.. Society, G701-15 (1991).
Sherwood, "The origin and function of the pituitary adenylate cyclase-activating polypeptide (PACAP)/glucagon superfamily", Endocrine Reviews, 21 (6):619-670 (2000).

Shiraishi, "Leptin Effects on Feeding Related Hypothalamic and Peripheral Neuronal Activities in Normal and Obese Rats", Nutrition, 15;576 (1999).
Sidman, "Controlled release of macromolecules and pharmaceuticals from synthetic polypeptides based on glutamic acid", Biopolymers, 22:547-556 (1983).
Simanowski, "Effects of Acute and Chronic Ethanol Administration on the Gastrointestinal Hormones Gastrin, Enteroglucagon, Pancreatic Glucagon and Peptide YY in the rat", Digestion, 42:167 (1989).
Slugg, "Effect of the m-Opiod Agonist DAMGO on Medial Basal Hypothalamic Neurons in Beta-Endorphin Knockout Mice", Neuroendocrinology, 72:208 (2000).
Small, "Peptide analogue studies of the hypothalamic neuropeptide Y receptor mediating pituitary adrenocorticotrophic hormone release", Proc. Natl. Acad. Sci. U.S.A., 94:11686-91 (1997).
Smilek, "A Single amino acid change in a myelin basic protein peptide confers the capacity to prevent rather than induce experimental autoimmune encephalomyelitis", Proc. Natl. Acad. Sci. U.S.A., 88; 9633-7 (1991).
Soderberg, "Zebrafish genes for neuropeptide Y and peptide YY reveal origin by chromosome duplication from an ancestral gene linked to the homeobox cluster", J. Neurochem., 75:908-18 (2000).
Soll, "Novel analogues of neuropeptide Y with a preference for the Y1-receptor", Eur. J. Biochem., 268:2828-37 (2001).
Spanswick, "Leptin inhibits hypothalamic neurons by activation of ATP-sensitive potassium channels", Nature, 390, 521 (1997).
Spiller, "Further characterisation of the 'ileal brake' reflex in man— effect of ileal infusion of partial digests of fat, protein, and starch on jejunal motility and release of neurotensin, enteroglucagon, and peptide YY", Gut, 29:1042 (1988).
Statement of the Substance of the Interview dated Dec. 26, 2008 from U.S. Appl. No. 10/490,776.
Stoa-Birketvedt, "Cimetidine reduces weight and improves metabolic control in overweight patients with Type 2 diabetes", International Journal of Obesity , 22; 1041-1045 (1998).
Stoa-Birketvedt, "Effect of cimetidine suspension on appetite and weight in overweight subjects", BMJ., 306; 1091-1093 (1993).
Stoa-Birketvedt, "H2-receptor antagonist reduces food intake and weight gain in rats by non-gastric acid secretory mechanisms", Scandinavian Physiological Society, 161; 489-494 (1997).
Tani, "Oxyntomodulin and related peptides control somatostatin secretion in RIN T3 cells" Biochim. . Biophys. Acta 1095:249-254 (1991).
Tarling, "A model of gastric emptying using paracetamol absorption in intensive care patients", Intensive Care Med., 23:256-260 (1997).
Tatemoto, "Isolation and characterization of peptide YY (PYY), a candidate gut hormone that inhibits pancreatic exocrine secretion", Proc. Natl. Acad. Sci., 79:2514-8 (1982).
Tatemoto, "Neuropeptide Y: Complete amino acid sequence of the brain peptide", Proc., Natl. Acad. Sci. U.S.A., 79:5485-9 (1982).
Tsukada, "Functional Analysis of the Cell-Specific Enhancer in the Human Proopiomelanocortin Gene by B-Galactosidase Histochemical Staining", DNA and Cell Biol., 13(7):755 (1994).
Tzotsas, "Use of somatostatin analogues in obesity" Drugs 68(14); 1963-1973 (2008).
Uesaka, "Glucagon-like peptide isolated from the eel intestine: effects on atrial beating", Journal of Experimental Biology, 204:3019-3026 (2001).
Verma, "Human fos gene", Cold Spring Harb. Symp. Quant. Biol., 949-58 (1986).
Voet, D. et al., Biochemistry, 2nd Edition, pp. 235-241 (1995).
Vorobjev, "Oligonucleotide conjugated to linear and branched high molecular weight polyethylene glycol as substrates for RNase H", Nucleosides & Nucleotides, 18(11-12):2745-50 (1999).
Walan and Strom, "Metabolic consequences of reduced gastric acidity", Scand. J. Gastroenterol Suppl., 111:24-30 (1985).
Walker, "Neuropetide Y modulates Neurotransmitter Release and Ca2+ Currents in Rat Sensory Neurons", J. Neuroscience, 8:2438-2446 (1988).
Wang and Hanson, "Parenteral Formulations of Proteins and Peptides: Stability and Stabilizers", Journal of Parenteral Science & Technology, 42:S3-S26 (1988).

Wardlaw, "Obesity as a Neuroendocrine Disease: Lessons to be Learned from Proopiomelanocortin and Melancortin Receptor Mutations in Mice and Men", J. Clin. Endocrin. & Metab., 86(4):1442 (2001).

Wilkosz, "Transdermal Drug Delivery, Part 1: Current Status", In U.S. Pharmacist, retrieved from http//www.uspharmacist.com/index.asp?show=article&page=8_1061.htm on Aug. 29, 2006.

Wolfe and Morton, "Weighing in on bariatric surgery: procedure use, readmission rates, and mortality", JAMA, 294:1960-1963(2005).

Wren, et al., "Ghrelin enhances appetite and increases food intake in humans", J. Clin. Endocrinol. Metab., 86:5992-5 (2001).

Wynne, "Oxyntomodulin increases energy expenditure in addition to decreasing energy intake in overweight and obese humans: a randomised controlled trial", International Journal of Obesity, 30:1729-1736 (2006).

Wynne, "Subcutaneous oxyntomodulin reduces body weight in overweight and obese subjects: a double-blind, randomized, controlled trial", Diabetes, 54:2390-2395 (2005).

Yoshinaga, "Structural requirements of peptide YY for biological activity at enteric sites", Am. Physiol.. Society, G695-G701 (1992).

Young, "Authentic Cell-Specific and Developmentally Regulated Expression of Pro-Opiomelanocortin Genomic Fragments in Hypothalamic and Hindbrain Neurons of Transgenic Mice", J. Neurosci., 18;6631 (1998).

Zhang, "Positional cloning of the mouse obese gene and its human homologue", Nature, 372:425 (1994).

Wynne et al., Oxyntomodulin increases energy expediture in addition to decreasing energy intake in overweight and obses humans: a randomised controlled trial, International Journal of Obesity (2006) 30 (12):1729-1736.

U.S. Appl. No. 60/256,216, filed Dec. 14, 2000 by Pittner et al.

U.S. Appl. No. 60/324,406, filed Sep. 24, 2001 by Cowley et al.

Holst, "Plasma Enteroglucagon after Jejunoileal Bypass with 3:1 or 1:3 Jejunoileal Ratio", Scand. J. Gastroenterol, 14:205-207 (1979).

Search Report dated Sep. 17, 2008 from European Application No. EP07254859.

Dakin et al, Repeated ICV administration of oxyntomodulin causes a greater reduction in body weight gain than in pair-fed rats, Am. J. Physiol. Endocrinol. Metab, 2002, E1173-E1177, 283.

Massie, "Obesity and heart failure-Risk factor or mechanism?", N. Engl. J. Med., 347:358 (2002).

McGowan and Bloom, "Peptide YY and appetite control", Curro Opin. Pharmacol., 4(6):583-8 (2004).

McNeely, "Sibutramine. A review of its contribution to the management of obesity", Drugs, 56(6):1093-1124 (1998).

Melagros, "Release of vasodilator, but not vasoconstrictor, neuropeptides and of enteroglucagon by intestinal ischaemia/reperfusion in the rat", Gut, 35:1701 (1994).

Messer, "Vasopressin and Oxytocin", retrieved from http://www.neurosci.pharm.utoledo.edu/MBC3320/vassopressin.htm on Aug. 22, 2005.

Moran, "Cholecystokinin and satiety: Current perspectives", Nutrition, 16:858-865 (2000).

Moran, "Peptide YY(3-36) inhibits gastric emptying and produces acute reductions in food intake in rhesus monkeys", Am. J. Physiol. Regul. Integr. Comp. Physiol., 288(2):R384-8 (2005).

Morgan, "Inhibition of glucose stimulated insulin secretion by neuropeptide Y is mediated via the YI receptor and inhibition of adenylyl cyclase in RIN 5AH rat insulinoma cells", Diabetologia, 41:1482 (1998).

Morgan, "Reduced NPY Induced Feeding in Diabetic but not Steroid-Treated Rats: Lack of Evidence for Changes in Receptor Number or Affinity", J. of Neuroendocrinology, 8:283 (1996).

Morpurgo, "Covalent modification of mushroom tyrosinase with different amphiphic polymers for pharmaceutical and biocatalysis applications", Appl. Biochem. Biotechnol., 56(1):59-72 (1996).

Naveilhan, "Attenuation of hypercholesterolemia and hyperglycemia in oblob mice by NPY Y2 receptor ablation," Peptides, 23(6):1087 (2002).

Naveilhan, "Normal feeding behavior r, body weight and leptin response require the neuropeptide Y Y2 receptor", Nature Medicine, 5(10):1188 (1999).

Naveilhan, et al., "Distinct roles of the Y1 and Y2 receptors on neuropeptide V-induced sensitization to sedation," J. Neurochem., 78; 1201 (2001).

Nightingale, "Gastrointestinal hormones in short bowel syndrome. Peptide YY may be the 'colonic brake' to gastric emptying", Gut, 39:267 (1996).

Okada, Abstract 520B, Meeting of Endocrine Society (1993).

P01272 (gi121479): "Glucagon precursor", GenBank Record dated Aug. 21, 2007, (GenBank [online] Bethesda, MD USA: United States National Library of Medicine, retrieved on Jun. 9, 2007, retrieved from internet using <URL:http://www.ncbi.nlm.nih.gov/entrezlviewer.fcgi?db=protein&val=121479>, GenBank Accession No. P01272 (gi121479).

P01273 (gi1346151): "Glucagon precursor", GenBank Record dated Jul. 10, 2007, (GenBank [online] Bethesda, MD USA: United States National Library of Medicine, retrieved on Jun. 9, 2007, retrieved from internet using <URL:http://www.ncbi.nlm.nih.gov/entrezlviewer.fcgi?db=protein&val=1346151 >, GenBank Accession No. P01273 (gi1346151).

P01275 (gi121484): "Glucagon precursor", GenBank Record dated Aug. 20, 2001, (GenBank [online] Bethesda, MD USA: United Stated National Library of Medicine, retrieved on Jun. 9, 2007, retrieved from internet using <URL:http://www.ncbi.nlm.nih.gov/entrezlviewer.fcgi?121484: )OLD09:43184>, GenBank Accession No. P01275 (gi121484).

P01275(gi45644939): "Glucagon precursor", GenBank Record dated Jan. 23, 2007, (GenBank [online] Bethesda, MD USA: United States National Library of Medicine, retrieved on Jun. 9, 2007, retrieved from internet using <URL: http://www.ncbLnlm.nih.gov/entrezlviewer.fcgi?db=protein&va1=45644939>, GenBank Accession No. P01275 (gi45644939).

P01275: "GLUC_Human", ExPASy [online] Swiss Institute of Bioinformatics (SIB), Gasteiger E., Gattiker A., Hoogland C., Ivanyi I., Appel R.D., Bairoch A. ExPASy: the proteomics server for in depth protein knowledge and analysis Nucleic Acids Res. 31:3784-3788(2003), retrieved on May 27, 2005, retrieved from internet using <URL:http://www.au.expasy.org/cgi-bin/sprot-ft-details.pl?P01275@PEPTIDE@53@89>, ExPASy Accession No. P01275.

P06883 (gi121496): "Glucagon precursor", GenBank Record dated Jul. 10, 2007, (GenBank [online] Bethesda, MD USA: United States National Library of Medicine, retrieved on Jun. 9, 2007, retrieved from internet using <URL:http://www.ncbi.nlm.nih.gov/entrezlviewer.fcgi?db=protein&val=121496>, GenBank Accession No. P06883 (gi121496).

Parker, "Hormone Oxyntomodulin causes weight loss by Appetite reduction", retrieved from http//www.futurepundit.com/archives/002946.html on Aug. 17, 2005, accessed Aug. 29, 2006.

Pedersen-Bjergaard, "Influence of meal composition on postprandial peripheral plasma concentrations of vasoactive peptides in man", Scand. J. Clin. Lab. Invest., 56:497-503 (1996).

Pittner, "Effects of PYY[3-36] in rodent models of diabetes and obesity" Int. J. Obes., 28(8):963-71 (2004).

Playford, "Comparison of the Effects of Transforming Growth Factor a and Epidermal Growth Factor on Gastrointestinal Proliferation and Hormone Release", Digestion 57:362 (1996).

Playford, "Effects of peptide YY on the human cardiovascular system: reversal of responses to vasoactive intestinal peptide", Am. J. Physiol., 263:E740 (1992).

Playford, "Preliminary report: role of peptide YY in defence against diarrhea", The Lancet, 335, 1555 (1990).

Potter, "A novel neuropeptide Y analog, N-acetyl[Leu28, Leu31]neuropeptide Y-(24-36), with functional specificity for the presynaptic (Y2) receptor", Eur. J. Pharmacol., 267(3):253-262 (1994).

Powis, "Leptin depolarizes rat hypothalamic paraventricular nucleus neurons", Am. Phys. Society R1468 (1998).

Qin, "Direct interaction of G?? with a C-terminal G??-binding domain of the Ca2+ channel a1 subunit is responsible for channel inhibition by G protein-coupled receptors", PNAS, 94, 8866 (1997).

Raben, "The reproducibility of subjective appetite scores", Br. J. Nutr., 73:517-530 (1995).

Rasmussen, "Cimetidine suspension as adjuvant to energy restricted diet in treating obesity", BMJ., 306:1093-1096 (1993).

Rissanen, "Risk of disability and mortality due to overweight in a Finnish population", British Med. J., 301:835-837 (1990).

Rist, "The bioactive conformation of neuropeptide Y analogues at the human Y2-receptor", Eur. J. Biochem., 247:1019-1028 (1997).

Rossi and Bloom, "Central Nervous System Neuropeptides Involved in Obesity", in Handbook of Experimental Pharmacology, pp. 313-341; eds. D.H. Lockwood and T.G. Heffner, Springer, New York, (2000).

Rubinstein, "Rat and Mouse Proopiomelanocortin Gene Sequences Target Tissue-Specific Expression to the Pituitary Gland but not to the Hypothalamus of Transgenic Mice", Neuroendocrinology, 58:373 (1993).

Rudinger, "Characteristics of the amino acids as components of a peptide hormone sequence", In: Peptide Hormones, JA Parsons, Ed., (1976) 1-7.

Sarson, "Gut hormone changes after jejunoileal (JIB) or biliopancreatic (BPB) bypass surgery for morbid obesity", Int. J. Obes., 5:471-480 (1981).

Saudek, "A preliminary trial of the programmable implantable medication system for insulin delivery", N. Engl. J. Med., 321:574 (1989).

Savage, "Effects of peptide YY (PYY) on mouth to caecum intestinal transit time and on the rate of gastric emptying in healthy volunteers", Gut, 28:166 (1987).

Savage, "Is raised plasma peptide YY afer intestinal resection in the rat responsible for the trophic response?", Gut, 26:1353 (1985).

Schjoldager, "Oxyntomodulin: a potential hormone from the distal gut. Pharmacokinetics and effects on gastric acid and insulin secretion in man", Eur. J. Clin. Invest., 18(5):499-503 (1988).

Schober, "The neuropeptide Y Y1 antagonist, 1229U91, a potent agonist for the human pancreatic polypeptide-preferring (NPY Y4) receptor", Peptides, 19(3):537-42 (1998).

Schutz, "Exercise and postprandial thermogenesis in obese women before and after weight loss", Am. J. Clin. Nutr., 45(6):1424-32 (1987).

Schwartz, "Central nervous system control of food intake", Nature, 404:661-671 (2000).

Search Report dated Apr. 9, 2004 from International Application No. PCT/US02/31944.

Search Report dated Jan. 23, 2003 from International Application No. PCT/GB02/04082.

Search Report dated Mar. 13, 2007 from International Application No. PCT/GB2006/002155.

Search Report dated May 21, 2008 from International Application No. PCT/GB2007/004779.

Search Report dated Oct. 19, 2007 from International Application No. PCT/GB2007/002473.

Figure 1

Figure 1 (continued)

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|
| PEPTIDE NO: 51 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Leu | Glu | Trp | Leu | Met | Asn | Thr | Lys | Arg | Asn | Lys | Asn | Asn | Ile | Ala |
| PEPTIDE NO: 52 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Leu | Gln | Trp | Leu | Lys | Asn | Ala | Gly | Pro | Ser | Lys | Asn | Asn | Ile | Ala |
| PEPTIDE NO: 53 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Leu | Gln | Trp | Leu | Lys | Asn | Gly | Gly | Pro | Ser | Lys | Asn | Asn | Ile | Ala |
| PEPTIDE NO: 54 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Glu | Trp | Leu | Lys | Asn | Thr | Lys | Pro | Ser | Lys | Asn | Asn | Ile | Ala |
| PEPTIDE NO: 55 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 56 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Lys | Asn | Gly | Gly | Pro | Asn | Lys | Asn | Asn | Ile | Ala |
| PEPTIDE NO: 57 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Met | Asn | Thr | Lys | Arg | Ser | Lys | Asn | Asn | Ile | Ala |
| PEPTIDE NO: 58 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 59 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Met | Asn | Thr | Lys | Arg | Asn | Lys | Asn | Asn | Ile | Ala |
| PEPTIDE NO: 60 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Glu | Trp | Leu | Lys | Asn | Ala | Gly | Pro | Ser | Lys | Asn | Asn | Ile | Ala |
| PEPTIDE NO: 61 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Glu | Trp | Leu | Lys | Asn | Gly | Gly | Pro | Ser | Lys | Asn | Asn | Ile | Ala |
| PEPTIDE NO: 62 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Lys | Asn | Thr | Lys | Pro | Ser | Lys | Asn | Asn | Ile | Ala |
| PEPTIDE NO: 63 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 64 | D-His | Ser | Gln | Gly | Thr | Phe | Thr | Ser | Asp | Tyr | Ser | Lys | Tyr | Leu | Glu | Glu | Glu | Leu | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 65 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Gln | Trp | Leu | Met | Asn | Thr | Lys | Arg | Ser | Lys | Asn | Asn | Ile | Ala |
| PEPTIDE NO: 66 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 67 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 68 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Glu | Trp | Leu | Lys | Asn | Thr | Lys | Pro | Ser | Lys | Asn | Asn | Ile | Ala |
| PEPTIDE NO: 69 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Glu | Trp | Leu | Lys | Asn | Ala | Gly | Pro | Ser | Lys | Asn | Asn | Ile | Ala |
| PEPTIDE NO: 70 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Glu | Trp | Leu | Lys | Asn | Gly | Gly | Pro | Ser | Lys | Asn | Asn | Ile | Ala |
| PEPTIDE NO: 71 | D-His | Ser | Gln | Gly | Thr | Phe | Thr | Ser | Asp | Tyr | Ser | Lys | Tyr | Leu | Glu | Glu | Glu | Ile | Val | Lys | Tyr | Phe | Ile | Gln | Trp | Leu | Lys | Asn | Thr | Lys | Arg | Ser | Lys | Asn | Asn | Ile | Ala |
| PEPTIDE NO: 72 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 73 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 74 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Glu | Trp | Leu | Met | Asn | Thr | Lys | Arg | Ser | Lys | Asn | Asn | Ile | Ala |
| PEPTIDE NO: 75 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Gln | Trp | Leu | Lys | Asn | Ala | Gly | Pro | Ser | Lys | Asn | Asn | Ile | Ala |
| PEPTIDE NO: 76 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Gln | Trp | Leu | Lys | Asn | Gly | Gly | Pro | Ser | Lys | Asn | Asn | Ile | Ala |
| PEPTIDE NO: 77 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Glu | Trp | Leu | Lys | Asn | Thr | Lys | Pro | Ser | Lys | Asn | Asn | Ile | Ala |
| PEPTIDE NO: 78 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 79 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 80 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Glu | Trp | Leu | Lys | Asn | Thr | Lys | Arg | Ser | Lys | Asn | Asn | Ile | Ala |
| PEPTIDE NO: 81 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Gln | Trp | Leu | Met | Asn | Thr | Lys | Arg | Asn | Lys | Asn | Asn | Ile | Ala |
| PEPTIDE NO: 82 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 83 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 84 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Gln | Trp | Leu | Met | Asn | Thr | Lys | Arg | Ser | Lys | Asn | Asn | Ile | Ala |
| PEPTIDE NO: 85 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Gln | Trp | Leu | Lys | Asn | Ala | Gly | Pro | Ser | Lys | Asn | Asn | Ile | Ala |
| PEPTIDE NO: 86 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Gln | Trp | Leu | Lys | Asn | Gly | Gly | Pro | Ser | Lys | Asn | Asn | Ile | Ala |
| PEPTIDE NO: 87 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Glu | Trp | Leu | Lys | Asn | Thr | Lys | Pro | Ser | Lys | Asn | Asn | Ile | Ala |
| PEPTIDE NO: 88 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Glu | Trp | Leu | Lys | Asn | Ala | Gly | Pro | Ser | Lys | Asn | Asn | Ile | Ala |
| PEPTIDE NO: 89 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Glu | Trp | Leu | Lys | Asn | Gly | Gly | Pro | Ser | Lys | Asn | Asn | Ile | Ala |
| PEPTIDE NO: 90 | D-His | Ser | Gln | Gly | Thr | Phe | Thr | Ser | Asp | Tyr | Ser | Lys | Tyr | Leu | Glu | Gln | Glu | Ile | Val | Lys | Tyr | Phe | Ile | Gln | Trp | Leu | Met | Asn | Thr | Lys | Arg | Asn | Lys | Asn | Asn | Ile | Ala |
| PEPTIDE NO: 91 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Glu | Trp | Leu | Lys | Asn | Thr | Lys | Pro | Ser | Lys | Asn | Asn | Ile | Ala |
| PEPTIDE NO: 92 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Glu | Trp | Leu | Met | Asn | Thr | Lys | Arg | Ser | Lys | Asn | Asn | Ile | Ala |
| PEPTIDE NO: 93 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Glu | Trp | Leu | Met | Asn | Thr | Lys | Arg | Asn | Lys | Asn | Asn | Ile | Ala |
| PEPTIDE NO: 94 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Glu | Trp | Leu | Met | Asn | Thr | Lys | Arg | Ser | Lys | Asn | Asn | Ile | Ala |
| PEPTIDE NO: 95 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Ile | Glu | Trp | Leu | Met | Asn | Thr | Lys | Arg | Asn | Lys | Asn | Asn | Ile | Ala |
| PEPTIDE NO: 96 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Glu | Trp | Leu | Lys | Asn | Thr | Lys | Arg | Ser | Lys | Asn | Asn | Ile | Ala |
| PEPTIDE NO: 97 | D-His | Ser | Gln | Gly | Thr | Phe | Thr | Ser | Asp | Tyr | Ser | Lys | Tyr | Leu | Glu | Gln | Glu | Leu | Val | Lys | Tyr | Phe | Leu | Gln | Trp | Leu | Met | Asn | Ala | Gly | Pro | Ser | Lys | Asn | Asn | Ile | Ala |
| PEPTIDE NO: 98 | D-His | Ala | Gln | Gly | Thr | Phe | Thr | Ser | Asp | Tyr | Ser | Lys | Tyr | Leu | Glu | Gln | Glu | Leu | Val | Lys | Tyr | Phe | Leu | Gln | Trp | Leu | Lys | Asn | Thr | Gly | Arg | Ser | Lys | Asn | Asn | Ile | Ala |
| PEPTIDE NO: 99 | D-His | Ala | Gln | Gly | Thr | Phe | Thr | Ser | Asp | Tyr | Ser | Lys | Tyr | Leu | Glu | Gln | Glu | Leu | Val | Lys | Tyr | Phe | Leu | Gln | Trp | Leu | Met | Asn | Thr | Lys | Arg | Ser | Lys | Asn | Asn | Ile | Ala |
| PEPTIDE NO: 100 | D-His | Ala | Gln | Gly | Thr | Phe | Thr | Ser | Asp | Tyr | Ser | Lys | Tyr | Leu | Glu | Gln | Glu | Leu | Val | Lys | Tyr | Phe | Leu | Gln | Trp | Leu | Lys | Asn | Ala | Gly | Pro | Ser | Lys | Asn | Asn | Ile | Ala |

COMPOUNDS AND THEIR EFFECTS ON FEEDING BEHAVIOUR

CROSS REFERENCE TO RELATED APPLICATIONS

This application claims priority to GB 06 24868.6 filed Dec. 13, 2006; GB 06 25667.1 filed Dec. 21, 2006; and GB 07 00897.2 filed Jan. 17, 2007.

1. FIELD OF THE INVENTION

This application relates to the use of agents to control appetite, feeding, food intake, energy expenditure and calorie intake, treat excess weight, obesity and to prevent and treat the co-morbidities of obesity.

2. BACKGROUND OF THE INVENTION

According to the World Health Organisation (WHO), obesity represents a global epidemic in which more than one billion adults are overweight, of which at least 300 million are clinically obese. Furthermore, WHO estimate that 250,000 deaths per year in Europe, and more than 2.5 million deaths worldwide are weight related (World Health Organisation, Global Strategy on Diet, Physical Activity and Health, 2004).

The cause of obesity is complex and multi-factorial. Increasing evidence suggests that obesity is not a simple problem of self-control but is a complex disorder involving appetite regulation and energy metabolism. In addition, obesity is associated with a variety of conditions associated with increased morbidity and mortality in a population. Although the etiology of obesity is not definitively established, genetic, metabolic, biochemical, cultural and psychosocial factors are believed to contribute. In general, obesity has been described as a condition in which excess body fat puts an individual at a health risk.

There is strong evidence that obesity is associated with increased morbidity and mortality. Disease risk, such as cardiovascular disease risk and type 2 diabetes disease risk, increases independently with increased body mass index (BMI). Indeed, this risk has been quantified as a five percent increase in the risk of cardiac disease for females, and a seven percent increase in the risk of cardiac disease for males, for each point of a BMI greater than 24.9 (see Kenchaiah et al., N. Engl. J. Med. 347:305, 2002; Massie, N. Engl. J. Med. 347: 358, 2002). In addition, there is substantial evidence that weight loss in obese or overweight persons reduces important disease risk factors. A weight loss of 10% of the initial body weight in both overweight and obese adults has been associated with a decrease in risk factors such as hypertension, hyperlipidemia, and hyperglycemia.

Although diet and exercise provide a simple process to decrease weight gain and promote weight loss, overweight and obese individuals often cannot sufficiently control these factors to lose weight effectively. Pharmacotherapy is available; several weight loss drugs have been approved by the US Food and Drug Administration that can be used as part of a comprehensive weight loss program. However, many of these drugs have serious adverse side effects. An example of a widely used appetite suppressant is sibutramine (reviewed by McNeely, W et al., Drugs, 1998, 56(6), 1093-1124). Sibutramine's primary and secondary metabolites are pharmacologically active and they are thought to induce enhancement of satiety and thermogenesis by inhibiting serotonin and noradrenaline reuptake. When less invasive methods have failed, and the patient is at high risk for obesity related morbidity or mortality, weight loss surgery is an option in carefully selected patients with clinically severe obesity. However, these treatments are high-risk, and suitable for use in only a limited number of patients (Wolfe and Morton, JAMA, 2005, 294, 1960-1963). It is not only obese subjects who wish to lose weight. People with weight within the recommended range, for example, in the upper part of the recommended range, may wish to reduce their weight, to bring it closer to the ideal weight.

Oxyntomodulin (hereafter oxm) is a 37 amino acid peptide member of the glucagon superfamily (Sherwood et al, Endocrine Reviews, 2000, 21(6): 619-670) comprising the entire 29 amino acid sequence of glucagon, with an eight amino acid carboxy terminal extension, resulting from the tissue-specific processing of the pre-pro-glucagon precursor in the brain and gut (Holst, Ann Rev Physiol, 1997, 59:257-271). Administration of oxm to rats via intracerebroventricular injection and injection into the paraventricular and arcuate nuclei of the hypothalamus inhibits refeeding after a fast (Dakin et al, Endocrinology, 2001, 142:4244-4250; Dakin et al, Endocrinology, 2004, 145:2687-2695). Chronic central administration resulted in reduced weight gain consistent with a reduction in food intake (Dakin et al, Am J Physiol Endocrinol Metab, 2002, 283:E1173-E1177). Twice daily peripheral injections also resulted in reduced body weight gain and adiposity (Dakin et al, Endocrinology, 2004, 145:2687-2695).

WO 03/022304 discloses the use of oxm in its native form and analogues thereof as a medicament for use in control of appetite, feeding, food intake, energy expenditure and calorie intake, particularly in the field of obesity. Studies in humans have shown that intravenously infused oxm is an effective appetite suppressant (Cohen et al, J. Clin. Endocrinol Metab, 2003, 88(10): 4696-4701). In a study of the effects of oxm on weight loss in humans it was found that subcutaneous injections of 1.8 mg (approximately 400 nmol) of oxm to human volunteers three times daily (30 mins before meals) for 28 days resulted in a significant reduction of body weight (Wynne et al, Diabetes, 2005, 54: 2390-2395).

Peptides are widely used in medical practice, although when native peptides or analogues thereof are used in therapy it is generally found that they have a high clearance rate and/or are sensitive to degradation. In particular, a high clearance or rapid degradation of a therapeutic agent is inconvenient in cases where it is desired to maintain a high blood level over a prolonged period of time since repeat administrations will then be necessary, decreasing patient compliance and increasing the cost of the therapy.

A need remains for agents that can be used to effect weight loss in overweight and obese subjects, and/or to treat patients with other conditions involving excess weight, for example diabetes and eating disorders. There is especially a need for agents structurally similar to oxm that show greater potency and/or a protracted or more therapeutically useful profile of action and/or a lower clearance rate than native oxm.

3. SUMMARY OF THE INVENTION

Compounds of the invention are novel peptide analogues of oxm (hereafter "oxm analogues") in which one or more amino acids or parts of the oxm sequence have been replaced by one or more particular substituent amino acids or sequences. Accordingly, the invention provides a peptide comprising the amino acid sequence:

Xaa1 Xaa2 Xaa3 Gly4 Thr5 Phe6 Thr7 Ser8 Asp9 Tyr10 Ser11 Lys12 Tyr13 Leu14 Xaa15 Xaa16 Xaa17 Xaa18 Xaa19 Xaa20 Xaa21 Xaa22 Xaa23 Xaa24 Trp25 Leu26 Xaa27 Xaa28 Xaa29 Xaa30 Xaa31 Xaa32 Lys33 Asn34 Asn35 Ile36 Ala37;

wherein:

Xaa1 is His1 or D-His1,

Xaa2 is Ser2 or Ala2,

Xaa3 is Gln3 or Asp3;

Xaa15 Xaa16 Xaa17 Xaa18 Xaa19 Xaa20 Xaa21 Xaa22 Xaa23 Xaa24 is:

Glu15 Glu16 Glu17 Leu18 Val19 Lys20 Tyr21 Phe22 Leu23 Glu24,

Glu15 Glu16 Glu17 Leu18 Val19 Lys20 Tyr21 Phe22 Leu23 Gln24,

Glu15 Glu16 Glu17 Leu18 Val19 Lys20 Tyr21 Phe22 Ile23 Glu24,

Glu15 Glu16 Glu17 Leu18 Val19 Lys20 Tyr21 Phe22 Ile23 Gln24,

Glu15 Glu16 Glu17 Ile18 Val19 Lys20 Tyr21 Phe22 Leu23 Glu24,

Glu15 Glu16 Glu17 Ile18 Val19 Lys20 Tyr21 Phe22 Leu23 Gln24,

Glu15 Glu16 Glu17 Ile18 Val19 Lys20 Tyr21 Phe22 Ile23 Glu24,

Glu15 Glu16 Glu17 Ile18 Val19 Lys20 Tyr21 Phe22 Ile23 Gln24,

Glu15 Gln16 GLu17 Leu18 Val19 Lys20 Tyr21 Phe22 Leu23 Glu24,

Glu15 Gln16 Glu17 Leu18 Val19 Lys20 Tyr21 Phe22 Leu23 Gln24,

Glu15 Gln16 Glu17 Leu18 Val19 Lys20 Tyr21 Phe22 Ile23 Glu24,

Glu15 Gln16 Glu17 Leu18 Val19 Lys20 Tyr21 Phe22 Ile23 Gln24,

Glu15 Gln16 Glu17 Ile18 Val19 Lys20 Tyr21 Phe22 Leu23 Glu24,

Glu15 Gln16 Glu17 Ile18 Val19 Lys20 Tyr21 Phe22 Leu23 Gln24,

Glu15 Gln16 Glu17 Ile18 Val19 Lys20 Tyr21 Phe22 Ile23 Glu24,

Glu15 Gln16 Glu17 Ile18 Val19 Lys20 Tyr21 Phe22 Ile23 Gln24,
or

Asp15 Ser16 Arg17 Arg18 Ala19 Gln20 Asp21 Phe22 Val23 Gln24;

Xaa27 Xaa28 Xaa29 Xaa30 Xaa31 Xaa32 is:

Met27 Asn28 Thr29 Lys30 Arg31 Asn32,

Lys27 Asn28 Ala29 Gly30 Pro31 Ser32,
or

Lys27 Asn28 Gly29 Gly30 Pro31 Ser32 or a peptide as set out above in which residue Asn34 is replaced with Asp34;
or a peptide as set out above in which Xaa3 is Glu3;
with the proviso that if Xaa15 Xaa16 Xaa17 Xaa18 Xaa19 Xaa20 Xaa21 Xaa22 Xaa23 Xaa24 is (SEQ ID NO: 356)

Asp15 Ser16 Arg17 Arg18 Ala19 Gln20 Asp21 Phe22 Val23 Gln24, then
Xaa27 Xaa28 Xaa29 Xaa30 Xaa31 Xaa32 is not Met27 Asn28 Thr29 Lys30 Arg31 Asn32.

In one embodiment, the invention provides a peptide comprising the amino acid sequence:
Xaa1 Xaa2 Xaa3 Gly4 Thr5 Phe6 Thr7 Ser8 Asp9 Tyr10 Ser11 Lys12 Tyr13 Leu14 Xaa15 Xaa16 Xaa17 Xaa18 Xaa19 Xaa20 Xaa21 Xaa22 Xaa23 Xaa24 Trp25 Leu26 Xaa27 Xaa28 Xaa29 Xaa30 Xaa31 Xaa32 Lys33 Asn34 Asn35 Ile36 Ala37;
wherein:

Xaa1 is His1 or D-His1,

Xaa2 is Ser2 or Ala2,

```
-continued
Xaa3 is Gln3 or Asp3;

Xaa15 Xaa16 Xaa17 Xaa18 Xaa19 Xaa20 Xaa21 Xaa22 Xaa23 Xaa24 is:

Glu15 Glu16 Glu17 Leu18 Val19 Lys20 Tyr21 Phe22 Leu23 Glu24,

Glu15 Glu16 Glu17 Leu18 Val19 Lys20 Tyr21 Phe22 Leu23 Gln24,

Glu15 Glu16 Glu17 Leu18 Val19 Lys20 Tyr21 Phe22 Ile23 Glu24,

Glu15 Glu16 Glu17 Leu18 Val19 Lys20 Tyr21 Phe22 Ile23 Gln24,

Glu15 Glu16 Glu17 Ile18 Val19 Lys20 Tyr21 Phe22 Leu23 Glu24,

Glu15 Glu16 Glu17 Ile18 Val19 Lys20 Tyr21 Phe22 Leu23 Gln24,

Glu15 Glu16 Glu17 Ile18 Val19 Lys20 Tyr21 Phe22 Ile23 Glu24,

Glu15 Glu16 Glu17 Ile18 Val19 Lys20 Tyr21 Phe22 Ile23 Gln24,

Glu15 Gln16 Glu17 Leu18 Val19 Lys20 Tyr21 Phe22 Leu23 Glu24,

Glu15 Gln16 Glu17 Leu18 Val19 Lys20 Tyr21 Phe22 Leu23 Gln24,

Glu15 Gln16 Glu17 Leu18 Val19 Lys20 Tyr21 Phe22 Ile23 Glu24,

Glu15 Gln16 Glu17 Leu18 Val19 Lys20 Tyr21 Phe22 Ile23 Gln24,

Glu15 Gln16 Glu17 Ile18 Val19 Lys20 Tyr21 Phe22 Leu23 Glu24,

Glu15 Gln16 Glu17 Ile18 Val19 Lys20 Tyr21 Phe22 Leu23 Gln24,

Glu15 Gln16 Glu17 Ile18 Val19 Lys20 Tyr21 Phe22 Ile23 Glu24,

Glu15 Gln16 Glu17 Ile18 Val19 Lys20 Tyr21 Phe22 Ile23 Gln24,
or

Asp15 Ser16 Arg17 Arg18 Ala19 Gln20 Asp21 Phe22 Val23 Gln24;

Xaa27 Xaa28 Xaa29 Xaa30 Xaa31 Xaa32 is:

Met27 Asn28 Thr29 Lys30 Arg31 Asn32,

Lys27 Asn28 Ala29 Gly30 Pro31 Ser32,
or

Lys27 Asn28 Gly29 Gly30 Pro31 Ser32 with the proviso that if
Xaa15 Xaa16 Xaa17 Xaa18 Xaa19 Xaa20 Xaa21 Xaa22 Xaa23 Xaa24 is Asp15 Ser16 Arg17 Arg18 Ala19 Gln20 Asp21 Phe22 Val23 Gln24, then
Xaa27 Xaa28 Xaa29 Xaa30 Xaa31 Xaa32 is not Met27 Asn28 Thr29 Lys30 Arg31 Asn32.
```

The peptides of the invention are potent and long-lasting appetite suppressants.

4. BRIEF DESCRIPTION OF THE FIGURES

Figure 3:
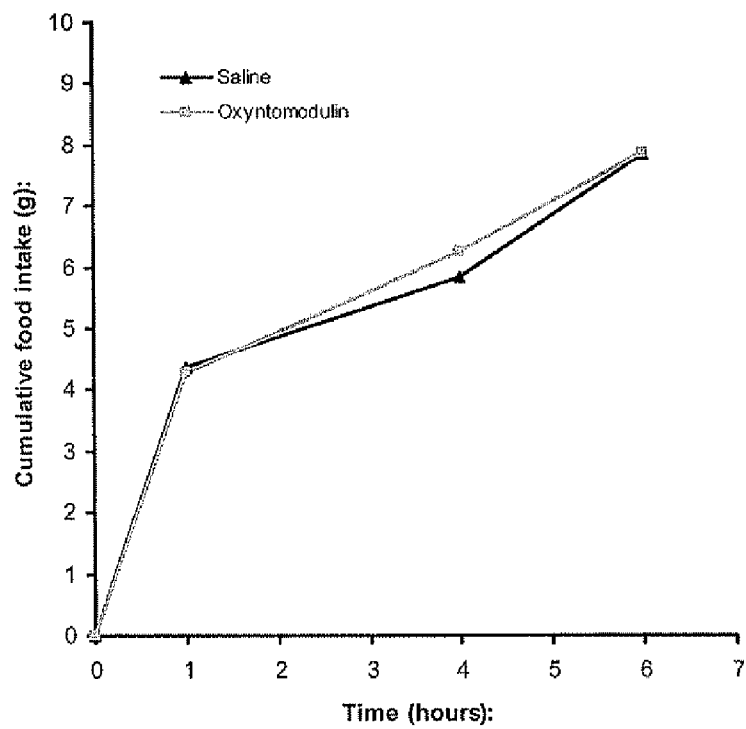
Figure 4:
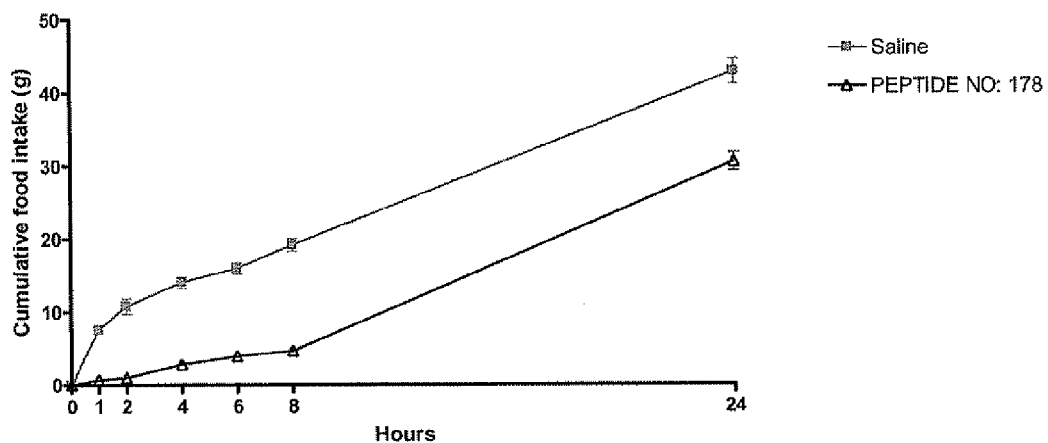
Figure 5:
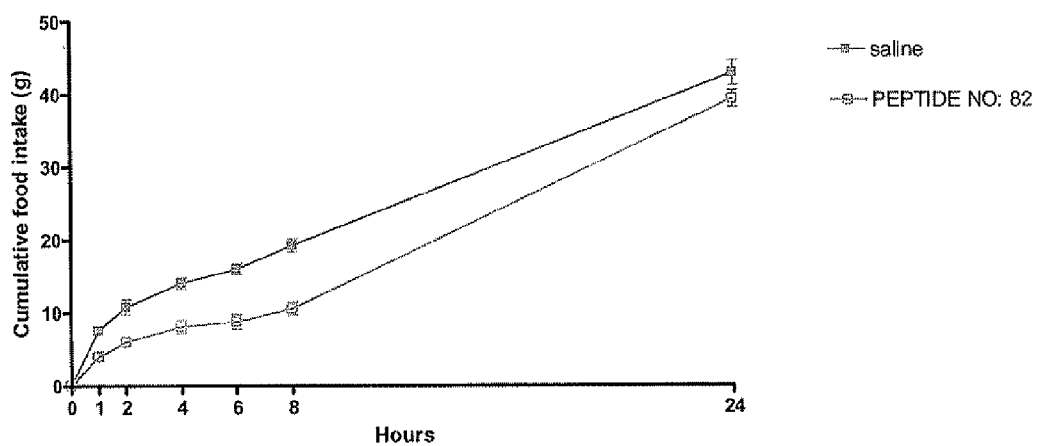
Figure 6:
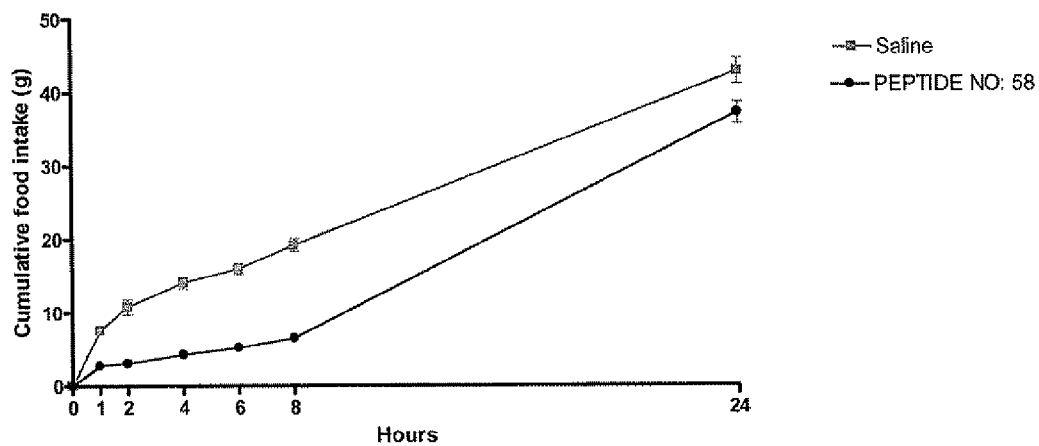
Figure 7:
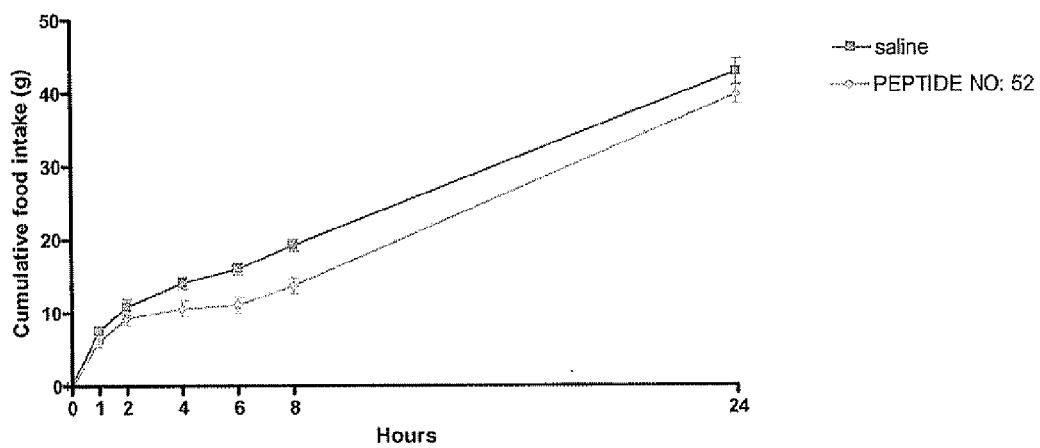
Figure 8:
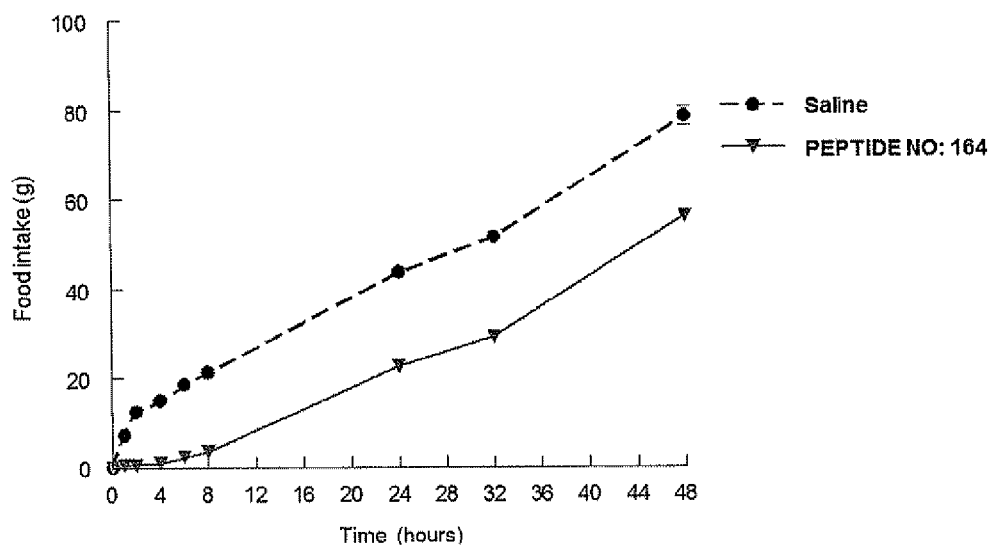
Figure 9:
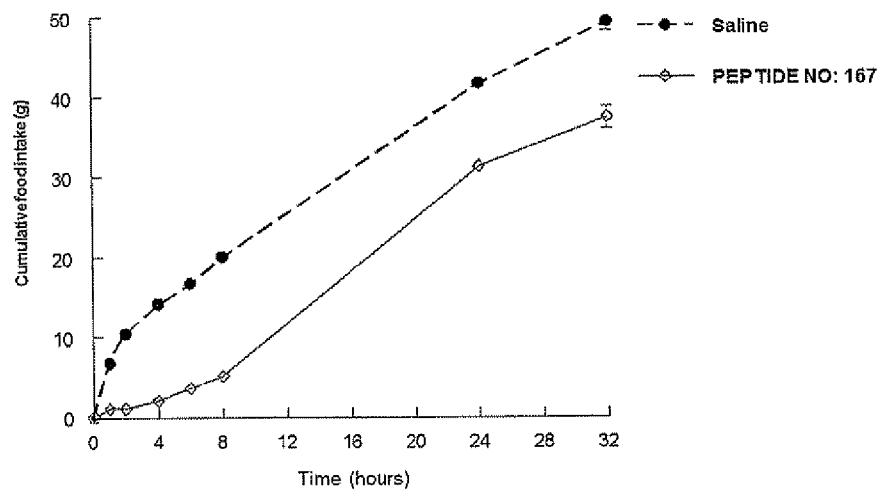
Figure 10:
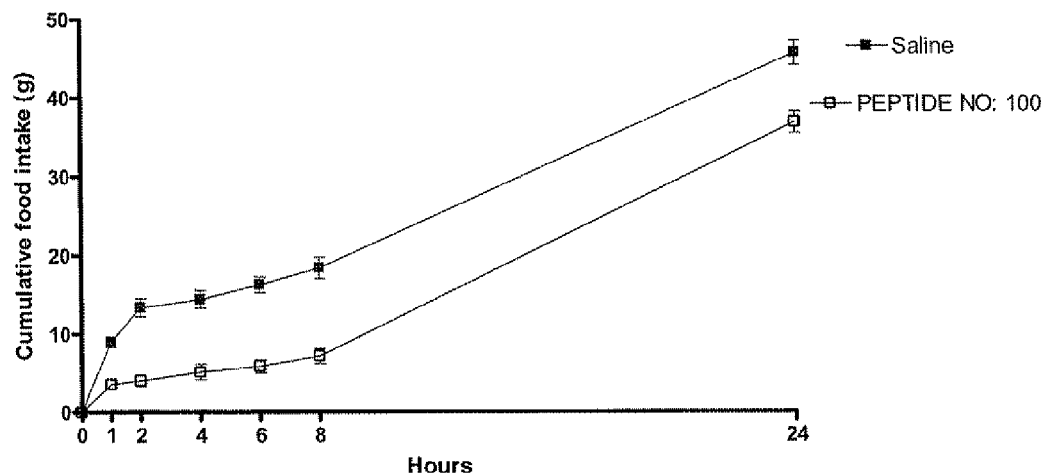
Figure 11:
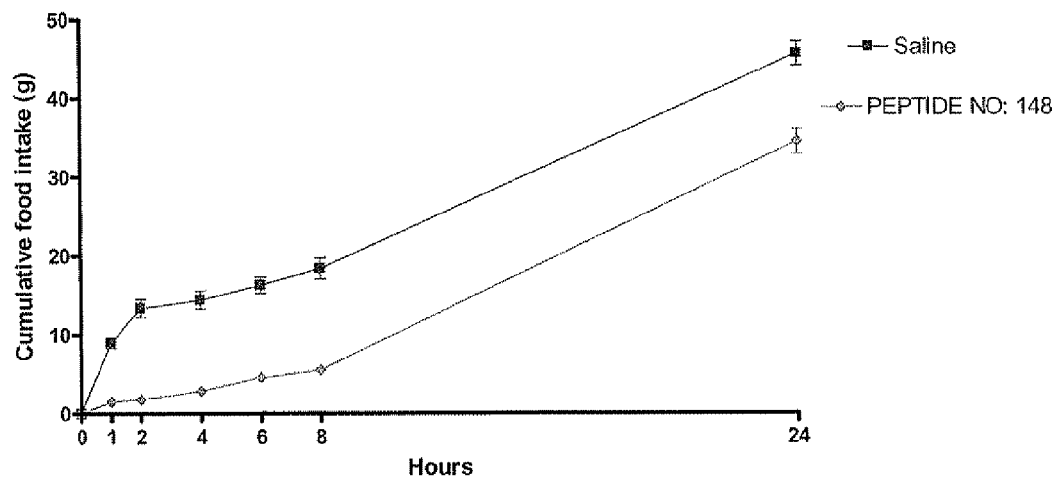
Figure 12:
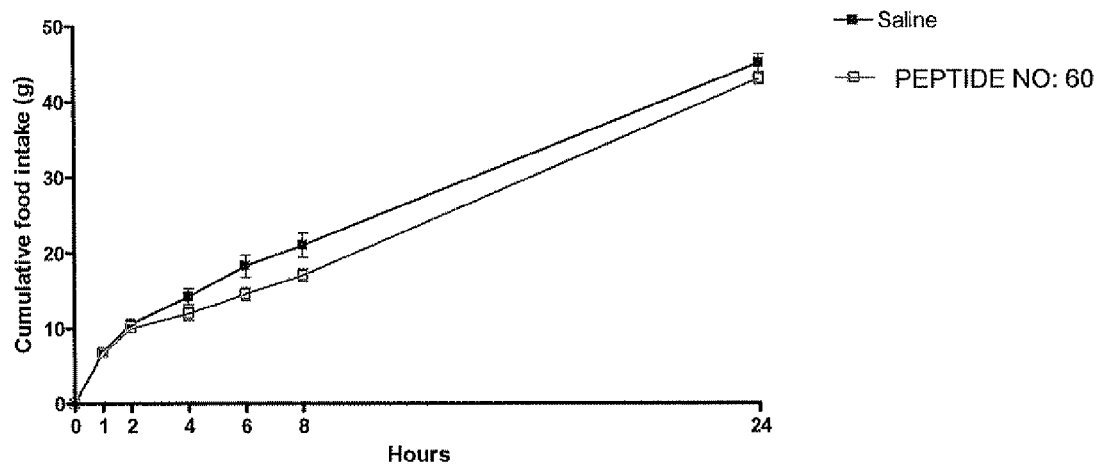
Figure 13:
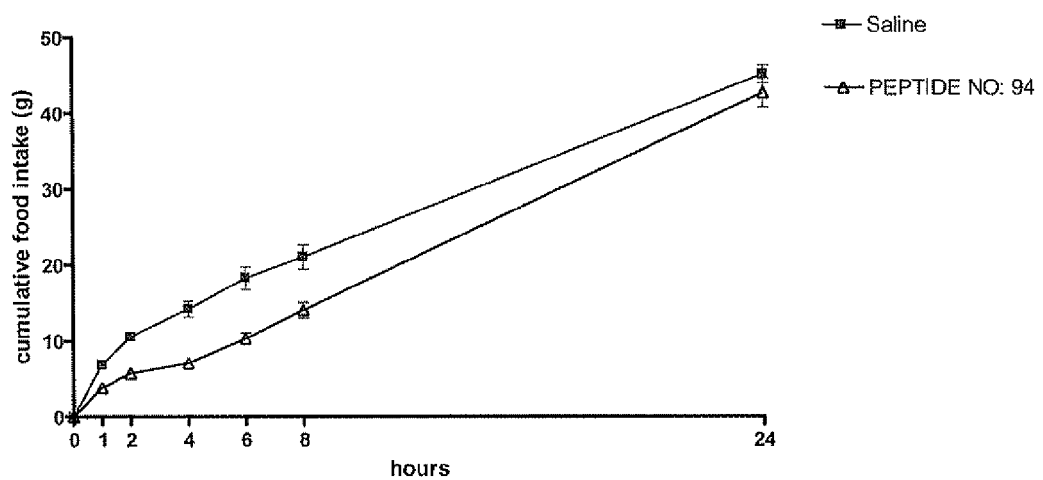
Figure 14:
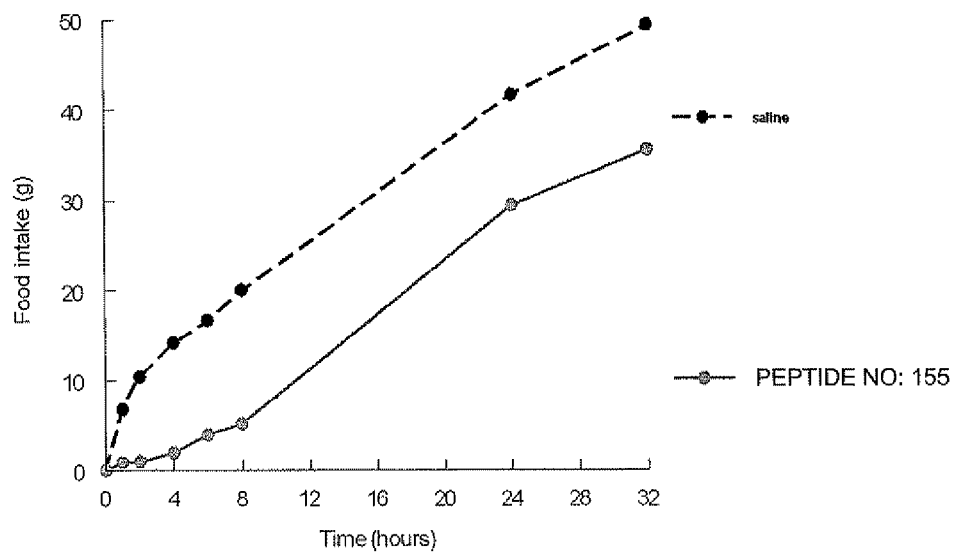
Figure 15:
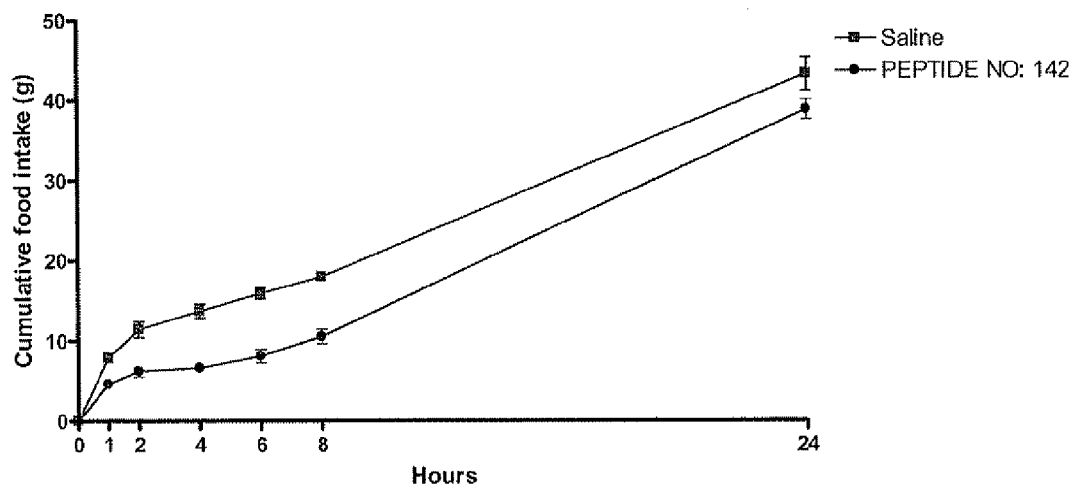
Figure 16:
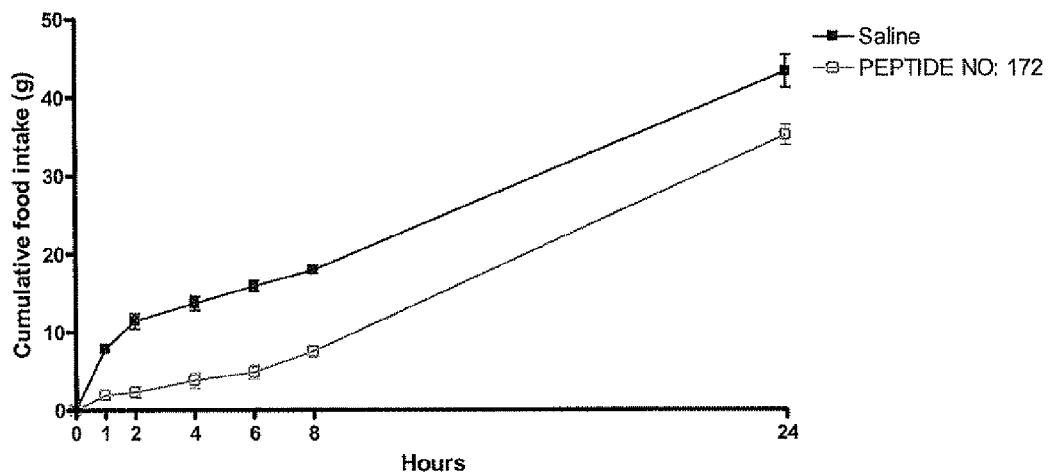
Figure 17:
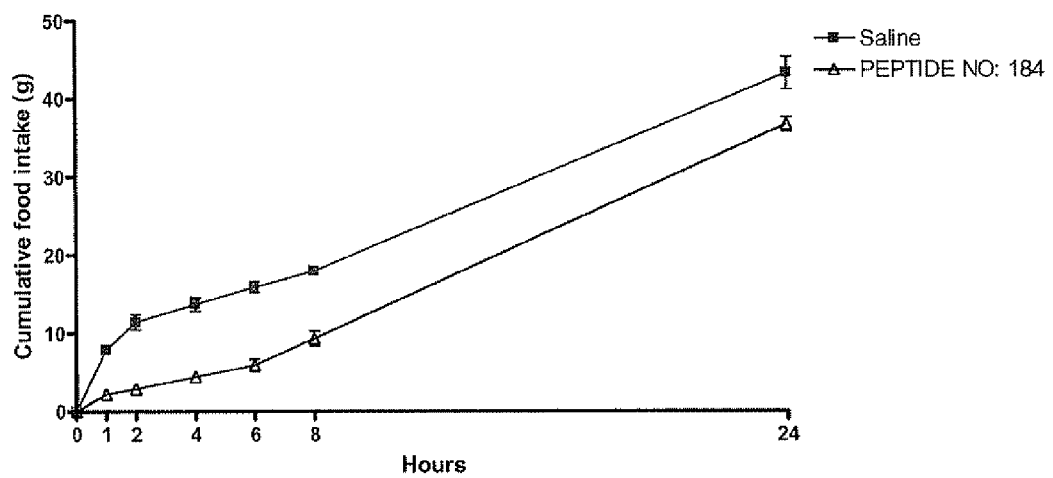
Figure 18:
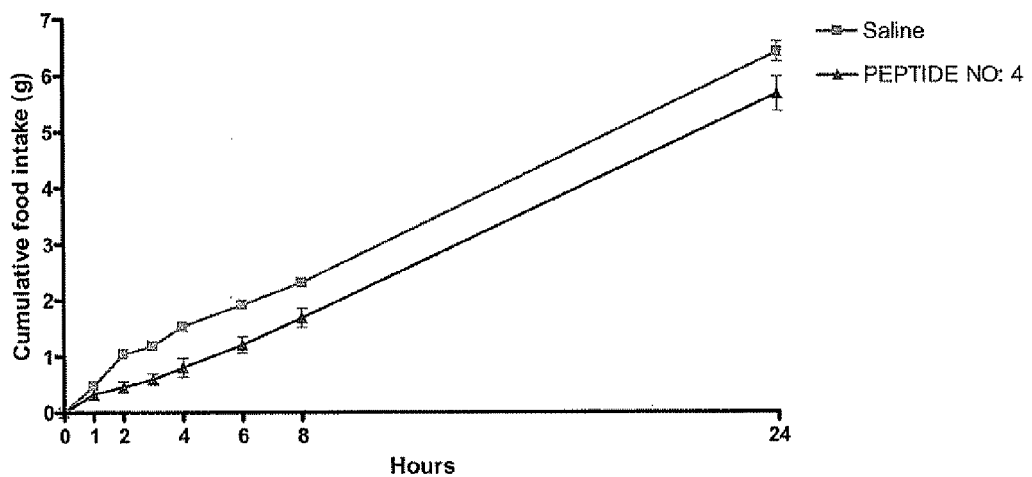
Figure 19:
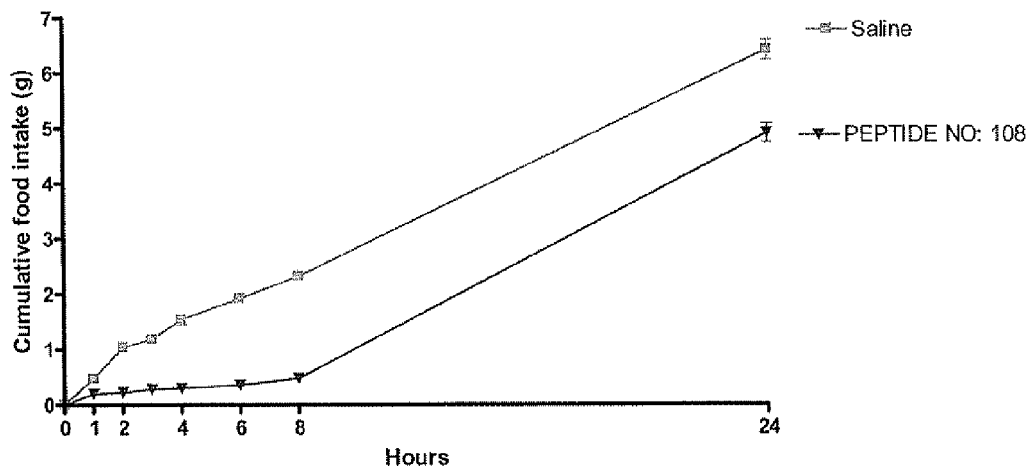
Figure 20:
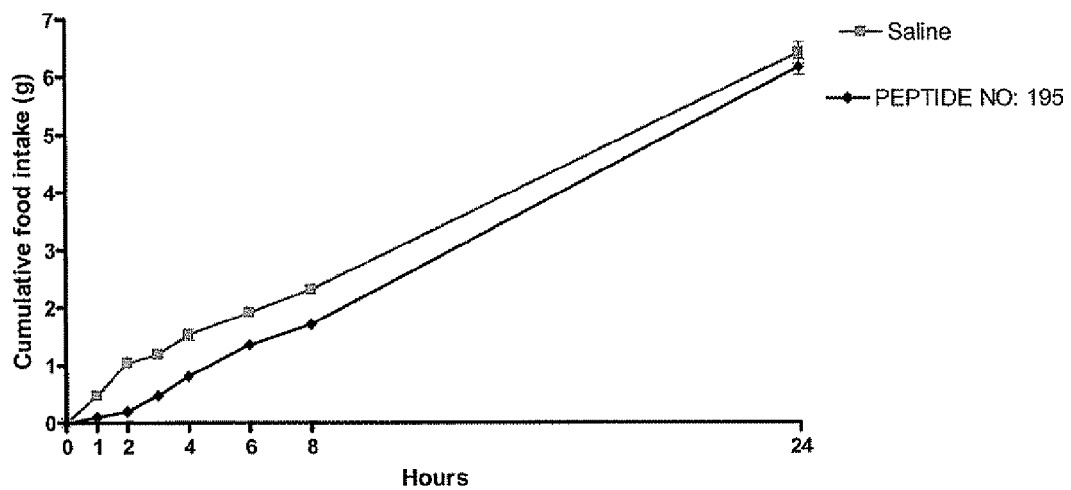
Figure 21:
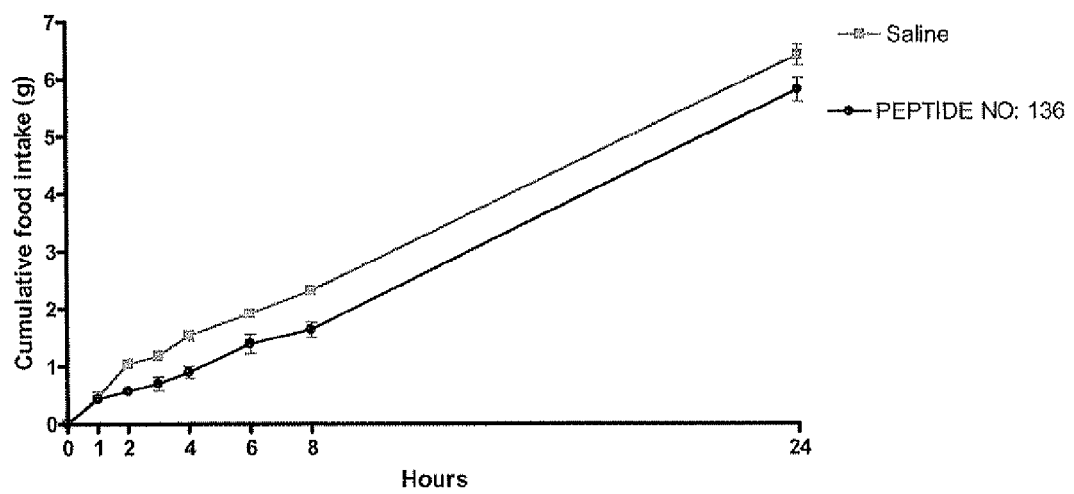
Figure 22:
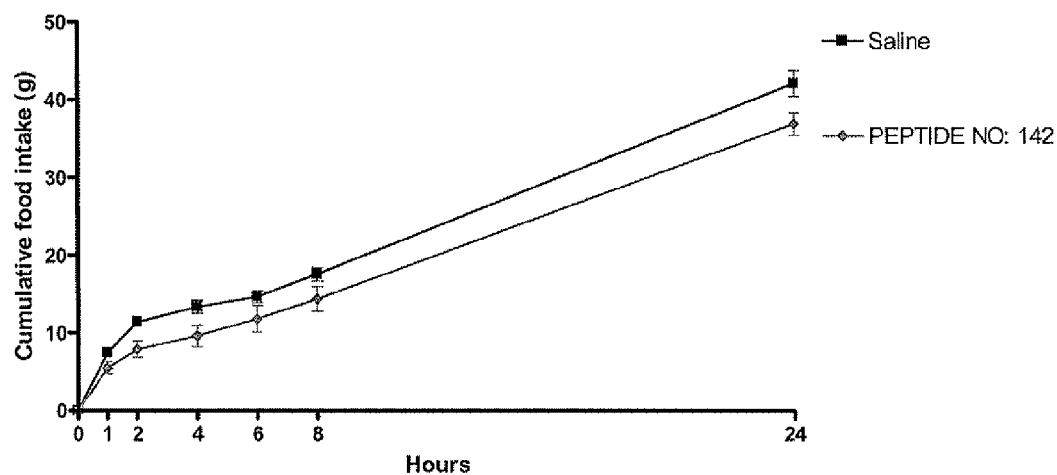
Figure 23:
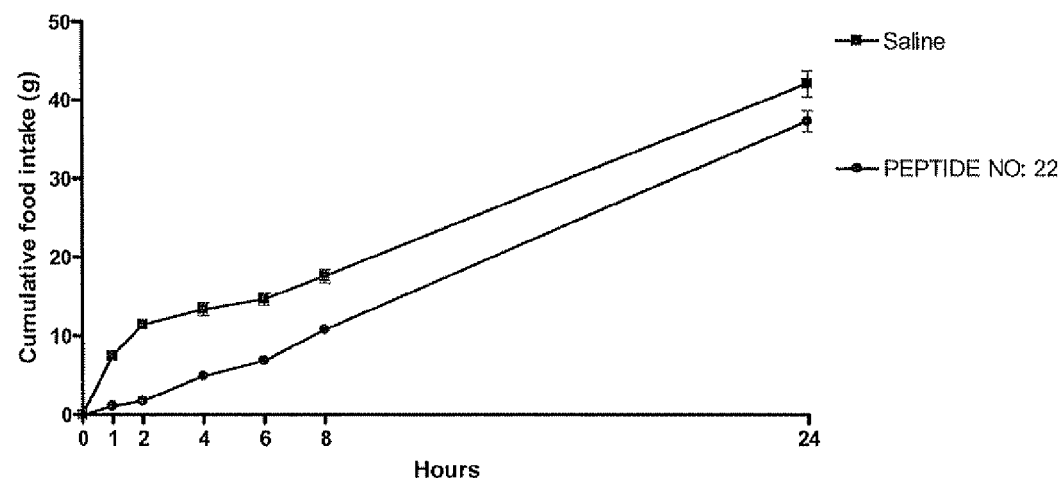
Figure 24:
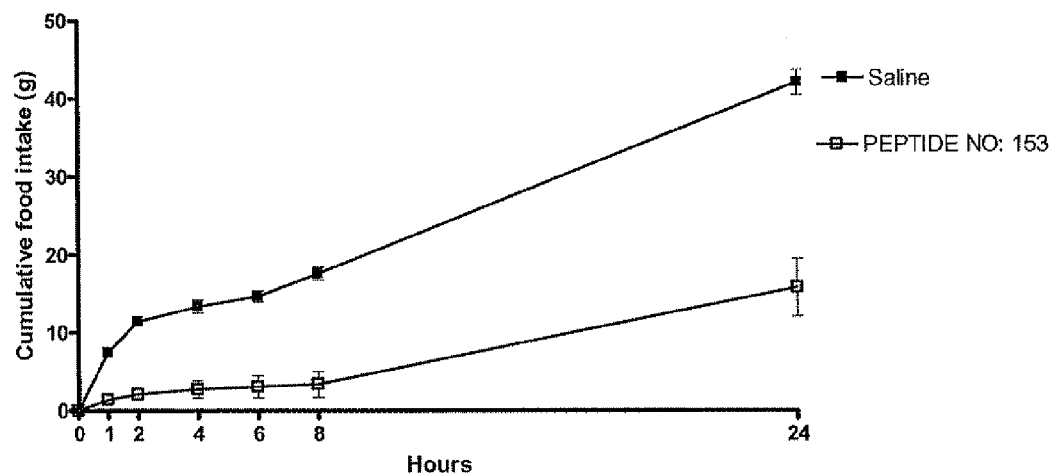
Figure 25:
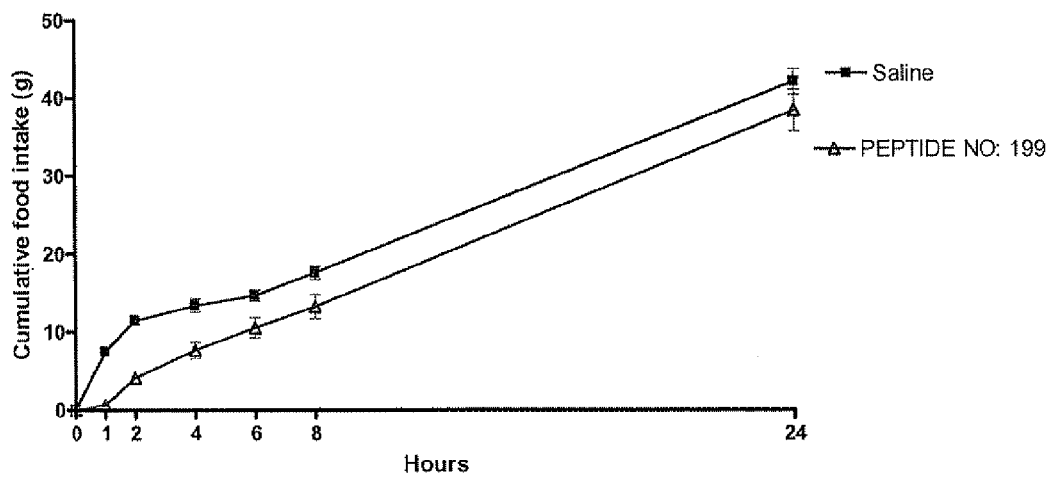
Figure 26:
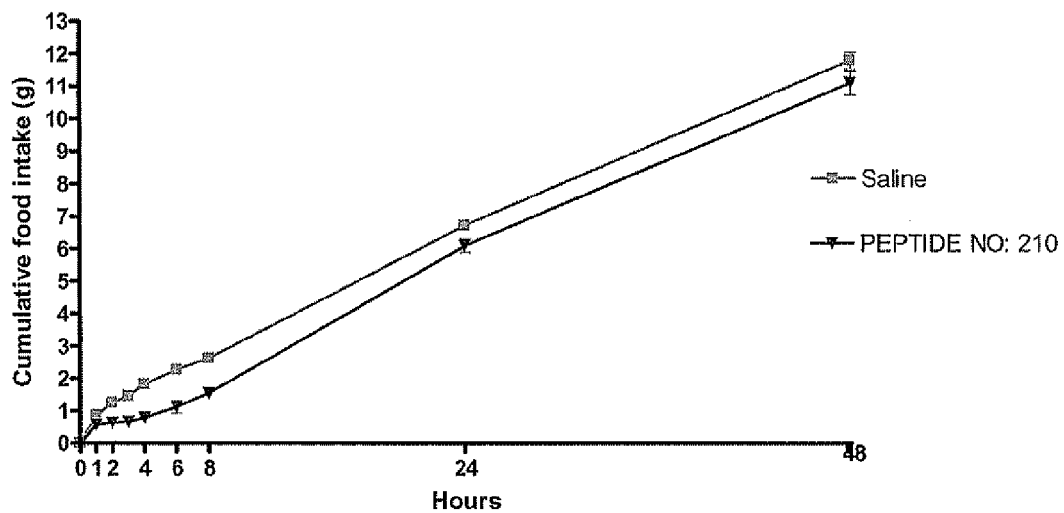
Figure 27:
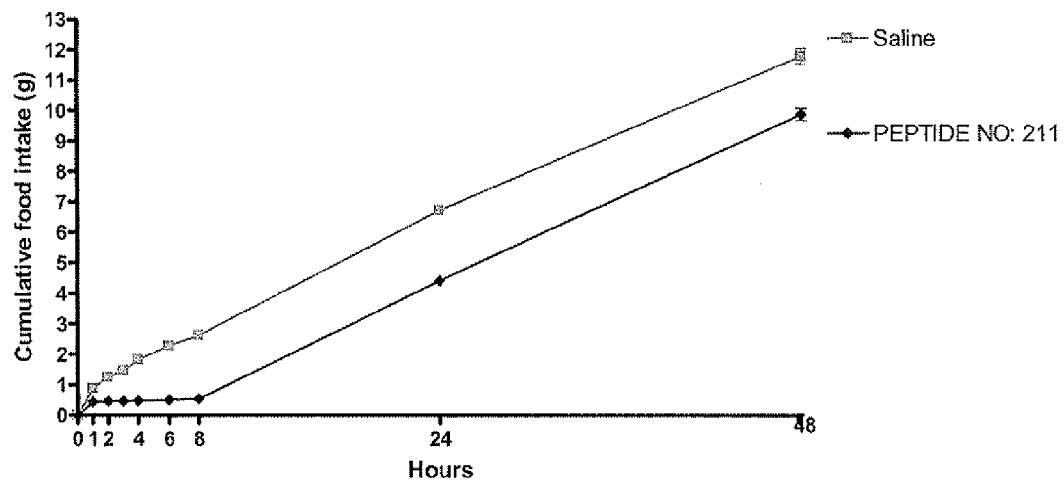
Figure 28:
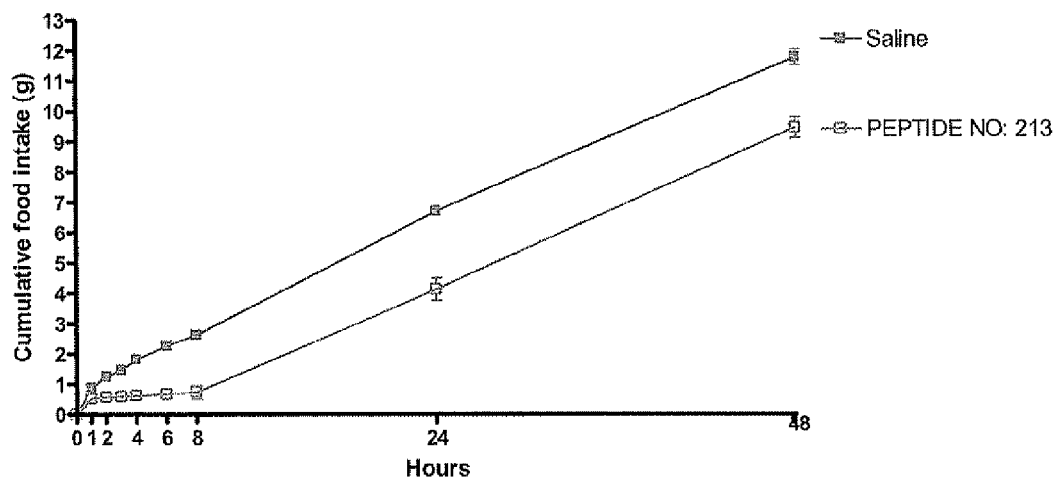
Figure 29:
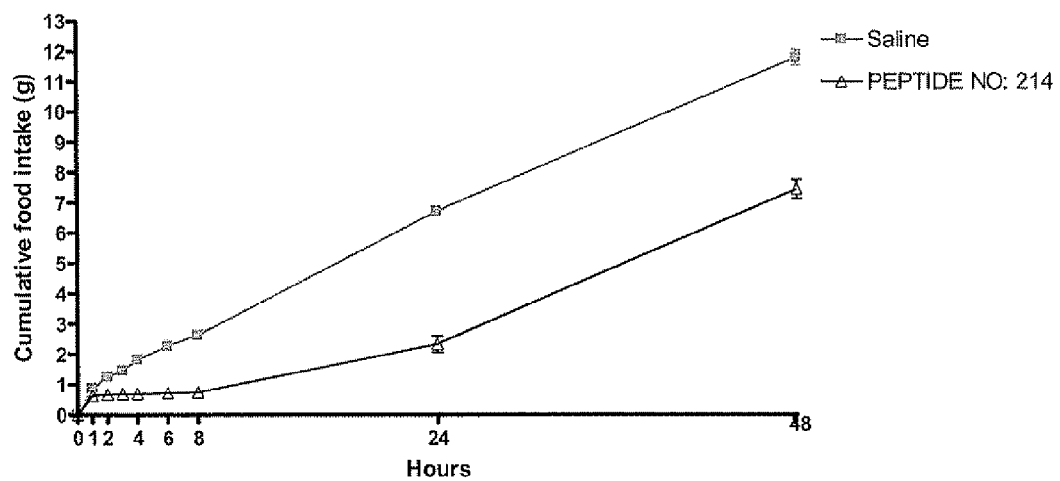
Figure 30:
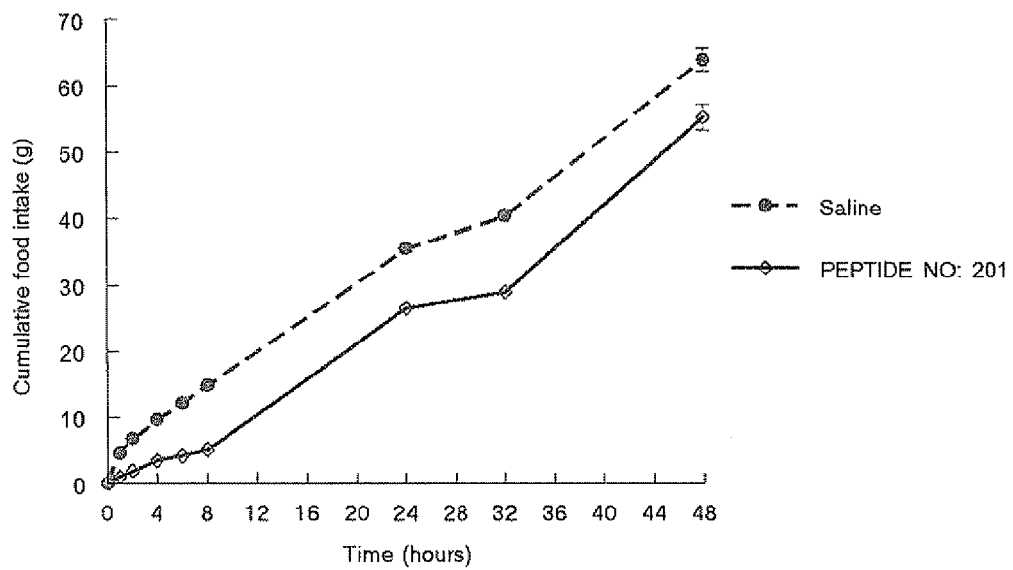

FIG. 1 discloses 355 specific peptide sequences falling within the scope of the invention.
FIGS. 2 to 41 show the results of Examples 1 to 19.
FIG. 2 relates to Example 1.
FIG. 3 relates to Example 2.
FIG. 4 relates to Example 3 (PEPTIDE NO: 94).
FIG. 5 relates to Example 3 (PEPTIDE NO: 82).
FIG. 6 relates to Example 3 (PEPTIDE NO: 58).
FIG. 7 relates to Example 3 (PEPTIDE NO: 52).
FIG. 8 relates to Example 4 (PEPTIDE NO: 164).
FIG. 9 relates to Example 4 (PEPTIDE NO: 167).
FIG. 10 relates to Example 5 (PEPTIDE NO: 100).
FIG. 11 relates to Example 5 (PEPTIDE NO: 148).
FIG. 12 relates to Example 6 (PEPTIDE NO: 60).
FIG. 13 relates to Example 6 (PEPTIDE NO: 178).
FIG. 14 relates to Example 7 (PEPTIDE NO: 155).
FIG. 15 relates to Example 8 (PEPTIDE NO: 142).
FIG. 16 relates to Example 8 (PEPTIDE NO: 172).
FIG. 17 relates to Example 8 (PEPTIDE NO. 184).
FIG. 18 relates to Example 9 (PEPTIDE NO: 4).
FIG. 19 relates to Example 9 (PEPTIDE NO: 108).
FIG. 20 relates to Example 9 (PEPTIDE NO: 195).
FIG. 21 relates to Example 9 (PEPTIDE NO: 136).
FIG. 22 relates to Example 10 (PEPTIDE NO: 142).
FIG. 23 relates to Example 10 (PEPTIDE NO: 22).
FIG. 24 relates to Example 10 (PEPTIDE NO: 153).
FIG. 25 relates to Example 10 (PEPTIDE NO: 199).
FIG. 26 relates to Example 11 (PEPTIDE NO: 210).
FIG. 27 relates to Example 11 (PEPTIDE NO. 211).
FIG. 28 relates to Example 11 (PEPTIDE NO: 213).
FIG. 29 relates to Example 11 (PEPTIDE NO: 214).
FIG. 30 relates to Example 12 (PEPTIDE NO: 201).

Figure 31:
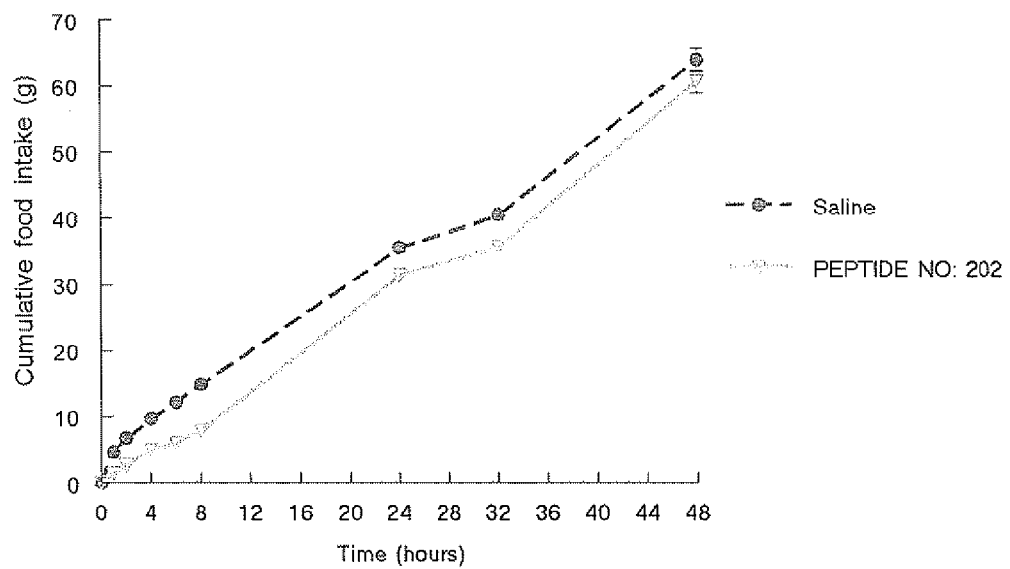
Figure 32:
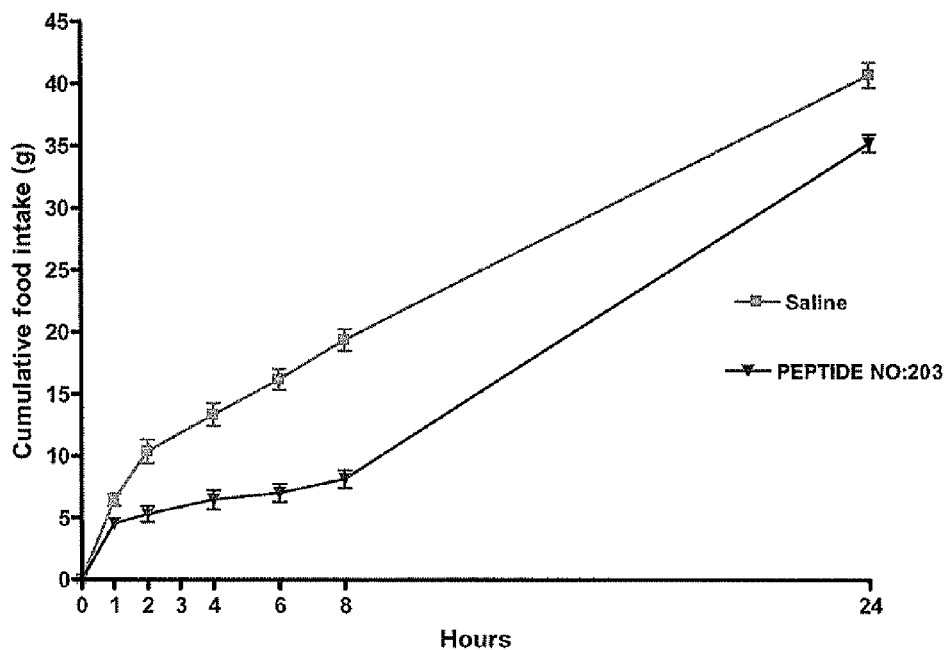
Figure 33:
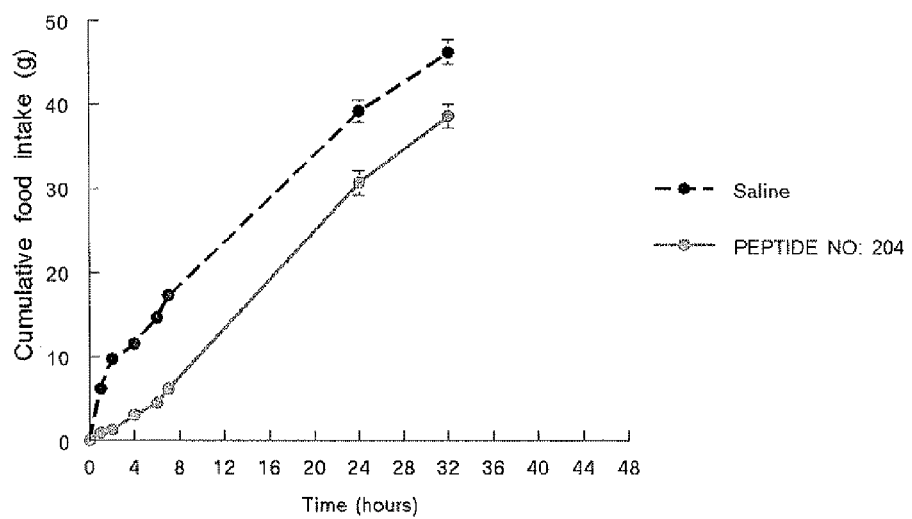
Figure 34:
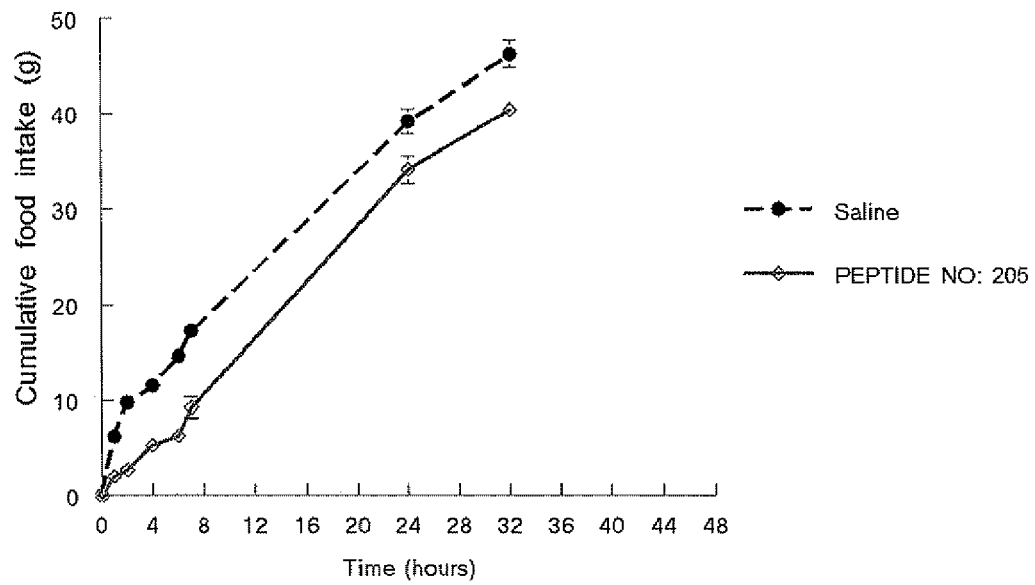
Figure 35:
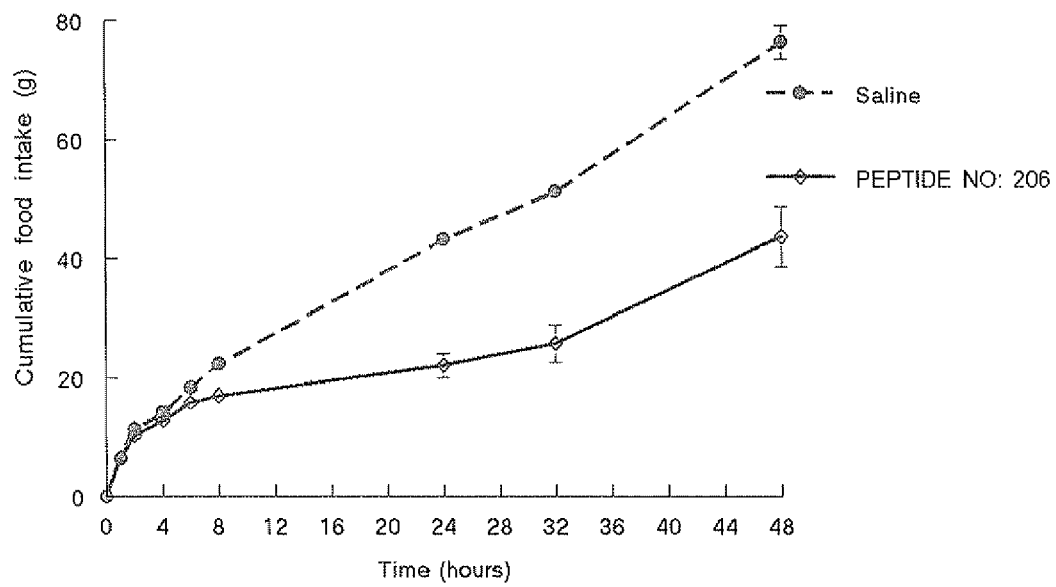
Figure 36:
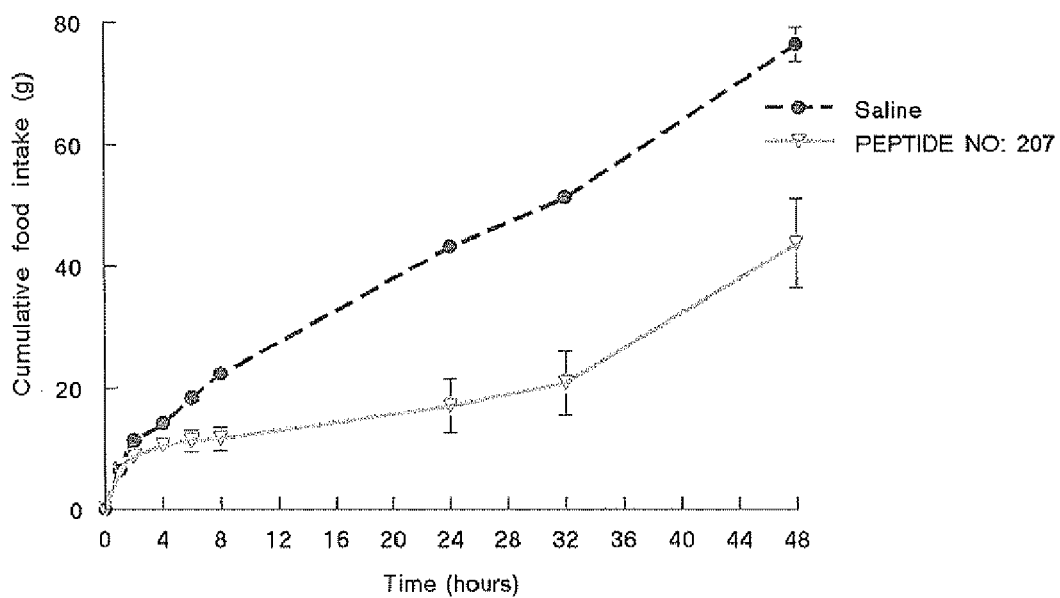
Figure 37:
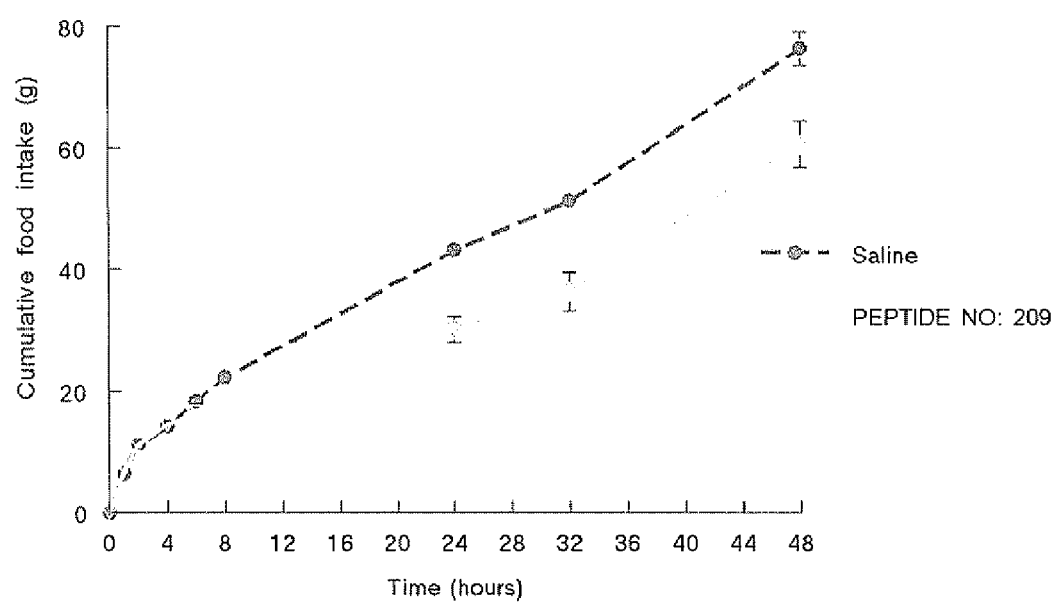
Figure 38:
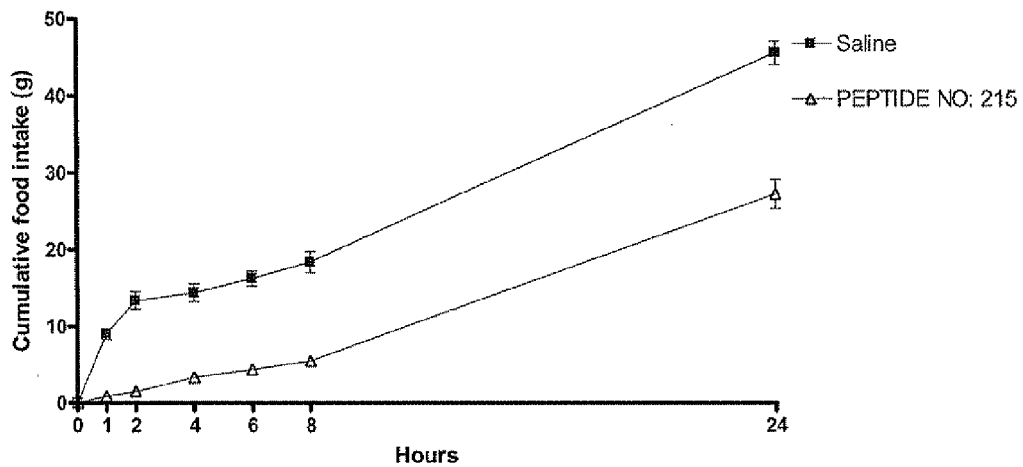
Figure 39:
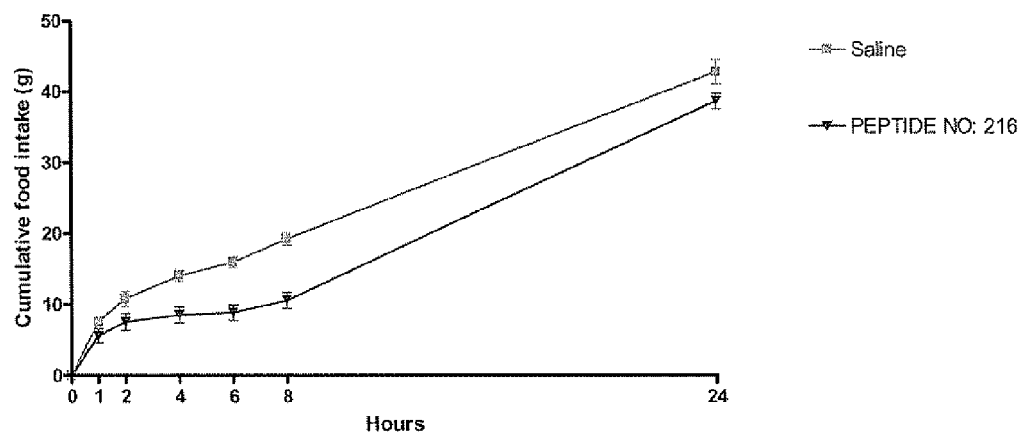
Figure 40:
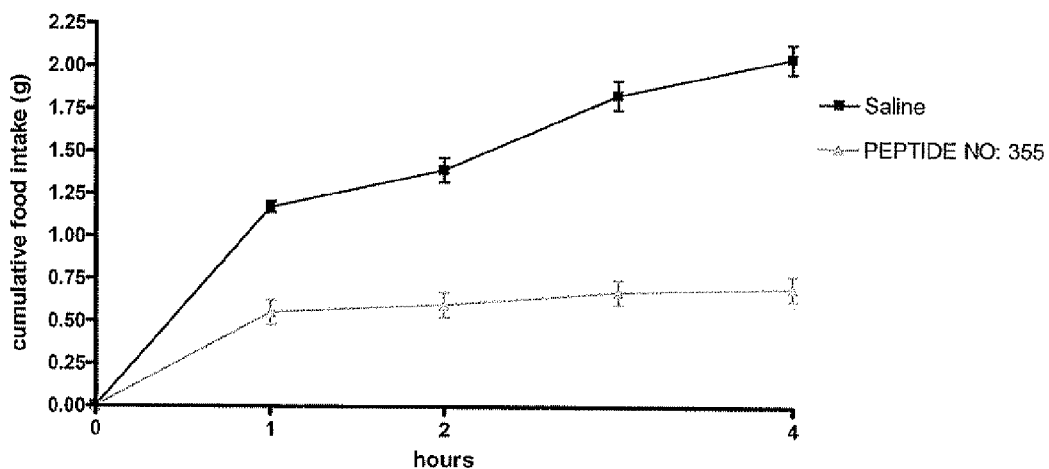
Figure 41:
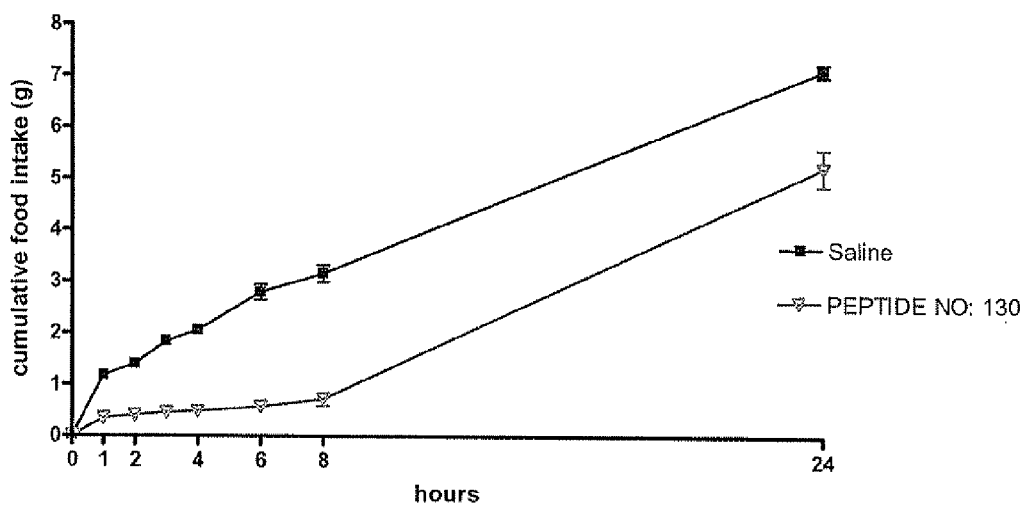

FIG. 31 relates to Example 12 (PEPTIDE NO: 202).
FIG. 32 relates to Example 13 (PEPTIDE NO: 203).
FIG. 33 relates to Example 14 (PEPTIDE NO: 204).
FIG. 34 relates to Example 14 (PEPTIDE NO: 205).
FIG. 35 relates to Example 15 (PEPTIDE NO: 206).
FIG. 36 relates to Example 15 (PEPTIDE NO. 207).
FIG. 37 relates to Example 15 (PEPTIDE NO: 209).
FIG. 38 relates to Example 16 (PEPTIDE NO: 215).
FIG. 39 relates to Example 17 (PEPTIDE NO: 216).
FIG. 40 relates to Example 18 (PEPTIDE NO: 355).
FIG. 41 relates to Example 19 (PEPTIDE NO: 130).

5. DEFINITIONS

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and non-human subjects, including veterinary subjects.

Appetite: A natural desire, or longing for food. In one embodiment, appetite is measured by a survey to assess the desire for food. Increased appetite generally leads to increased feeding behavior.

Appetite Suppressants Compounds that decrease the desire for food. Commercially available appetite suppressants include, but are not limited to, amfepramone (diethylpropion), phentermine, mazindol and phenylpropanolamine fenfluramine, dexfenfluramine, sibutramine, rimonabant and fluoxetine.

Body Mass Index (BMI): A mathematical formula for measuring body mass, also sometimes called Quetelet's Index. BMI is calculated by dividing weight (in kg) by height$^2$ (in meters$^2$). The recommended classifications for BMI in humans, adopted by the Expert Panel on the Identification, Evaluation and Treatment of Overweight and Obesity in Adults, and endorsed by leading organizations of health professionals, are as follows: Underweight <18.5 kg/m$^2$; Normal weight 18.5-24.9 kg/m$^2$; Overweight 25-29.9 kg/m$^2$; Obesity (Class 1) 30-34.9 kg/m$^2$; Obesity (Class 2) 35-39.9 kg/m$^2$; Extreme obesity (Class 3)>40 kg/m$^2$ (Practical Guide to the Identification, Evaluation, and Treatment of Overweight and Obesity in Adults, The North American Association for the Study of Obesity (NAASO) and the National Heart, Lung, and Blood Institute (NHLBI) 2000). In one embodiment, a BMI of greater than 25 kg/m$^2$ can be used to identify a subject in need of a treatment for excess weight or obesity. Ideal body weight will vary among species and individuals based on height, body build, bone structure, and sex.

Conservative substitutions: The replacement of an amino acid residue by another similar residue in a polypeptide. Typical but not limiting conservative substitutions are the replacements, for one another, among the aliphatic amino acids Ala, Val, Leu and Ile; interchange of Ser and Thr containing hydroxy residues, interchange of the acidic residues Asp and Glu, interchange between the amide-containing residues Asn and Gln, interchange of the basic residues Lys and Arg, interchange of the aromatic residues Phe and Tyr, and interchange of the small-sized amino acids Ala, Ser, Thr, Met and Gly. Additional conservative substitutions include the replacement of an amino acid by another of similar spatial or steric configuration, for example the interchange of Asn for Asp, or Gln for Glu.

TABLE 1

Non-limiting examples of conservative amino acid substitutions

| Original Residue | Conservative Substitutions |
|---|---|
| Ala | Gly, Val, Leu, Ile, Ser, Thr, Met |
| Arg | Lys |
| Asn | Asp, Gln, His |
| Asp | Glu, Asn |
| Cys | Ser |
| Gln | Asn, His, Lys, Glu |
| Glu | Asp, Gln |
| Gly | Ala, Ser, Thr, Met |
| His | Asn, Gln |
| Ile | Ala, Leu, Val, Met |
| Leu | Ala, Ile, Val, Met, |
| Lys | Arg |
| Met | Leu, Ile, Ala, Ser, Thr, Gly |
| Phe | Leu, Tyr, Trp |
| Ser | Thr, Cys, Ala, Met, Gly |
| Thr | Ser, Ala, Ser, Met, Gly |
| Trp | Tyr, Phe |
| Tyr | Trp; Phe |
| Val | Ala, Ile, Leu |

Non-conservative substitutions: The replacement, in a polypeptide, of an amino acid residue by another residue which is not biologically similar. For example, the replacement of an amino acid residue with another residue that has a substantially different charge, a substantially different hydrophobicity or a substantially different spatial or steric configuration.

The phrase "alternative amino acid" encompasses alternative amino acids that are the result of both conservative and non-conservative substitutions. In addition to the twenty commonly occurring amino acids that are typically found in naturally occurring polypeptides, rare amino acids, for example, canavanine, ornithine and 5-hydroxytryptophane, and artificial amino acids, that is to say amino acids not normally found in vivo, for example t-butylglycine, may be used as "alternative amino acids" in accordance with the invention. Any chiral form of an amino acid may be used.

Diabetes: A failure of cells to transport endogenous glucose across their membranes either because of an endogenous deficiency of insulin and/or a defect in insulin sensitivity. Diabetes is a chronic syndrome of impaired carbohydrate, protein, and fat metabolism owing to insufficient secretion of insulin or to target tissue insulin resistance. It occurs in two major forms: insulin-dependent diabetes mellitus (IDDM, type I) and non-insulin dependent diabetes mellitus (NIDDM, type II) which differ in etiology, pathology, genetics, age of onset, and treatment.

The two major forms of diabetes are both characterised by an inability to deliver insulin in an amount and with the precise timing that is needed for control of glucose homeostasis. Diabetes type I, or insulin dependent diabetes mellitus (IDDM) is caused by the destruction of pancreatic β cells, which results in insufficient levels of endogenous insulin. Diabetes type II, or non-insulin dependent diabetes, results from a defect in both the body's sensitivity to insulin, and a relative deficiency in insulin production.

Food intake: The amount of food consumed by an individual subject. Food intake can be measured by volume or by weight. For example, food intake may be the total amount of food consumed by an individual subject. Or, food intake may be the amount of proteins, fat, carbohydrates, cholesterol, vitamins, minerals, or any other food component, of the individual subject. "Protein intake" refers to the amount of protein consumed by an individual. Similarly, "fat intake," "carbohydrate intake," "cholesterol intake," "vitamin intake," and "mineral intake" refer to the amount of fat, carbohydrates, cholesterol, vitamins, or minerals consumed by an individual subject respectively.

Normal Daily Diet: The average food intake for an individual of a given species. A normal daily diet can be expressed in terms of caloric intake, protein intake, carbohydrate intake, and/or fat intake. A normal daily diet in humans generally comprises the following: about 2,000, about 2,400, or about 2,800 to significantly more calories. In addition, a normal daily diet in humans generally includes about 12 g to about 45 g of protein, about 120 g to about 610 g of carbohydrate, and about 11 g to about 90 g of fat. A low calorie diet would be no more than about 85%, and preferably no more than about 70%, of the normal caloric intake of a human individual.

In animals, the caloric and nutrient requirements vary depending on the species and size of the animal. For example, in cats, the total caloric intake per pound, as well as the percent distribution of protein, carbohydrate and fat varies with the age of the cat and the reproductive state. A general guideline for cats, however, is 40 cal/kg/day (18.2 cal/kg/day). About 30% to about 40% should be protein, about 7% to about 10% should be from carbohydrate, and about 50% to about 62.5% should be derived from fat intake, One of skill in the art can readily identify the normal daily diet of an individual of any species.

Obesity: A condition in which excess body fat may put a person at health risk (see Barlow and Dietz, *Pediatrics* 102: E29, 1998; National Institutes of Health, National Heart, Lung, and Blood Institute (NHLBI), *Obes. Res.* 6 (suppl. 2):51 S-209S, 1998). Excess body fat is a result of an imbalance of energy intake and energy expenditure. For example, the Body Mass Index (BMI) may be used to assess obesity. In one commonly used convention, a BMI of 25.0 kg/m$^2$ to 29.9 kg/m$^2$ is overweight, while a BMI of 30 kg/m$^2$ or greater is obese.

In another convention, waist circumference is used to assess obesity. Excess abdominal fat is an important, independent assessment of the risks associated with obesity or being overweight. Waist circumference measurement is particularly useful in patients who are categorised as normal or overweight. It is not usually necessary to measure waist circumference in individuals with BMIs≧35 kg/m$^2$ since it adds little to the predictive power of the disease risk classification of BMI. Men who have waist circumferences greater than 40 inches (102 cm), and women who have waist circumferences greater than 35 inches (90 cm), are at higher risk of diabetes, dyslipidemia, hypertension, and cardiovascular disease because of excess abdominal fat. Individuals with waist circumferences greater than these values should be considered one risk category above that defined by their BMI.

Strong evidence shows that obesity affects both the morbidity and mortality of individuals. For example, an overweight or obese individual is at increased risk for heart disease, non-insulin dependent (type 2) diabetes, hypertension, stroke, cancer (e.g. endometrial, breast, prostate, and colon cancer), dyslipidemia, gall bladder disease, sleep apnea, reduced fertility, and osteoarthritis, amongst others (see Lyznicki et al. *Am. Fam. Phys.* 63:2185, 2001).

Overweight: An individual who weighs more than their ideal body weight. An overweight individual can be obese, but is not necessarily obese. For example, an overweight individual is any individual who desires to decrease their weight. In one convention, an overweight individual is an individual with a BMI of 25.0 kg/m$^2$ to 29.9 kg/m$^2$.

Pegylation: the process of reacting a poly(alkylene glycol), preferably an activated poly(alkylene glycol) to form a covalent bond. A facilitator may be used, for example an amino acid, e.g. lysine. Although "pegylation" is often carried out using poly(ethylene glycol) or derivatives thereof, such as methoxy poly(ethylene glycol), the term is not limited herein to the use of methoxy poly(ethylene glycol) but also includes the use of any other useful poly(alkylene glycol), for example poly(propylene glycol). Pegylated shall be defined accordingly.

Peripheral Administration: Administration outside of the central nervous system. Peripheral administration does not include direct administration to the brain. Peripheral administration includes, but is not limited to intravascular, intramuscular, subcutaneous, inhalation, oral, rectal, transdermal, buccal, sub-lingual or intra-nasal administration Polypeptide: A polymer in which the monomers are amino acid residues which are joined together through amide bonds. When the amino acids are alpha-amino acids, either the L-optical isomer or the D-optical isomer can be used, the L-isomers being preferred. Throughout this specification, an alpha-amino acid will be assumed to be the L-isomer if it not explicitly stated to be the D-isomer. The terms "polypeptide" or "protein" as used herein encompass any amino acid sequence and include modified sequences such as glycoproteins. The term "polypeptide" covers naturally occurring proteins, as well as those which are recombinantly or synthetically produced. The term "polypeptide fragment" refers to a portion of a polypeptide, for example such a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest is fused to another peptide(s).

Therapeutically effective amount: A dose sufficient to prevent advancement, or to cause regression of a disorder, or which is capable of relieving a sign or symptom of a disorder, or which is capable of achieving a desired result. In several embodiments, a therapeutically effective amount of a compound of the invention is an amount sufficient to inhibit or halt weight gain, or an amount sufficient to decrease appetite, or an amount sufficient to reduce caloric intake or food intake or increase energy expenditure, or an amount sufficient to reduce weight, or to reduce the risk of mortality or morbidity from conditions associated with the disorder.

6. DETAILED DESCRIPTION

The inventors have found that, surprisingly, oxm analogues of the invention are effective appetite suppressants and/or have a more sustained effect than native oxm on food intake, and/or have a more potent effect than native oxm on food intake.

The human oxm sequence (which is the same as the rat and hamster) is as follows:

```
                                       (SEQ ID NO: 357)
His Ser Gln Gly Thr Phe Thr Ser Asp Tyr Ser Lys

Tyr Leu Asp Ser Arg Arg Ala Gln Asp Phe Val Gln

Trp Leu Met Asn Thr Lys Arg Asn Arg Asn Asn Ile

Ala
```

The peptides of the invention also have a longer half-life or clearance time or improved resistance to degradation as compared with oxm. Increased duration of appetite suppression can be particularly important to avoid the effect known as "escape". A short duration appetite suppressant may reduce appetite for the time covered by one meal and, in that meal, the subject typically eats less food. It however, the appetite suppressant has a short half-life or rapid clearance time or is then metabolized or otherwise removed from the circulation of the subject, then by the time of the next mealtime, the subject can regain its "normal" appetite. In view of the subject having eaten a small meal at the previous mealtime, the subject may in fact have an increased appetite by the time of the subsequent meal. If the subject satisfies that appetite, it is possible for the food intake over the two meals, in total, to be no lower than the food intake would have been without the appetite suppressant. That is to say that the subject may have "escaped" from the effects of the appetite suppressant. "Escape" can be reduced by using additional doses of appetite suppressant, or by using an appetite suppressant with a longer duration of action. If the subject has a reduced appetite for longer, then the degree to which it can make up the missed food from one meal in the next meal is reduced as there is a practical limit to the total capacity for food in a particular meal. Repeated or continuous administration of a compound over a period of time, for example over a period of days or weeks, will lead to extended appetite suppression and reduced potential for escape from the effects of the appetite suppression.

The improved activity and/or duration of action of the oxm analogues as compared with oxm offers various advantages. For example, effective suppression of appetite at lower dosages will be permitted (with the lower dosage and/or lower peak levels, offering the prospect of reduced side effects (including nausea) and reduction in the cost of treatment), or usage at relatively high dosages will be better tolerated by the patient enabling quicker and/or greater weight loss. Certain of the compounds of the invention used in the Examples herein exhibit a pattern of appetite suppression indicative of a 'flatter blood curve', that is to say they have improved pharmacokinetids, by virtue of displaying either or both of (i) a more gradual onset of the appetite suppressant activity than oxm and thereby potentially avoid an initial sharp peak (which may be associated with nausea); and (ii) a potentially longer duration of action.

Further advantages of many compounds of the invention include that the compounds have improved storage characteristics and are amenable to large scale synthesis, for example some compounds of the invention do not contain sequence motifs associated with the formation of aspartimide species, and/or are less prone to reduced stability.

In one embodiment, the invention provides a peptide wherein

```
Xaa15 Xaa16 Xaa17 Xaa18 Xaa19 Xaa20 Xaa21 Xaa22 Xaa23 Xaa24 is:   (SEQ ID NO: 359)

Glu15 Glu16 Glu17 Leu18 Val19 Lys20 Tyr21 Phe22 Leu23 Glu24,

Glu15 Glu16 Glu17 Leu18 Val19 Lys20 Tyr21 Phe22 Leu23 Gln24,

Glu15 Glu16 Glu17 Leu18 Val19 Lys20 Tyr21 Phe22 Ile23 Glu24,

Glu15 Glu16 Glu17 Leu18 Val19 Lys20 Tyr21 Phe22 Ile23 Gln24,

Glu15 Glu16 Glu17 Ile18 Val19 Lys20 Tyr21 Phe22 Leu23 Glu24,

Glu15 Glu16 Glu17 Ile18 Val19 Lys20 Tyr21 Phe22 Leu23 Gln24,

Glu15 Glu16 Glu17 Ile18 Val19 Lys20 Tyr21 Phe22 Ile23 Glu24,

Glu15 Glu16 Glu17 Ile18 Val19 Lys20 Tyr21 Phe22 Ile23 Gln24,

Glu15 Gln16 Glu17 Leu18 Val19 Lys20 Tyr21 Phe22 Leu23 Glu24,

Glu15 Gln16 Glu17 Leu18 Val19 Lys20 Tyr21 Phe22 Leu23 Gln24,

Glu15 Gln16 Glu17 Leu18 Val19 Lys20 Tyr21 Phe22 Ile23 Glu24,

Glu15 Gln16 Glu17 Leu18 Val19 Lys20 Tyr21 Phe22 Ile23 Gln24,

Glu15 Gln16 Glu17 Ile18 Val19 Lys20 Tyr21 Phe22 Leu23 Glu24,

Glu15 Gln16 Glu17 Ile18 Val19 Lys20 Tyr21 Phe22 Leu23 Gln24,

Glu15 Gln16 Glu17 Ile18 Val19 Lys20 Tyr21 Phe22 Ile23 Glu24,
or

Glu15 Gln16 Glu17 Ile18 Val19 Lys20 Tyr21 Phe22 Ile23 Gln24.
```

In particular embodiments, a peptide of the invention is one wherein

```
Xaa15 Xaa16 Xaa17 Xaa18 Xaa19 Xaa20 Xaa21 Xaa22 Xaa23 Xaa24 is:

Glu15 Gln16 Glu17 Ile18 Val19 Lys20 Tyr21 Phe22 Ile23 Gln24,

Glu15 Glu16 Glu17 Ile18 Val19 Lys20 Tyr21 Phe22 Ile23 Gln24,

Glu15 Gln16 Glu17 Leu18 Val19 Lys20 Tyr21 Phe22 Ile23 Gln24,

Glu15 Glu16 Glu17 Leu18 Val19 Lys20 Tyr21 Phe22 Ile23 Gln24,
```

-continued

```
Glu15 Gln16 Glu17 Ile18 Val19 Lys20 Tyr21 Phe22 Leu23 Gln24,
or

Glu15 Glu16 Glu17 Leu18 Val19 Lys20 Tyr21 Phe22 Leu23 Gln24.
```

In a further embodiment, a peptide of the invention is one wherein

```
Xaa15 Xaa16 Xaa17 Xaa18 Xaa19 Xaa20 Xaa21 Xaa22 Xaa23 Xaa24 is:

Asp15 Ser16 Arg17 Arg18 Ala19 Gln20 Asp21 Phe22 Val23 Gln24.
```

In a further embodiment, a peptide of the invention comprises Xaa1 Xaa2 Xaa3 selected from the group consisting of:

```
    His1 Ser2 Gln3,          (SEQ ID NO: 360)

D-His1 Ser2 Gln3,

D-His1 Ala2 Gln3,
and

D-His1 Ala2 Asp3.
```

In a further embodiment, a peptide of the invention is one wherein

```
    Xaa27 Xaa28 Xaa29 Xaa30 Xaa31 Xaa32 is:

Lys27 Asn28 Ala29 Gly30 Pro31 Ser32,

Lys27 Asn28 Gly29 Gly30 Pro31 Ser32,
or

Met27 Asn28 Thr29 Lys30 Arg31 Asn32.
```

In a further embodiment, a peptide of the invention is one wherein

```
                                         (SEQ ID NO: 361)
    Xaa27 Xaa28 Xaa29 Xaa30 Xaa31 Xaa32 is:

Lys27 Asn28 Ala29 Gly30 Pro31 Ser32,
or

Lys27 Asn28 Gly29 Gly30 Pro31 Ser32.
```

In one embodiment, a peptide of the invention is one wherein

```
    Xaa27 Xaa28 Xaa29 Xaa30 Xaa31 Xaa32 is:

Lys27 Asn28 Ala29 Gly30 Pro31 Ser32.
```

In particular, the peptide of the invention may have an amino acid sequence selected from the group comprising:

```
His Ser Gln Gly Thr Phe Thr Ser Asp Tyr Ser Lys Tyr Leu Glu Glu Glu Leu Val Lys    (SEQ ID NO: 1)
Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 2)
Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 3)
Tyr Phe Leu Glu Trp Leu Met Asn Thr Lys Arg Asn Lys Asn Ile Ala

His Ser Gln Gly Thr Phe Thr Ser Asp Tyr Ser Lys Tyr Leu Glu Glu Glu Leu Val Lys    (SEQ ID NO: 4)
Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 5)
Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 6)
Tyr Phe Leu Gln Trp Leu Met Asn Thr Lys Arg Asn Lys Asn Ile Ala

His Ser Gln Gly Thr Phe Thr Ser Asp Tyr Ser Lys Tyr Leu Glu Glu Glu Leu Val Lys    (SEQ ID NO: 7)
Tyr Phe Ile Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 8)
Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 9)
Tyr Phe Ile Glu Trp Leu Met Asn Thr Lys Arg Asn Lys Asn Ile Ala

His Ser Gln Gly Thr Phe Thr Ser Asp Tyr Ser Lys Tyr Leu Glu Glu Glu Leu Val Lys    (SEQ ID NO: 10)
Tyr Phe Ile Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 11)
Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val Lys    (SEQ ID NO: 12)
Tyr Phe Ile Gln Trp Leu Met Asn Thr Lys Arg Asn Lys Asn Ile Ala
```

-continued

```
His Ser Gln Gly Thr Phe Thr Ser Asp Tyr Ser Lys Tyr Leu Glu Glu Glu Ile Val Lys     (SEQ ID NO: 13)
Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 14)
Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 15)
Tyr Phe Leu Glu Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Ile Val Lys     (SEQ ID NO: 16)
Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 17)
Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 18)
Tyr Phe Leu Gln Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Ile Val Lys     (SEQ ID NO: 19)
Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 20)
Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 21)
Tyr Phe Ile Glu Tap Leu Met Asn Thr Lys Arg Asn Lys Asn Asn Ile Ala

His Ser Gln Gly Thr Phe Thr Ser Asp Tyr Ser Lys Tyr Leu Glu Glu Glu Ile Val Lys     (SEQ ID NO: 22)
Tyr Phe ILe Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 23)
Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 24)
Tyr Phe Ile Gln Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val Lys     (SEQ ID NO: 25)
Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 26)
Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 27)
Tyr Phe Leu Glu Trp Leu Met Asn Thr Lys Arg Asn Lys Asn Asn Ile Ala

HisSer Gln Gly Thr Phe Thr Ser Asp Tyr Ser Lys Tyr Leu Glu Gln Glu Leu Val Lys      (SEQ ID NO: 28)
Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 29)
Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 30)
Tyr Phe Leu Gln Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val Lys     (SEQ ID NO: 31)
Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 32)
Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 33)
Tyr Phe Ile Glu Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val Lys     (SEQ ID NO: 34)
Tyr Phe Ile Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 35)
Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val Lys     (SEQ ID NO: 36)
Tyr Phe Ile Gln Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Ile Val Lys     (SEQ ID NO: 37)
Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 38)
Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 39)
Tyr Phe Leu Glu Trp Leu Met Asn Thr Lys Arg Asn Lys Asn Asn Ile Ala
```

-continued

His Ser Gln Gly Thr Phe Thr Ser Asp Tyr Ser Lys Tyr Leu Glu Gln Glu Ile Val Lys  (SEQ ID NO: 40)
Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys  (SEQ ID NO: 41)
Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys  (SEQ ID NO: 42)
Tyr Phe Leu Gln Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Ile Val Lys  (SEQ ID NO: 43)
Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys  (SEQ ID NO: 44)
Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys  (SEQ ID NO: 45)
Tyr Phe Ile Glu Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Ile Val Lys  (SEQ ID NO: 46)
Tyr Phe Ile Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys  (SEQ ID NO: 47)
Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys  (SEQ ID NO: 48)
Tyr Phe Ile Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val  (SEQ ID NO: 49)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 50)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 51)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val  (SEQ ID NO: 52)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 53)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 54)
Lys Tyr Phe Leu Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val  (SEQ ID NO: 55)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 56)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 57)
Lys Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val  (SEQ ID NO: 58)
Lys Tyr Phe Ile Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 59)
Lys Tyr Phe Ile Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val  (SEQ ID NO: 60)
Lys Tyr Phe Ile Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Ile Val  (SEQ ID NO: 61)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val  (SEQ ID NO: 62)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val  (SEQ ID NO: 63)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Ile Val  (SEQ ID NO: 64)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val  (SEQ ID NO: 65)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val  (SEQ ID NO: 66)
Lys Tyr Phe Leu Gln Trp Leu Met Asn Thr Lys Arg Asn Lys Asn Asn Ile Ala

-continued

```
D-His Ser Gln Gly Thr Phe Thr Ser Asp Tyr Ser Lys Tyr Leu Glu Glu Glu Ile Val        (SEQ ID NO: 67)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val        (SEQ ID NO: 68)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val        (SEQ ID NO: 69)
Lys Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Ile Val        (SEQ ID NO: 70)
Lys Tyr Phe Ile Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val        (SEQ ID NO: 71)
Lys Tyr Phe Ile Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val        (SEQ ID NO: 72)
Lys Tyr Phe Ile Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val        (SEQ ID NO: 73)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 74)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 75)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val        (SEQ ID NO: 76)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 77)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 78)
Lys Tyr Phe Leu Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val        (SEQ ID NO: 79)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 80)
Lys Tyr Phe Ile Glu Trp Leu Lys Asn Gly Gly Pro Ser Lys Aen Asn Ile Ala

D-His Ser Gln Gly Thr Phe Thr Ser Asp Tyr Ser Lys Tyr Leu Glu Gln Glu Leu Val        (SEQ ID NO: 81)
Lys Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val        (SEQ ID NO: 82)
Lys Tyr Phe Ile Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 83)
Lys Tyr Phe Ile Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val        (SEQ ID NO: 84)
Lys Tyr Phe Ile Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Ile Val        (SEQ ID NO: 85)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val        (SEQ ID NO: 86)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val        (SEQ ID NO: 87)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Ile Val        (SEQ ID NO: 88)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val        (SEQ ID NO: 89)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val        (SEQ ID NO: 90)
Lys Tyr Phe Leu Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Ile Val        (SEQ ID NO: 91)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val        (SEQ ID NO: 92)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val        (SEQ ID NO: 93)
Lys Tyr Phe Ile Glu Trp Leu Met Asn Thr Lys Arg Asn Lys Asn Asn Ile Ala
```

-continued

```
D-His Ser Gln Gly Thr Phe Thr Ser Asp Tyr Ser Lys Tyr Leu Glu Gln Glu Ile Val      (SEQ ID NO: 94)
Lys Tyr Phe Ile Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val      (SEQ ID NO: 95)
Lys Tyr Phe Ile Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val      (SEQ ID NO: 96)
Lys Tyr Phe Ile Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Glu Leu Val      (SEQ ID NO: 97)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Glu Leu Val      (SEQ ID NO: 98)
Lys Tyr Phe Leu Glu Trp Leu Lys Asn Gly Gly Pro Ser Lys Asn Asa Asn Ile Ala

D-His Ala Gln Gly Thr Phe Thr Ser Asp Tyr Ser Lys Tyr Leu Glu Glu Glu Leu Val      (SEQ ID NO: 99)
Lys Tyr Phe Leu Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Glu Leu Val      (SEQ ID NO: 100)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Glu Leu Val      (SEQ ID NO: 101)
Lys Tyr Phe Leu Gln Trp Leu Lys Asn Gly Gly Pro Ser Lys Asn Asn Ile Ala

D-His Ala Gln Sly Thr Phe Thr Ser Asp Tyr Ser Lys Tyr Leu Glu Glu Glu Leu Val      (SEQ ID NO: 102)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Glu Leu Val      (SEQ ID NO: 103)
Lys Tyr Phe Ile glu Trp Leu Lys Asn Ala Gly Pro Ser Lys Asn Asn Ile Ala D-His Ala Gln Gly Thr Phe Thr Ser Asp Tyr Ser Lys Tyr Leu Glu Glu Glu Leu Val      (SEQ ID NO: 104)
Lys Tyr Phe Ile Glu Trp Leu Lys Asn Gly Gly Pro Ser Lys Asn Asn Ile Ala D-His Ala Gln Gly Thr Phe Thr Ser Asp Tyr Ser Lys Tyr Leu Glu Glu Glu Leu Val      (SEQ ID NO: 105)
Lys Tyr Phe Ile Glu Trp Leu Met Asn Thr Lys Arg Asn Lys Asn Asn Ile Ala D-His Ala Gln Gly Thr Phe Thr Ser Asp Tyr Ser Lys Tyr Leu Glu Glu Glu Leu Val      (SEQ ID NO: 106)
Lys Tyr Phe Ile Gln Trp Leu Lys Asn Ala Gly Pro Ser Lys Asn Asn Ile Ala D-His Ala Gln Gly Thr Phe Thr Ser Asp Tyr Ser Lys Tyr Leu Glu Glu Glu Leu Val      (SEQ ID NO: 107)
Lys Tyr Phe Ile Gln Trp Leu Lys Asn Gly Gly Pro Ser Lys Asn Asn Ile Ala D-His Ala Gln Gly Thr Phe Thr Ser Asp Tyr Ser Lys Tyr Leu glu Glu Glu Leu Val      (SEQ ID NO: 108)
Lys Tyr Phe Ile Gln Trp Leu Met Asn Thr Lys Arg Asn Lys Asn Asn Ile Ala D-His Ala Gln Gly Thr Phe Thr Ser Asp Tyr Ser Lys Tyr Leu Glu Glu Glu Ile Val      (SEQ ID NO: 109)
Lys Tyr Phe Leu Glu Trp Leu Lys Asn Ala Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 110)
Lys Tyr Phe Leu Glu Trp Leu Lys Asn Gly Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 111)
Lys Tyr Phe Leu Glu Trp Leu Met Asn Thr Lys Arg Asn Lys Asn Asn Ile Ala D-His Ala Gln Gly Thr Phe Thr Ser Asp Tyr Ser Lys Tyr Leu Glu Glu Glu Ile Val      (SEQ ID NO: 112)
Lys Tyr Phe Leu Gln Trp Leu Lys Asn Ala Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 113)
Lys Tyr Phe Leu Gln Trp Leu Lys Asn Gly Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 114)
Lys Tyr Phe Leu Gln Trp Leu Met Asn Thr Lys Arg Asn Lys Asn Asn Ile Ala D-His Ala Gln Gly Thr Phe Thr Ser Asp Tyr Ser Lys Tyr Leu Glu Glu Glu Ile Val      (SEQ ID NO: 115)
Lys Tyr Phe Ile Glu Trp Leu Lys Asn Ala Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 116)
Lys Tyr Phe Ile Glu Trp Leu Lys Asn Gly Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 117)
Lys Tyr Phe Ile Glu Trp Leu Met Asn Thr Lys Arg Asn Lys Asn Asn Ile Ala D-His Ala Gln Gly Thr Phe Thr Ser Asp Tyr Ser Lys Tyr Leu Glu Glu Glu Ile Val      (SEQ ID NO: 118)
Lys Tyr Phe Ile Gln Trp Leu Lys Asn Ala Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 119)
Lys Tyr Phe Ile Gln Trp Leu Lys Asn Gly Gly Pro Ser Lys Asn Asn Ile Ala D-His Ala Gln Gly Thr Phe Thr Ser Asp Tyr Ser Lys Tyr Leu Glu Glu Glu Ile Val      (SEQ ID NO: 120)
Lys Tyr Phe Ile Gln Trp Leu Met Asn Thr Lys Arg Asn Lys Asn Asn Ile Ala
```

-continued

```
D-His Ala Gln Gly Thr Phe Thr Ser Asp Tyr Ser Lys Tyr Leu Glu Gln Glu Leu Val     (SEQ ID NO: 121)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 122)
Lys Tyr Phe Leu Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 123)
Lys Tyr Phe Leu Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Leu Val     (SEQ ID NO: 124)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 125)
Lys Tyr Phe Leu Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 126)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Leu Val     (SEQ ID NO: 127)
Lys Tyr Phe Ile Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 128)
Lys Tyr Phe Ile Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 129)
Lys Tyr Phe Ile Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Leu Val     (SEQ ID NO: 130)
Lys Tyr Phe Ile Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 131)
Lys Tyr Phe Ile Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val     (SEQ ID NO: 132)
Lys Tyr Phe Ile Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val     (SEQ ID NO: 133)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 134)
Lys Tyr Phe Leu Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 135)
Lys Tyr Phe Leu Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val     (SEQ ID NO: 136)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 137)
Lys Tyr Phe Leu Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 138)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val     (SEQ ID NO: 139)
Lys Tyr Phe Ile Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 140)
Lys Tyr Phe Ile Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 141)
Lys Tyr Phe Ile Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val     (SEQ ID NO: 142)
Lys Tyr Phe Ile Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 143)
Lys Tyr Phe Ile Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val     (SEQ ID NO: 144)
Lys Tyr Phe Ile Gln Trp Leu Met Asn Thr Lys Avg Asn Lys Asn Asn Ile Ala

D-His Ala Asp Gly Thr Phe Thr Ser Asp Tyr Ser Lys Tyr Leu Glu Glu Glu Leu Val     (SEQ ID NO: 145)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val     (SEQ ID NO: 146)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val     (SEQ ID NO: 147)
Lys Tyr Phe Leu Glu Trp Leu Met Asn Thr Lys Arg Asn Lys Asn Asn Ile Ala
```

```
D-His Ala Asp Gly Thr Phe Thr Ser Asp Tyr Ser Lys Tyr Leu Glu Glu Glu Leu Val       (SEQ ID NO: 148)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val       (SEQ ID NO: 149)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val       (SEQ ID NO: 150)
Lys Tyr Phe Leu Gln Trp Leu Met Asn Thr Lys Arg Asn Lys Asn Asa Ile Ala

D-His Ala Asp Gly Thr Phe Thr Ser Asp Tyr Ser Lys Tyr Leu Glu Glu Glu Leu Val       (SEQ ID NO: 151)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val       (SEQ ID NO: 152)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val       (SEQ ID NO: 153)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Leu Val       (SEQ ID NO: 154)
Lys Tyr Phe Ile Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val       (SEQ ID NO: 155)
Lys Tyr Phe Ile Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val       (SEQ ID NO: 156)
Lys Tyr Phe Ile Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Leu Val       (SEQ ID NO: 157)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 158)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 159)
Lys Tyr Phe Leu Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Ile Val       (SEQ ID NO: 160)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 161)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 162)
Lys Tyr Phe Leu Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Ile Val       (SEQ ID NO: 163)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 164)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 165)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Ile Val       (SEQ ID NO: 166)
Lys Tyr Phe Ile Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 167)
Lys Tyr Phe Ile Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Ile Val       (SEQ ID NO: 168)
Lys Tyr Phe Ile Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Leu Val       (SEQ ID NO: 169)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val       (SEQ ID NO: 170)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val       (SEQ ID NO: 171)
Lys Tyr Phe Leu Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Leu Val       (SEQ ID NO: 172)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val       (SEQ ID NO: 173)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val       (SEQ ID NO: 174)
Lys Tyr Phe Leu Gln Trp Leu Met Asn Thr Lys Arg Asn Lys Asn Asn Ile Ala
```

```
D-His Ala Asp Gly Thr Phe Thr Ser Asp Tyr Ser Lys Tyr Leu Glu Gln Glu Leu Val      (SEQ ID NO: 175)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val      (SEQ ID NO: 176)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val      (SEQ ID NO: 177)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Leu Val      (SEQ ID NO: 178)
Lys Tyr Phe Ile Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val      (SEQ ID NO: 179)
Lys Tyr Phe Ile Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val      (SEQ ID NO: 180)
Lys Tyr Phe Ile Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val      (SEQ ID NO: 181)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 182)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 183)
Lys Tyr Phe Leu Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val      (SEQ ID NO: 184)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 185)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 186)
Lys Tyr Phe Leu Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val      (SEQ ID NO: 187)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 188)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 189)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val      (SEQ ID NO: 190)
Lys Tyr Phe Ile Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 191)
Lys Tyr Phe Ile Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val      (SEQ ID NO: 192)
Lys Tyr Phe Ile Gln Trp Leu Met Asn Thr Lys Arg Asn Lys Asn Asn Ile Ala
```

For example, the peptide of the invention may have the amino acid sequence

```
His Ser Gln Gly Thr Phe Thr Ser Asp Tyr Ser Lys Tyr Leu Asp Ser Arg Arg Ala Gln     (SEQ ID NO: 193)
Asp Phe Val Gln Trp Leu Lys Asn Ala Gly Pro Ser Lys Asn Asn Ile Ala

His Ser Gln Gly Thr Phe Thr Ser Asp Tyr Ser Lys Tyr Leu Asp Ser Arg Arg Ala Gln     (SEQ ID NO: 194)
Asp Phe Val Gln Trp Leu Lys Asn Gly Gly Pro Ser Lys Asn Asn Ile Ala

D-His Ser Gln Gly Thr Phe Thr Ser Asp Tyr Ser Lys Tyr Leu Asp Ser Arg Arg Ala       (SEQ ID NO: 195)
Gln Asp Phe Val Gln Trp Leu Lys Asn Ala Gly Pro Ser Lys Asn Asn Ile Ala

D-His Ser Gln Gly Thr Phe Thr Ser Asp Tyr Ser Lys Tyr Leu Asp Ser Arg Arg Ala       (SEQ ID NO: 196)
Gln Asp Phe Val Gln Trp Leu Lys Asn Gly Gly Pro Ser Lys Asn Asn Ile Ala

D-His Ala Gln Gly Trp Phe Trp Ser Asp Tyr Ser Lys Tyr Leu Asp Ser Arg Arg Ala       (SEQ ID NO: 197)
Gln Asp Phe Val Gln Trp Leu Lys Asn Ala Gly Pro Ser Lys Asn Asn Ile Ala

D-His Ala Gln Gly Thr Phe Thr Ser Asp Tyr Ser Lys Tyr Leu Asp Ser Arg Arg Ala       (SEQ ID NO: 198)
Gln Asp Phe Val Gln Trp Leu Lys Asn Gly Gly Pro Ser Lys Asn Asn Ile Ala

D-His Ala Asp Gly Trp Phe Trp Ser Asp Tyr Ser Lys Tyr Leu Asp Ser Arg Arg Ala       (SEQ ID NO: 199)
Gln Asp Phe Val Gln Trp Leu Lys Asn Ala Gly Pro Ser Lys Asn Asn Ile Ala
```

```
D-His Ala Asp Gly Thr Phe Thr Ser Asp Tyr Ser Lys Tyr Leu Asp Ser Arg Arg Ala     (SEQ ID NO: 200)
Gln Asp Phe Val Gln Trp Leu Lys Asn Gly Gly Pro Ser Lys Asn Asn Ile Ala
```

Optionally, the peptide of the invention has an extension moiety -A-B-C at the C-terminus. Accordingly, the peptide of the invention may have an additional extension moiety of sequence -A-B-C,
wherein:
  A is absent or 1, 2, 3 or 4 Ala residues or 1, 2, 3 or 4 Glu residues
  B is absent or 1, 2, 3 or 4 Ala residues or 1, 2, 3 or 4 Glu residues
provided that A and B do not both comprise Ala residues, and that A and B do not both comprise Glu residues; and
  C is Lys, or Lys with an acid selected from capric acid, lauric acid, myristic acid, palmitic acid, stearic acid and arachidic acid, attached via its —COOH group to the —NH$_2$ group of the Lys side chain by means of a peptide bond.

In one embodiment, groups A or B or both A and B are absent. In an embodiment when A and B are both present, A is Glu and B is Ala. For example, in one embodiment A is one Glu residue, and B is one Ala residue.

In one embodiment, C is a Lys residue without substitution.

In one embodiment, C is a Lys residue with a fatty acid attached via its COOH group to the —NH$_2$ group of the Lys side chain by means of a peptide bond. For example, the fatty acid may be selected from capric acid
lauric acid
myristic acid,
palmitic acid,
stearic acid, and
arachidic acid. (icosanoic acid)

In further embodiments, the C-terminal extension moiety -A-B-C is:
  Lys38,
  Lys38-caproyl
  Lys38-lauroyl,
  Lys38-myristoyl,
  Lys38-palmitoyl,
  Lys38-stearoyl,
  Lys38-arachidoyl,
  Glu38 Ala39 Lys40,
  Glu38 Ala39 Lys40-caproyl,
  Glu38 Ala39 Lys40-lauroyl,
  Glu38 Ala39 Lys40-myristoyl,
  Glu38 Ala39 Lys40-palmitoyl,
  Glu38 Ala39 Lys40-stearoyl,
or Glu38 Ala39 Lys40-arachidoyl.

The arachidoyl group is also known as the icosanoyl group.

Exemplary compounds comprising the C-terminal extension moiety -A-B-C may be selected from the group comprising:

```
D-His Ala Asp Gly Thr Phe Thr Ser Asp Tyr Ser Lys Tyr Leu Glu Glu Glu Ile Val     (SEQ ID NO: 201)
Lys Tyr Phe Ile Gln Trp Leu Lys Asn Gly Gly Pro Ser Lys Asn Asn Ile Ala Lys

D-His Ala Asp Gly Thr Phe Thr Ser Asp Tyr Ser Lys Tyr Leu Glu Gln Glu Ile Val     (SEQ ID NO: 202)
Lys Tyr Phe Ile Gln Trp Leu Lys Asn Gly Gly Pro Ser Lys Asn Asn Ile Ala Lys

D-His Ala Asp Gly Thr Phe Thr Ser Asp Tyr Ser Lys Tyr Leu Glu Glu Glu Ile Val     (SEQ ID NO: 203)
Lys Tyr Phe Ile Gln Trp Leu Met Asn Thr Lys Arg Asn Lys Asn Asn Ile Ala Lys

D-His Ala Asp Gly Thr Phe Thr Ser Asp Tyr Ser Lys Tyr Leu Glu Glu Glu Leu Val     (SEQ ID NO: 204)
Lys Tyr Phe Ile Gln Trp Leu Lys Asn Gly Gly Pro Ser Lys Asn Asn Ile Ala Lys

D-His Ala Asp Gly Thr Phe Thr Ser Asp Tyr Ser Lys Tyr Leu Glu Gln Glu Leu Val     (SEQ ID NO: 205)
Lys Tyr Phe Ile Gln Trp Leu Lys Asn Gly Gly Pro Ser Lys Asn Asn Ile Ala Lys

D-His Ala Asp Gly Thr Phe Thr Ser Asp Tyr Ser Lys Tyr Leu Glu Glu Glu Leu Val     (SEQ ID NO: 206)
Lys Tyr Phe Ile Gln Trp Leu Lys Asn Gly Gly Pro Ser Lys Asn Asn Ile Ala Ala Ala
Lys-myristoyl D-His Ala Asp Gly Thr Phe Thr Ser Asp Tyr Ser Lys Tyr Leu Glu Glu Glu Leu Val     (SEQ ID NO: 207)
Lys Tyr Phe Ile Gln Trp Leu Lys Asn Gly Gly Pro Ser Lys Asn Asn Ile Ala Ala Ala
Lys-palmitoyl D-His Ala Asp Gly Thr Phe Thr Ser Asp Tyr Ser Lys Tyr Leu Glu Glu Glu Leu Val     (SEQ ID NO: 208)
Lys Tyr Phe Ile Gln Trp Leu Lys Asn Gly Gly Pro Ser Lys Asn Asn Ile Ala Ala Ala
Lys-stearoyl D-His Ala Asp Gly Thr Phe Thr Ser Asp Tyr Ser Lys Tyr Leu Glu Glu Glu Leu Val     (SEQ ID NO: 209)
Lys Tyr Phe Ile Gln Trp Leu Lys Asn Gly Gly Pro Ser Lys Asn Asn Ile Ala Ala Ala
Lys-arachidoyl D-His Ser Gln Gly Thr Phe Thr Ser Asp Tyr Ser Lys Tyr Leu Glu Glu Glu Leu Val     (SEQ ID NO: 210)
Lys Tyr Phe Leu Gln Trp Leu Lys Asn Ala Gly Pro Ser Lys Asn Asn Ile Ala Glu Ala
Lys D-His Ser Gln Gly Thr Phe Thr Ser Asp Tyr Ser Lys Tyr Leu Glu Glu Glu Leu Val     (SEQ ID NO: 211)
Lys Tyr Phe Leu Gln Trp Leu Lys Asn Ala Gly Pro Ser Lys Asn Asn Ile Ala Glu Ala
Lys-myristoyl L-His Ser Gln Gly Thr Phe Thr Ser Asp Tyr Ser Lys Tyr Leu Glu Glu Glu Leu Val     (SEQ ID NO: 212)
Lys Tyr Phe Leu Gln Trp Leu Lys Asn Ala Gly Pro Ser Lys Asn Asn Ile Ala Glu Ala
Lys-myristoyl
```

-continued

```
D-His Ser Gln Gly Thr Phe Thr Ser Asp Tyr Ser Lys Tyr Leu Glu Glu Glu Leu Val        (SEQ ID NO: 213)
Lys Tyr Phe Leu Gln Trp Leu Lys Asn Ala Gly Pro Ser Lys Asn Asn Ile Ala Glu Ala
Lys-palmitoyl D-His Ser Gln Gly Thr Phe Thr Ser Asp Tyr Ser Lys Tyr Leu Glu Glu Glu Leu Val        (SEQ ID NO: 214)
Lys Tyr Phe Leu Gln Trp Leu Lys Asn Ala Gly Pro Ser Lys Asn Asn Ile Ala Glu Ala
Lys-arachidoyl
```

As mentioned above, the native human oxm sequence (which is the same as the rat and hamster) is as follows:

```
                                                                                      (SEQ ID NO: 357)
His Ser Gln Gly Thr Phe Thr Ser Asp Tyr Ser Lys Tyr Leu Asp Ser Arg Arg Ala Gln Asp Phe
Val Gln Trp Leu Met Asn Thr Lys Arg Asn Arg Asn Asn Ile Ala
```

The native bovine oxm sequence (which is the same as the porcine) is as follows:

```
                                                                                      (SEQ ID NO: 358)
His Ser Gln Gly Thr Phe Thr Ser Asp Tyr Ser Lys Tyr Leu Asp Ser Arg Arg Ala Gln Asp Phe
Val Gln Trp Leu Met Asn Thu Lys Arg Asn Lys Asn Asn Ile Ala
```

That is to say that it is the same as the human sequence except that Arg33 in the human peptide is replaced by Lys33 in the bovine peptide. The present invention provides analogues of oxyntomodulin as set out above. The invention further provides peptides that are analogues in which the Lys33 residue of the peptide recited above is replaced with Arg33.

In an embodiment, the invention provides a peptide of the invention in which residue Asn34 is replaced with Asp34. Certain peptides with Asn34 replaced by Asp34 are shown as PEPTIDES No 215 to 292 in FIG. 1. In a further embodiment, the invention provides a peptide in which residue Gln3 or Asp3 is replaced with Glu3. Certain peptides with Glu3 are shown as PEPTIDES No 293 to 355 in FIG. 1.

The invention further comprises embodiments incorporating the sequences disclosed in the attached examples and/or figures.

Derivatives

A compound of the invention may comprise a structure set forth above, modified by well known processes including amidation, glycosylation, carbamylation, alkylation, acylation, for example acetylation, sulfation, phosphorylation, cyclization, lipidization, protein (for example albumin) conjugation and pegylation. Analogues of the invention may be modified at random positions within the molecule, or at predetermined positions within the molecule and may include one, two, three or more attached chemical moieties.

A compound of the invention may be a fusion protein, whereby the analogue of oxyntomodulin is fused to another protein or polypeptide (the fusion partner) using recombinant methods known in the art. Alternatively, such a fusion protein may be synthetically synthesized by any known method. Such a fusion protein comprises the analogue of oxyntomodulin. Any suitable peptide or protein can be used as the fusion partner (e.g., serum albumin, carbonic anhydrase, glutathione-S-transferase, single chain antibodies, antibodies, antibody fragments or thioredoxin, etc.). For example, a compound of the invention could be fused to an immunoglobulin light chain variable domain that has binding specificity for serum albumin, as described in WO 05/118642. Preferred fusion partners will not have an adverse biological activity in vivo.

Such fusion proteins, including hybrid polypeptides, may be made by linking the carboxy-terminus of the fusion partner to the amino-terminus of the analogue of oxyntomodulin or vice versa, directly, or via a linker that preferably does not involve the loss of activity of components. Where present, the linker may be chemically stable, or labile, for example a cleavable linker may be used to link the analogue of oxyntomodulin to one or more fusion partners. A resulting cleavable fusion protein may be cleaved in vivo such that an active form of a compound of the invention is released. Examples of such cleavable linkers include, but are not limited to, the linkers D-D-D-D-Y, G-P-R, A-G-G and H-P-F-H-L, which can be cleaved by enterokinase, thrombin, ubiquitin cleaving enzyme and renin, respectively. See, e.g., U.S. Pat. No. 6,410,707.

Alternatively a compound of the invention may be a fusion protein, whereby the structure of the compound of the invention is attached to a fusion partner via disulphide bond(s) resulting in a covalent linkage between at least one Cys residue of the compound of the invention, and at least one Cys residue of the fusion partner.

When a protein is used as a fusion partner, it is preferably chosen so as not to exhibit undesirable antigenicity. Undesirable antigenicity may be avoided by choosing a protein which is allogenic to the animal to which the compound is to be administered.

A compound of the invention may be a physiologically functional derivative of a compound of the invention. The term "physiologically functional derivative" is used herein to denote a chemical derivative of a compound of the invention having the same physiological function as the corresponding unmodified compound of the invention. For example, a physiologically functional derivative may be convertible in the body to a compound of the invention. According to the present invention, examples of physiologically functional derivatives include esters, amides, and carbamates; preferably esters and amides.

Pharmaceutically acceptable esters and amides of the compounds of the invention may comprise a $C_{1-6}$ alkyl-, $C_{5-10}$ aryl-, $C_{5-10}$ ar-$C_{1-6}$ alkyl-, or amino acid-ester or -amide attached at an appropriate site, for example at an acid group.

Acyl side chains may be advantageous, for example, by their lipophilic nature causing the moiety to bind with albumin, thus causing a greatly reduced rate of clearance from a subject and so increasing half life and duration of effect. Whilst the acyl side chains may be lower acyl, for example $C_1$-$C_9$ acyl, especially $C_{1-6}$ acyl, they are preferred to be $C_{4-40}$, in particular $C_{8-25}$ acyl, especially $C_{16}$ or $C_{18}$ acyl. Palmitoyl is especially preferred as an acyl side chain as is lauroyl. Acyl side chains may be added at any position on the peptide back bone. An acyl substituent may be attached to an amino acid residue in such a way that a carboxyl group of the acyl substituent forms an amide bond with an amino group of the amino acid residue, Alternatively, an acyl substituent may be attached to an amino acid residue in such a way that an amino group of the acyl substituent forms an amide bond with a carboxyl group of the amino acid residue. In a further preferred embodiment, the present invention relates to an oxm derivative wherein an acyl substituent is attached to the parent peptide by means of a spacer. For example, the acyl substituent may be attached to the oxm moiety by means of a spacer in such a way that a carboxyl group of the spacer forms an amide bond with an amino group of the oxm moiety. It is especially preferred to add an acyl side chain (optionally via a spacer) at a position in the peptide back bone where a lysine residue is found. This is because lysine, having a four carbon atom side chain terminating at an epsilon-amino group, is particularly suitable for easily adding an acyl side chain. It may be necessary to introduce lysine residue into the sequence solely for the purpose of providing a convenient site at which to add an acyl side chain. Alternatively the acyl side chain may be added to the lysine residue in advance of the synthesis of the peptide, whereupon its incorporation at the relevant synthetic step will result directly in acylation. This methodology is advantageous if the peptide sequence contains more than one lysine residue as it avoids the necessity of using selective conditions that acylate only the particular lysine of interest. Preferably, the peptide derivatives have three, more preferably two, and most preferably one acyl side chain substituent. Examples of acyl (and other lipophilic substituents), approaches and specific synthetic methods of attaching such to peptides (with and without the use of spacers) are described in U.S. Pat. No. 6,268,343; and U.S. Pat. No. 6,458,924. Further examples of saturated fatty acids suitable for acyl derivatisation of compounds of the invention are butyric (butanoic acid): $CH_3(CH_{12})_2COOH$; caproic (hexanoic acid): $CH_3(CH_2)_4COOH$; caprylic (octanoic acid): $CH_3(CH_2)_6COOH$; capric (decanoic acid): $CH_3(CH_2)COOH$; lauric (dodecanoic acid): $CH_3(CH_2)_{10}COOH$; myristic (tetradecanoic acid): $CH_3(CH_2)_{12}COOH$; palmitic (hexadecanoic acid): $CH_3(CH_2)_{14}COOH$; stearic (octadecanoic acid): $CH_3(CH_2)_{16}COOH$; arachidic (eicosanoic acid): $CH_3(CH_2)_{18}COOH$; behenic (docosanoic acid): $CH_3(CH_2)_{20}COOH$.

According to certain preferred embodiments, acyl side chains may be added at position 30 and/or position 33 and/or positions 38 to 46 of the peptide back bone.

Pharmaceutically acceptable amides and carbonates of the compounds of Formula (I) may comprise a $C_{1-6}$ alkyl-, $C_{5-10}$ aryl-, $C_{5-10}$ ar-$C_{1-6}$ alkyl-, or amino acid-ester or -amide, or -carbamate attached at an appropriate site, for example at an amino group.

Methods for lipidization of sulfhydryl-containing compounds with fatty acid derivatives are disclosed in U.S. Pat. No. 5,936,092; U.S. Pat. No. 6,093,692; and U.S. Pat. No. 6,225,445. Fatty acid derivatives of a compound of the invention comprising a compound of the invention linked to fatty acid via a disulfide linkage may be used for delivery of a compound of the invention to neuronal cells and tissues. Lipidisation markedly increases the absorption of the compounds relative to the rate of absorption of the corresponding unlipidised compounds, as well as prolonging blood and tissue retention of the compounds.

Moreover, the disulfide linkage in lipidised derivative is relatively labile in the cells and thus facilitates intracellular release of the molecule from the fatty acid moieties. Suitable lipid-containing moieties are hydrophobic substituents with 4 to 26 carbon atoms, preferably 5 to 19 carbon atoms. Suitable lipid groups include, but are not limited to, the following: palmitoyl ($C_{15}H_{31}$), oleoyl ($C_{15}H_{29}$), stearoyl ($C_{17}H_{35}$), cholate; and deoxycholate.

It will be appreciated by the skilled artisan that particular amino acid residues may be introduced to the oxm sequence in order to facilitate one or more of the modifications described herein.

Cyclization methods include cyclization through the formation of a disulfide bridge and head-to-tail cyclization using a cyclization resin. Cyclized peptides may have enhanced stability, including increased resistance to enzymatic degradation, as a result of their conformational constraints. Cyclization may in particular be expedient where the uncyclized peptide includes an N-terminal cysteine group. Suitable cyclized peptides include monomeric and dimeric head-to-tail cyclized structures. Cyclized peptides may include one or more additional residues, especially an additional cysteine incorporated for the purpose of formation of a disulfide bond or a side chain incorporated for the purpose of resin-based cyclization.

A compound of the invention may be pegylated. Pegylated compounds of the invention may provide additional advantages such as increased solubility, stability and circulating time of the polypeptide, or decreased immunogenicity (see U.S. Pat. No. 4,179,337). WO 2006/082517 and US 2006/171920, which are incorporated herein by reference, provide examples and associated methods of pegylating peptides and analogues and derivatives thereof.

Chemical moieties for derivitization of a compound of the invention may also be selected from water soluble polymers such as polyethylene glycol, ethylene glycol/propylene glycol copolymers, carboxymethylcellulose, dextran, polyvinyl alcohol and the like. A polymer moiety for derivatisation of a compound of the invention may be of any molecular weight, and may be branched or unbranched. For ease in handling and manufacturing, the preferred molecular weight of a polyethylene glycol for derivatisation of a compound of the invention is from about 1 kDa to about 100 kDa, the term "about" indicating that in preparations of polyethylene glycol, some molecules will weigh more, some less, than the stated molecular weight. Polymers of other molecular weights may be used, depending on the desired therapeutic profile, for example the duration of sustained release desired, the effects, if any on biological activity, the ease in handling, the degree or lack of antigenicity and other known effects of the polyethylene glycol to a therapeutic protein or analog. For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

Salts and solvates of compounds of the invention that are suitable for use in a medicament are those wherein a counterion or associated solvent is pharmaceutically acceptable. However, salts and solvates having non-pharmaceutically acceptable counterions or associated solvents are within the scope of the present invention, for example, for use as intermediates in the preparation of the compounds of the invention and their pharmaceutically acceptable salts or solvates.

Suitable salts according to the invention include those formed with organic or inorganic acids or bases. Pharmaceutically acceptable acid addition salts include those formed with hydrochloric, hydrobromic, sulphuric, nitric, citric, tartaric, acetic, phosphoric, lactic, pyruvic, acetic, trifluoroacetic, succinic, perchloric, fumaric, maleic, glycollic, lactic, salicylic, oxaloacetic, methanesulfonic, ethanesulfonic, p-toluenesulfonic, formic, benzoic, malonic, naphthalene-2-sulfonic, benzenesulfonic, and isethionic acids. Other acids such as oxalic, while not in themselves pharmaceutically acceptable, may be useful as intermediates in obtaining the compounds of the invention and their pharmaceutical acceptable salts. Pharmaceutically acceptable salts with bases include ammonium salts, alkali metal salts, for example potassium and sodium salts, alkaline earth metal salts, for example calcium and magnesium salts, and salts with organic bases, for example dicyclohexylamine and N-methyl-D-glucomine.

Those skilled in the art of organic chemistry will appreciate that many organic compounds can form complexes with solvents in which they are reacted or from which they are precipitated or crystallized. Such complexes are known as "solvates". For example, a complex with water is known as a "hydrate". The present invention provides solvates of compounds of the invention.

Peptides of the invention may be made by any suitable technique for making peptides, including but not limited to conventional methodology, for example, synthesis from individual amino acids, especially step-wise synthesis using an automatic peptide synthesizer; modification of native peptides; or recombinant manufacturing techniques.

Conditions

The invention provides a pharmaceutical composition comprising a peptide according to the invention and one or more pharmaceutically acceptable carriers. The invention also provides a pharmaceutical composition for use in the control of appetite, feeding, food intake, energy expenditure and calorie intake, the composition comprising an effective amount of a compound according to the invention. More particularly, the invention provides a pharmaceutical composition for use in the treatment of obesity, for use in the treatment of eating disorders, or for use in the treatment of diabetes or a symptom of diabetes, or for use in the treatment or prevention of comorbidities associated with obesity or excess weight.

Moreover, the invention provides a method of reducing excess weight, for example cosmetic excess weight, comprising administering to a patient desiring to reduce weight an effective amount of a compound or a pharmaceutical composition according to the invention.

Furthermore, the invention provides a method of treating or preventing obesity or diabetes or another co-morbidity of obesity in a subject in need thereof comprising administering to the subject an effective amount of a compound or a pharmaceutical composition according to the invention.

The invention also provides a method of reducing appetite in a subject, reducing food intake in a subject or reducing calorie intake in a subject, reducing body weight in a subject, reducing body weight gain in a subject or increasing energy expenditure in a subject in need thereof comprising administering to the subject a peptide or a pharmaceutical composition according to the invention.

The invention also provides a method of causing weight loss or preventing weight gain for cosmetic purposes comprising administering to the subject a peptide or a pharmaceutical composition according to the invention.

The invention also provides a peptide of the invention for use as a medicament. It may for use as a medicament for the treatment of obesity or diabetes or of a co-morbidity of obesity.

It may be for use as a medicament for reducing appetite in a subject, reducing food intake in a subject or reducing caloric intake in a subject, reducing body weight in a subject, reducing body weight gain in a subject or increasing energy expenditure in a subject.

The invention also provides use of a compound according to the invention in the manufacture of a medicament for use in the treatment of a condition selected from obesity, eating disorders, diabetes, heart disease, hypertension, lipid disease, and disorders of intestinal and gastric motor activity and other aspects of gut and intestinal function, for example, water absorption and fluid handling, or pancreatic function including the endocrine pancreas, or disorders of hepato-biliary function, or prevention of cancer. In particular, the invention provides the use of a peptide of the invention for the manufacture of a medicament for the treatment of obesity or diabetes or of a co-morbidity of obesity. Further, the invention provides use of a compound according to the invention in the manufacture of a medicament for use in the control of any one or more of appetite, feeding, food intake, energy expenditure and calorie intake. In particular, the invention provides the use of a peptide of the invention for the manufacture of a medicament for reducing appetite in a subject, reducing food intake in a subject or reducing calorie intake in a subject, reducing body weight in a subject, reducing body weight gain in a subject or increasing energy expenditure in a subject.

The subject to whom the compound is administered may be overweight, for example, obese. Alternatively, or in addition, the subject may be diabetic, for example having insulin resistance or glucose intolerance, or both. The subject may have diabetes mellitus, for example, the subject may have Type II diabetes, The subject may be overweight, for example, obese and have diabetes mellitus, for example, Type II diabetes.

In addition, or alternatively, the subject may have, or may be at risk of having, a disorder in which obesity or being overweight is a risk factor. Such disorders include, but are not limited to, cardiovascular disease, for example hypertension, atherosclerosis, congestive heart failure, and dyslipidemia; stroke; gallbladder disease; osteoarthritis; sleep apnea; reproductive disorders for example, polycystic ovarian syndrome; cancers, for example breast, prostate, colon, endometrial, kidney, and esophagus cancer; varicose veins; acanthosis nigricans; eczema; exercise intolerance; insulin resistance; hypertension; hypercholesterolemia; cholithiasis; osteoarthritis; orthopedic injury; insulin resistance, for example, type 2 diabetes and syndrome X; metabolic syndrome; and thromboembolic disease (see Kopelman (2000), Nature 404: 635-43; Rissanen et al., British Med. J. 301, 835, 1990).

Other disorders associated with obesity include depression, anxiety, panic attacks, migraine headaches, PMS, chronic pain states, fibromyalgia, insomnia, impulsivity, obsessive-compulsive disorder, irritable bowel syndrome (IBS), and myoclonus. Furthermore, obesity is a recognized risk factor for increased incidence of complications of general anesthesia. (See e.g., Kopelman, Nature 404:635-43, 2000). In general, obesity reduces life span and carries a serious risk of co-morbidities such as those listed above.

Other diseases or disorders associated with obesity are birth defects, maternal obesity being associated with increased incidence of neural tube defects, carpal tunnel syndrome (CTS); chronic venous insufficiency (CVI); daytime sleepiness; deep vein thrombosis (DVT); end stage renal disease (ESRD); gout; heat disorders; impaired immune response; impaired respiratory function; infertility; liver disease; lower back pain; obstetric and gynecologic complications; pancreatititis; as well as abdominal hernias; acanthosis nigricans; endocrine abnormalities; chronic hypoxia and hypercapnia; dermatological effects; elephantitis; gastroesophageal reflux; heel spurs; lower extremity edema; mammegaly which causes considerable problems such as bra strap pain, skin damage, cervical pain, chronic odors and infections in the skin folds under the breasts, etc.; large anterior abdominal wall masses, for example abdominal panniculitis with frequent panniculitis, impeding walking, causing frequent infections, odors, clothing difficulties, lower back pain; musculoskeletal disease; pseudo tumor cerebri (or benign intracranial hypertension), and sliding hiatil hernia.

Wynne et al (International Journal of Obesity 12: 1729-1736, 2006) described how administering 400 nmoles of preprandial oxyntomodulin, three times daily for four days, increased activity-related energy expenditure by 143+/−109 kcal/day or 26.2+/−9.9% (P=0.0221); total energy expenditure by 9.4+/−4.8% (P=0.0454) and physical activity level by 9.5+/−4.6% (P=0.0495). Accordingly, the present invention further provides a method for increasing energy expenditure in a subject. The method includes, for example, peripherally administering a therapeutically effective amount of a compound of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect the method of the invention involves manipulation of the arcuate circuitry that alter food intake coordinately, and reciprocally alter energy expenditure. Energy expenditure is a result of cellular metabolism, protein synthesis, metabolic rate, and calorie utilization. Thus, in this aspect of the invention, administration of a compound of the invention may result in increased energy expenditure, and decreased efficiency of calorie utilization.

The invention also provides a method for improving a lipid profile in a subject. The invention also provides a method for alleviating a condition or disorder that can be alleviated by reducing nutrient availability.

Appetite can be measured by any means known to one of skill in the art. For example, decreased appetite can be assessed by a psychological assessment. For example, administration of a compound of the invention results in a change in perceived hunger, satiety, and/or fullness. Plunger can be assessed by any means known to one of skill in the art. For example, hunger is assessed using psychological assays, such as by an assessment of hunger feelings and sensory perception using a questionnaire, such as, but not limited to, a Visual Analog Score (VAS) questionnaire. In one specific, non-limiting example, hunger is assessed by answering questions relating to desire for food, drink, prospective food consumption, nausea, and perceptions relating to smell or taste.

A compound of the invention may be used for weight control and treatment, for example reduction or prevention of obesity, in particular any one or more of the following: preventing and reducing weight gain; inducing and promoting weight loss; and reducing obesity as measured by the Body Mass Index. A compound of the invention may be used in the control of any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. A compound of the invention may be used in maintaining any one or more of a desired body weight, a desired Body Mass Index, a desired appearance and good health.

A subject may be a subject who desires weight loss, for example female and male subjects who desire a change in their appearance. A subject may desire decreased feelings of hunger, for example the subject may be a person involved in a lengthy task that requires a high level of concentration, for example soldiers on active duty, air traffic controllers, or truck drivers on long distance routes, etc.

The present invention may also be used in treating, prevention, ameliorating or alleviating conditions or disorders caused by, complicated by, or aggravated by a relatively high nutrient availability. The term "condition or disorder which can be alleviated by reducing caloric (or nutrient) availability" is used herein to denote any condition or disorder in a subject that is either caused by, complicated by, or aggravated by a relatively high nutrient availability, or that can be alleviated by reducing nutrient availability, for example by decreasing food intake. Subjects who are insulin resistant, glucose intolerant, or have any form of diabetes mellitus, for example, type 1, 2 or gestational diabetes, can also benefit from methods in accordance with the present invention.

Conditions or disorders associated with increased caloric intake include, but are not limited to, insulin resistance, glucose intolerance, obesity, diabetes, including type 2 diabetes, eating disorders, insulin-resistance syndromes, and Alzheimer's disease.

According to the present invention, a compound of the invention is preferably used in the treatment of a human. However, while the compounds of the invention will typically be used to treat human subjects they may also be used to treat similar or identical conditions in other vertebrates for example other primates; farm animals for example swine, cattle and poultry; sport animals for example horses; companion animals for example dogs and cats.

In summary, the invention also provides a peptide of the invention for use as a medicament for the prevention or treatment of obesity. There is also provided a peptide of the invention for use as a medicament for the prevention or treatment of diabetes or of a co-morbidity of obesity. Further, there is provided a peptide of the invention for use as a medicament for reducing appetite in a subject, reducing food intake in a subject or reducing calorie intake in a subject, reducing body weight in a subject, reducing body weight gain in a subject or increasing energy expenditure in a subject.

The invention also provides a method of treating or preventing obesity in a subject in need thereof comprising administering to the subject a peptide according to the invention. There is also provided a method of treating or preventing diabetes or of a co-morbidity of obesity in a subject in need thereof comprising administering to the subject a peptide according to the invention. Further, there is provided a method of reducing appetite in a subject, reducing food intake in a subject or reducing calorie intake in a subject, reducing body weight in a subject, reducing body weight gain in a subject or increasing energy expenditure in a subject in need thereof comprising administering to the subject a peptide according to the invention or a pharmaceutical composition according to the invention.

Compositions

While it is possible for the active ingredient to be administered alone, it is preferable for it to be present in a pharmaceutical formulation or composition. Accordingly, the invention provides a pharmaceutical formulation comprising a compound of the invention, or a variant or derivative thereof, or a salt or solvate thereof, as defined above, and a pharmaceutically acceptable excipient. Pharmaceutical compositions of the invention may take the form of a pharmaceutical formulation as described below.

The pharmaceutical formulations according to the invention include those suitable for oral, parenteral (including subcutaneous, intradermal, intramuscular, intravenous, and intraarticular), inhalation (including fine particle dusts or mists which may be generated by means of various types of metered doses, pressurized aerosols, nebulizers or insufflators, and including intranasally or via the lungs), rectal and topical (including dermal, transdermal, transmucosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with a pharmaceutical carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2 S, 1988.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The compounds can be formulated, for administration orally, with delivery agents or carriers that facilitate the transport of therapeutic macromolecules and highly charged compounds across cell membranes, especially in the small intestine. Such delivery agents or carriers may in addition inhibit enzymatic degradation of peptides during passage through the gastrointestinal (GI) tract and/or the formulation may include additional agents that protect against such degradation. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of the invention can also be delivered through the oral cavity by sublingual and/or buccal administration. Moulded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to oxm and oxm agonists.

Excipients that can be included are, for instance, other proteins, such as human serum albumin or plasma preparations. If desired, the pharmaceutical composition may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743). Intranasal formulations may include delivery agents for reversibly opening the nasal tight junction, thereby increasing drug permeability (e.g., see U.S. patent application Ser. No. 10/322,266).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as hereinbefore recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavouring agents.

The compounds of the invention are also suitably administered as sustained-release systems. Suitable examples of sustained-release systems of the invention include suitable polymeric materials, for example semi-permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically, for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of the invention. These compositions exhibit certain biocompatibility features which allow a controlled release of the active substance. See U.S. Pat. No. 5,700,486.

A compound of the invention may be delivered by way of a pump (see Langer, Science 249:1527-1533, 1990; Sefton, CRC Crit. Ref. Biomed. Eng. 14:201, 1987; Buchwald et al., Surgery 88:507, 1980; Saudek et al., N. Engl. J. Med. 321: 574, 1989) or by a continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner. Other controlled release systems are discussed in the review by Langer, supra. In another aspect of the disclosure, compounds of the invention are delivered by way of an implanted pump, described, for example, in U.S. Pat. No. 6,436,091; U.S. Pat. No. 5,939,380; U.S. Pat. No. 5,993,414.

Implantable drug infusion devices are used to provide patients with a constant and long term dosage or infusion of a drug or any other therapeutic agent. Essentially such device may be categorized as either active or passive. A compound of the present invention may be formulated as a depot preparation. Such a long acting depot formulation can be administered by implantation, for example subcutaneously or intramuscularly; or by intramuscular injection. Thus, for example, the compounds can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of a compound of the invention may be administered as a single pulse dose, as a bolus dose, or as pulse doses administered over time. Thus, in pulse doses, a bolus administration of a compound of the invention is provided, followed by a time period wherein a compound of the invention is administered to the subject, followed by a second bolus administration. In specific, non-limiting examples, pulse doses of a compound of the invention are administered during the course of a day, during the course of a week, or during the course of a month.

In one embodiment, a therapeutically effective amount of a compound of the invention is administered with a therapeutically effective amount of another agent, for example an additional appetite suppressant, a food-intake-reducing, dipetidyl peptidase-IV (DPP-IV) inhibiting, plasma glucose-lowering or plasma lipid-altering agent. Specific, non-limiting examples of an additional appetite suppressant include amfepramone (diethylpropion), phentermine, mazindol and phenylpropanolamine, fenfluramine, dexfenfluramine, sibutramine, rimonabant, and fluoxetine. Specific, non-limiting examples of DPP-IV inhibitors include Januvia (sitagliptin phosphate), and Galvus (vildagliptin). The compound of the invention can be administered simultaneously with the additional agent, or it may be administered sequentially. Thus, in one embodiment, the compound of the invention is formulated and administered with an additional agent as a single dose.

In another embodiment, a therapeutically effective amount of a compound of the invention is administered in combination with a therapeutically effective amount of another agent, for the treatment of diseases other than obesity, for example diabetes, in which specific non limiting examples of an additional therapeutic agent are GLP-1 or an analogue thereof, exenatide, and pramlintide.

A compound of the invention may be administered whenever the effect, e.g., appetite suppression, decreased food intake, or decreased caloric intake, is desired, or slightly before to whenever the effect is desired, such as, but not limited to about 10 minutes, about 15 minutes, about 30 minutes, about 60 minutes, about 90 minutes, about 120 minutes, about 4 hours, about 8 hours, or about 12 hours, before the time the effect is desired.

A compound of the invention may be administered in combination with whenever the effect, e.g., appetite suppression, decreased food intake, or decreased caloric intake, is desired, or slightly before to whenever the effect is desired, such as, but not limited to about 10 minutes, about 15 minutes, about 30 minutes, about 60 minutes, about 90 minutes, about 120 minutes, about 4 hours, about 8 hours, or about 12 hours, before the time the effect is desired.

Dosages

The therapeutically effective amount of a compound of the invention will be dependent on the molecule utilized, the subject being treated, the severity and type of the affliction, and the manner and route of administration. For example, a therapeutically effective amount of a compound of the invention may vary from about 0.01 µg per kilogram (kg) body weight to about 1 g per kg body weight, for example about 0.01 µg to about 5 mg per kg body weight, or about 1 µg to about 1 mg per kg body weight per day. A compound of the invention may be administered to a subject at 0.5 to 200 picomole (pmol) per kg body weight, or about 20 µmol per kg body weight. For especially active compounds or compounds administered by an especially efficient route, in one specific, non-limiting example, a compound of the invention is administered in a dose of about 1 mmol or more, 2 nmol or more, 5 nmol or more, or 10 nmol or more and the dose of the compound of the invention is generally not more than 100 nmol, for example, the dose is 90 nmols or less, 80 nmols or less, 70 nmols or less, 60 nmols or less, 50 nmols or less, 40 nmols or less, 30 nmols or less, 20 mmols or less, or 10 nmols or less. For a less active compound or a compound administered by a less efficient route, in another specific, non-limiting example, a compound of the invention is administered in a dose of about 100 nmol or more, 200 nmol or more, 300 nmol or more, 400 nmol or more, 500 nmol or more, 600 nmol or more, 700 nmol or more, 800 nmol or more, 900 nmol or more, or 1 µmol or more and the dose of the compound of the invention is generally not more than 10 µmols, for example, the dose is 9 µmols or less, 8 µmols or less, 7 µmols or less, 6 µmols or less, 5 µmols or less, 4 µmols or less, 3 µmols or less, 2 µmols or less, 1 µmol or less. For example, a dosage range may comprise any combination of any of the specified lower dose limits with any of the specified upper dose limits. Thus, examples of non-limiting dose ranges of compounds of the invention are within the range of from 1 nmol to 1 µmol, from 1 to 900 nmols, or from 1 to 800 nmols. For especially active compounds or compounds administered by an especially efficient route, the dose may be from 1 nmol to 100 nmol, from 2 to 80 nmols, or from 5 to 60 nmols. For a less active compound or a compound administered by a less efficient route, the dose may be from 100 nmol to 10 nmol, from 200 nmol to 5 µmols, or from 500 nmols to 2 µmols.

In one specific, non-limiting example, from about 0.5 to about 50 mmol of a compound of the invention is administered, for example about 1 to about 20 nmol, for example, about 2 nmol is administered as a subcutaneous injection. The exact dose is readily determined by one of skill in the art based on the potency of the specific compound utilized, the age, weight, sex and physiological condition of the subject.

In another specific non-limiting example, a compound of the invention is administered to a subject in a dose of about 1 µg to about 2 mg per dose, about once, about twice, about three times, or about four times per day. A therapeutically effective amount of a compound of the invention may vary from about 0.01 µg per kilogram (kg) body weight to about 1 g per kg body weight, for example about 0.1 µg to about 5 mg per kg body weight, or about 5 µg to about 1 mg per kg body weight per day. Bearing in mind that a typical oxyntomudilin analogue of the invention has a molecular weight of around 4500, a compound of the invention may be administered to a subject at 2.25 to 900 ng per kg body weight, or about 90 ng per kg body weight. For especially active compounds or compounds administered by an especially efficient route, in one specific, non-limiting example, a compound of the invention is administered in a dose of about 4.5 µg or more, 9 µg or more, 22.5 µg or more, or 45 µg or more and the dose of the compound of the invention is generally not more than 450 µg, for example, the dose is 405 µg or less, 360 µg or less, 315 µg or less, 270 µg or less, 225 µg or less, 180 µg or less, 135 µg or less, 90 µg or less, or 45 µg or less. For a less active compound or a compound administered by a less efficient route, in another specific, non-limiting example, a compound of the invention is administered in a dose of about 450 µg or more, 900 µg or more, 1350 µg or more, 1800 µg or more, 2250 µg or more, 2700 µg or more, 3150 µg or more, 3600 µg or more, 4050 µg or more, or 4500 µg or more and the dose of the compound of the invention is generally not more than 45000 µg, for example, the dose is 40500 µg or less, 36000 µg or less, 31500 µg or less, 27000 µg or less, 22500 µg or less, 18000 µg or less, 13500 µg or less, 9000 µg or less, 45000 µg or less. For example, a dosage range may comprise any combination of any of the specified lower dose limits with any of the specified upper dose limits. Thus, examples of non-limiting dose ranges of compounds of the invention are within the range of from 4.5 µg to 4500 µg, from 4.5 to 4050 µg, or from 4.5 to 3600 µg. For especially active compounds or compounds administered by an especially efficient route, the dose may be from 4.5 µg to 450 µg, from 9 to 360 µg, or from 22.5 to 270 µg. For a less active compound or a compound administered by a less efficient route, the dose may be from 450 µg to 45000 µg, from 900 µg to 22500 µg, or from 2250 to 9000 µg.

Suitable doses of compounds of the invention also include those that result in a reduction in calorie intake, food intake, or appetite, or increase in energy expenditure that is equivalent to the reduction in calorie intake, food intake, or appetite, or to increase the energy expenditure, caused by levels of oxm that have been observed in man. Examples of doses include, but are not limited to doses that produce the effect demonstrated when the serum levels of oxm are from about 800 pM to about 1300 pM, or from about 900 pM to about 1000 pM, or about 950 pM.

Suitable doses of compounds of the invention also include those that are equivalent to levels of oxm seen in subjects experiencing conditions associated with reduced appetite, for example jejunoileal bypass (Sarson et al., *Int J Obes*, 1981, 5:471-480; Holst et al., *Scand J Gastroenterol*, 1979, 14:205-207).

In a study of the effects of oxyntomodulin on appetite suppression and food intake reduction in humans (Cohen et al., *J. Clin. Endocrinol. Metab.*, 2003, 88(10), 4696-4701) it was found that an infusion of oxyntomodulin to human volunteers at 3.0 pmol/kg.min for 90 minutes led to a significantly reduced ad libitum energy intake (19.3+/−5.6%; P<0.01). The total oxyntomodulin infused was 270 pmol/kg body weight. The observed oxyntomodulin-like immunoreactivity in the blood of the subjects rose to around 800 pmol/L during the infusion.

In a study of the effects of oxyntomodulin on weight loss in humans (Wynne et al., *Diabetes.*, 2005, 54(August), 2390-2395) it was found that subcutaneous injections of oxyntomodulin to humans volunteers resulted in a significant reduction of body weight. Over the study period of 28 days, body weight of the treatment group was reduced by 2.3±0.4 kg in the treatment group compared with 0.5±0.5 kg in the control group (P=0.0106). 1.8 mg (approximately 400 mmol) of oxyntomodulin was administered three times daily 30 mins before meals. On average, the treatment group had an additional 0.45 kg weight loss per week. Energy intake by the treatment group was significantly reduced by 170±37 kcal (25±5%) at the initial study meal within the 28 day study period (P=0.0007) and by 250±63 kcal (35±9%) at the final study meal during the 28 day study period (P=0.0023), with no change in subjective food palatability. Oxyntomodulin treatment resulted in weight loss and a change in the levels of adipose hormones consistent with a loss of adipose tissue. The anorectic effect was maintained over the 4-week period.

The compounds of the invention have been found to be more active and/or longer-lasting than native oxyntomodulin as used in human studies to date (Cohen et al. (2003) and Wynne et al. (2005) *Diabetes* 54(August), 2390-2395). The dosage required for a compound of the invention may be somewhat lower than that required for native oxyntomodulin. The dosages of peptides of the invention required to observe an effect in humans can be expected to be a lower, for example 2.5 times, 200 times, 400 times, and 1-4000 times lower than the dose of native oxyntomodulin. The magnitude of the potency of the peptides of the invention in comparison to the native oxyntomodulin peptide may also allow the frequency of administration a compound of the invention to be lower than that required for native oxyntomodulin.

The disclosure is illustrated by the following non-limiting Examples.

EXAMPLES

Materials and Methods

Animals: All animal procedures were approved by the British Home Office Animals (Scientific Procedures) Act 1986 (Project License number 70/5516). Male C57BL/6 mice and male Wistar rats were maintained in individual cages under controlled temperature (21-23° C.) with ad libitum access to standard chow (RMI diet, SDS Ltd, Witham, Essex, UK) and to water. The light cycle was 12 hours light and 12 hours dark with 'dawn' at 07:00, lights full on at 07:30, 'dusk' at 19:00 with lights off at 19:30. These times were fixed in the animal facility, All animals were handled almost daily for on average nine days prior to the first study. During the acclimatization period, mice received two saline injections at least two days apart in order to further acclimatize to the procedure on the study days. It was found in rats that minimising the number of injections provided an optimal response, and so acclimatization injections were not used.

Intra-peritoneal (IP) injections: JP injections were administered to mice via a 0.5 ml syringe with a 29-gauge needle (maximum injection volume 0.1 ml). The maximum volume administered IP was 0.1 ml.

Subcutaneous (SC) injections: SC injections were administered to rats via a 0.5 ml syringe with a 29-gauge needle (maximum injection volume 0.2 ml), in a volume of 0.1 ml if administered to the thigh skin, or 0.2 ml if administered to the neck scruff.

Study protocol: C57BL/6 mice (20-35 g) were injected with the peptide under investigation following a 20-hour fast. Wistar rats were injected following a 24-hour fast. Typically 6 to 10 rodents were used per experimental group. Injections were typically administered at 9:00. A pre-weighed quantity of chow was presented immediately after injection. The remaining food was measured at regular time intervals (e.g. 1, 2, 3, 4, 6, 8, 24, 32 and 48 hours following injection) and food intake calculated.

Peptides Synthesis
Synthesis of Peptides

Peptides were produced by solid phase step-wise synthesis (SPSS) using the Fmoc N-terminal protection strategy. Chain assembly was performed on Applied Biosystems 431, 433 or Pioneer automated synthesisers. Solid phase resins were used with factory pre-loaded C terminal amino acid or with an amide linker as appropriate. The following side-chain protecting groups were used: Asn(Trt), Gln(Trt), Cys(Trt), His(Trt), Asp(tBu), Glu(tBu), Ser(tBu), Thr(tBu), Tyr(tBu), Arg(Pbf), Lys(Boc), Trp(Boc). In some cases, where synthesis difficulty was anticipated, pre-formed oxazolidine dipeptides were used in place of respective monomers. All chemicals (from various suppliers including Applied Biosystems, Merck Biosciences and AGCT) were synthesis grade. Feedback monitoring to optimise syntheses was employed on all instruments.

Recovery of Peptides

After synthesis, peptides were cleaved from the solid phase resin support and fully side chain deprotected. This was achieved by treatment for 2 hours with trifluoroacetic acid (TFA) containing 4% water and 2.5% tri-isopropylsilane to scavenge side-chain protecting groups. Peptide-TFA solutions were filtered from the resins and the peptides precipitated with methyl tertiary butyl ether (MTBE). Peptides were isolated by centrifugation, washed in MTBE and dried under vacuum.

Analysis and Purification of Peptides

Peptides were dissolved in de-ionized water, with addition of acetic acid where necessary. Peptide solutions were clarified by centrifugation or filtration (Whatman GD/X syringe filter) prior to analysis and purification.

All peptide products were analysed by reverse phase HPLC on an Applied Biosystems BioCad instrument using an analytical Brownlee Aquapore RP300 C8 or Phenomenex Synergi Hydro C18 column. Purification was performed by reverse phase HPLC using preparative columns of the above types. Acetonitrile-water gradients (with TFA as counter-ion) were used for elution of products. Capillary Zone Electrophoresis (CZE) was performed on crude and purified peptides using a Hewlett Packard 3DCE instrument. Molecular weight determination was performed on a Micromass MALDI-R mass spectrometer.

Purified peptides were freeze-dried in pharmaceutical grade glass vials (Adelphi Vials) and closed under vacuum.

Derivatised Side Chains

Peptides having side chains derivatised with an acyl or alkyl group were prepared by standard methods.

Solubility of Derivatised Peptides

Derivatised polypeptides should be fully dissolved before administration. In order to achieve solubility it may be necessary to dissolve the polypeptides in a small amount of dilute alkali (for example, 50 µl 0.01 NaOH) and then dilute the dissolved peptide in saline.

Inhibition of Food Intake Experiments

Example 1

Comparative Example

The feeding effect of native oxyntomodulin (human) was investigated by intraperitoneal injection of 1400 mmoles/kg to groups of fasted mice. A further group was administered saline (control). Mean cumulative food intake over the course of 24 hours is shown in comparison to saline in FIG. 2. Due to the relatively low activity of native oxyntomodulin, a high dose was given. Less significant results are observed with lower doses.

Example 2

Comparative Example

The feeding effect of native oxyntomodulin (human) was investigated by subcutaneous injection of 1400 mmoles/kg to groups of fasted rats. A further group was administered saline (control). Mean cumulative food intake over the course of 6 hours is shown in comparison to saline in FIG. 3. It can be seen that even at a high dose of 1400 nmol/kg, native oxyntomodulin is not capable of reducing food intake in fasted rats under these conditions. At lower doses, the same lack of effectiveness is observed.

Example 3

The feeding effects of the following analogues of oxyntomodulin were investigated: PEPTIDE NO: 178 [SEQ.ID NO:178]; PEPTIDE NO: 82 [SEQ ID NO: 82]; PEPTIDE NO: 58 [SEQ ID NO:58]; and PEPTIDE NOW 52 [SEQ ID NO:52]. The analogues were administered at a dose of 10 (PEPTIDE NO: 178 [SEQ ID NO: 178]) and 10 (PEPTIDE NO: 82 [SEQ ID NO:82]; PEPTIDE NO: 58 [SEQ ID NO:58]; and PEPTIDE NO: 52 [SEQ ID NO:52]) nmoles/kg by subcutaneous injection to groups of fasted rats. A further group was administered saline (control). Mean cumulative food intake over the course of 24 hours is shown in comparison to saline in FIGS. 4 to 7. The analogues demonstrate a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 4

The feeding effects of the following analogues of oxyntomodulin were investigated: PEPTIDE NO: 164 [SEQ ID NO:164]; and PEPTIDE NO: 167 [SEQ ID NO:167]. The analogues were administered at a dose of 4 and 5 nmoles/kg respectively, by subcutaneous injection to groups of fasted rats. A further group was administered saline (control). Mean cumulative food intake over the course of 48 hours (PEPTIDE NO: 164 [SEQ ID NO: 164]) and 32 hours (PEPTIDE NO: 167 [SEQ ID NO: 167]) is shown in comparison to saline in FIGS. 8 and 9. The analogues demonstrate a potent and long acting suppression of food intake in comparison to the saline control. The food intake suppression continues for the whole 48 (PEPTIDE NO: 164 [SEQ ID NO:164]) and 32 (PEPTIDE NO: 167 [SEQ ID NO: 167]) hour period; that is to say that the food intake over the first 24 hour period is lower than in the saline control and continues to remain below it in the following 24 hours (PEPTIDE NO: 164 [SEQ ID NO: 164]) or 8 hours (PEPTIDE NO: 167 [SEQ ID NO:167]). It is also lower than in the control group treated with native oxyntomodulin.

Example 5

The feeding effects of the following analogues of oxyntomodulin were investigated: PEPTIDE NO: 100 [SEQ ID NO: 100]; and PEPTIDE NO: 148 [SEQ ID NO: 148]. The analogues were administered at a dose of 20 and 10 nmoles/kg respectively, by subcutaneous injection to groups of fasted rats. A further group was administered saline (control). Mean cumulative food intake over the course of 24 hours is shown in comparison to saline in FIGS. 10 and 11. The analogues demonstrate a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 6

The feeding effects of the following analogues of oxyntomodulin were investigated: PEPTIDE NO: 60 [SEQ ID NO:60]; and PEPTIDE NO: 94 [SEQ ED NO:94]. The analogues were administered at a dose of 100 and 5 nmoles/kg respectively, by subcutaneous injection to groups of fasted rats. A further group was administered saline (control). Mean cumulative food intake over the course of 24 hours is shown in comparison to saline in FIGS. 12 and 13. The analogues demonstrate a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 7

The feeding effects of the following analogue of oxyntomodulin was investigated: PEPTIDE NO: 155 [SEQ ID NO: 155]. The analogue was administered at a dose of 4 nmoles/kg by subcutaneous injection to a group of fasted rats. A further group was administered saline (control). Mean cumulative food intake over the course of 32 hours is shown in comparison to saline in FIG. 14. The analogue demonstrates a potent and long acting suppression of food intake in comparison to the saline control. The food intake suppression continues for the whole 32 hour period; that is to say that the food intake over the first 24 hour period is lower than in the saline control and continues to remain below it in the following 8 hours. It is also lower than in the control group treated with native oxyntomodulin.

Example 8

The feeding effects of the following analogues of oxyntomodulin were investigated: PEPTIDE NO: 142 [SEQ ID NO: 142]; PEPTIDE NO: 184 [SEQ ID NO: 184]; and PEPTIDE NO: 172 [SEQ ID NO:172]. The analogues were administered at a dose of 3 nmoles/kg by subcutaneous injection to groups of fasted rats. A further group was administered saline (control). Mean cumulative food intake over the course of 24 hours is shown in comparison to saline in FIGS. 15 to 17. The analogues demonstrate a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 9

The feeding effects of the following analogues of oxyntomodulin were investigated: PEPTIDE NO: 4 [SEQ ID NO:4]; PEPTIDE NO: 195 [SEQ ID NO: 195]; PEPTIDE NO: 136 [SEQ ID NO: 136]; and PEPTIDE NO: 108 [SEQ ID NO: 108]. The analogues were administered at doses of 5, 800, 5 and 100 nmoles/kg respectively, by intraperitoneal injection to groups of fasted mice. A further group was administered saline (control). Mean cumulative food intake over the course of 24 hours is shown in comparison to saline in FIGS. 18 to 21. The analogues demonstrate a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 10

The feeding effects of the following analogues of oxyntomodulin were investigated: PEPTIDE NO: 142 [SEQ ID NO:142]; PEPTIDE NO: 22 [SEQ ID NO:22]; PEPTIDE NO: 153 [SEQ ID NO: 153]; and PEPTIDE NO: 199 [SEQ ID NO: 199]. The analogues were administered at a dose of 3 nmoles/kg, 200 mmoles/kg (PEPTIDE NO: 153 [SEQ ID NO: 153]), and 500 nmoles/kg (PEPTIDE NO, 199 [SEQ ID NO, 199]) by subcutaneous injection to groups of fasted rats. A further group was administered saline (control), Mean cumulative food intake over the course of 24 hours is shown in comparison to saline in FIGS. 22 to 25. The analogues demonstrate a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 11

The feeding effects of the following analogues of oxyntomodulin were investigated: PEPTIDE NO: 210 [SEQ ID NO:210]; PEPTIDE NO: 211 [SEQ ID NO:21 I]; PEPTIDE NO: 213 [SEQ ID NO:213]; and PEPTIDE NO: 214 [SEQ ID NO:214]. The analogues were administered at a dose of 20, 200, 400 and 400 nmoles/kg respectively by intraperitoneal injection to groups of fasted mice. A further group was administered saline (control). Mean cumulative food intake over the course of 48 hours is shown in comparison to saline in FIGS. 26 to 29. The analogues demonstrate a potent and long acting suppression of food intake in comparison to the saline control. The food intake suppression continues for the whole 48 hour period; that is to say that the food intake over the first 24 hour period is lower than in the saline control and continues to remain below it in the following 24 hours. It is also lower than in the control group treated with native oxyntomodulin.

Example 12

The feeding effects of the following analogues of oxyntomodulin were investigated: PEPTIDE NO: 201 [SEQ ID NO:201]; and PEPTIDE NO: 202 [SEQ ID NO:202]. The analogues were administered at a dose of 5 nmoles/kg by subcutaneous injection to groups of fasted rats. A further group was administered saline (control). Mean cumulative food intake over the course of 48 hours is shown in comparison to saline in FIGS. 30 and 31. The analogues demonstrate a potent and long acting suppression of food intake in comparison to the saline control. The food intake suppression continues for the whole 48 hour period; that is to say that the food intake over the first 24 hour period is lower than in the saline control and continues to remain below it in the following 24 hours. It is also lower than in the control group treated with native oxyntomodulin.

Example 13

The feeding effect of the following analogue of oxyntomodulin was investigated: PEPTIDE NO: 203 [SEQ ID NO:203]. The analogue was administered at a dose of 100 nmoles/kg by subcutaneous injection to a group of fasted rats. A further group was administered saline (control). Mean cumulative food intake over the course of 24 hours is shown in comparison to saline in FIG. 32. The analogue demonstrates a potent and long acting suppression of food intake in comparison to the saline control. The food intake suppression continues for the whole 24 hour period; that is to say that the food intake over the 24 hour period is lower than in the saline control, It is also lower than in the control group treated with native oxyntomodulin.

Example 14

The feeding effects of the following analogues of oxyntomodulin were investigated: PEPTIDE NOW 204 [SEQ ID NO:204]; and PEPTIDE NO: 205 [SEQ ID NO:205]. The analogues were administered at a dose of 5 nmoles/kg by subcutaneous injection to groups of fasted rats. A further group was administered saline (control). Mean cumulative food intake over the course of 32 hours is shown in comparison to saline in FIGS. 33 and 34. The analogues demonstrate a potent and long acting suppression of food intake in comparison to the saline control. The food intake suppression continues for the whole 32 hour period; that is to say that the food intake over the first 24 hour period is lower than in the saline control and continues to remain below it in the following 8 hours. It is also lower than in the control group treated with native oxyntomodulin.

Example 15

The feeding effects of the following analogues of oxyntomodulin were investigated: PEPTIDE NO: 206 [SEQ ID NO:206]; PEPTIDE NO: 207 [SEQ ID NO:207] and PEPTIDE NO: 209 [SEQ ID NO:209]. The analogues were administered at a dose of 80 mmoles/kg by subcutaneous injection to groups of fasted rats. A further group was administered saline (control). Mean cumulative food intake over the course of 48 hours is shown in comparison to saline in FIGS. 35 to 37. The analogues demonstrate a potent and long acting suppression of food intake in comparison to the saline control. The food intake suppression continues for the whole 48 hour period; that is to say that the food intake over the first 24 hour period is lower than in the saline control and continues to remain below it in the following 24 hours. It is also lower than in the control group treated with native oxyntomodulin.

Example 16

The feeding effect of the following analogue of oxyntomodulin was investigated: PEPTIDE NO: 215 [SEQ ID NO:215]. The analogue was administered at a dose of 5 nmoles/kg by subcutaneous injection to a group of fasted rats. A further group was administered saline (control). Mean cumulative food intake over the course of 24 hours is shown in comparison to saline in FIG. 38. The analogue demonstrates a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 17

The feeding effect of the following analogue of oxyntomodulin was investigated: PEPTIDE NO: 216 [SEQ ID NO:216]. The analogue was administered at a dose of 10 nmoles/kg by subcutaneous injection to a group of fasted rats, A further group was administered saline (control). Mean cumulative food intake over the course of 24 hours is shown in comparison to saline in FIG. 39. The analogue demonstrates a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

Example 18

The feeding effect of the following analogue of oxyntomodulin was investigated: PEPTIDE NO: 355 [SEQ ID NO:355]. The analogue was administered at a dose of 5 mmoles/kg by subcutaneous injection to a group of fasted mice. A further group was administered saline (control). Mean cumulative food intake over the course of 4 hours is shown in comparison to saline in FIG. 40. The analogue demonstrates a potent and long acting suppression of food intake in comparison to the saline control. The food intake suppression continues for the whole 4 hour period; that is to say that the food intake over the 4 hour period is lower than in the saline control. It is also lower than in the control group treated with native oxyntomodulin.

Example 19

The feeding effect of the following analogue of oxyntomodulin was investigated: PEPTIDE NO: 130 [SEQ ID NO: 130]. The analogue was administered at a dose of 20 nmoles/kg by subcutaneous injection to a group of fasted mice. A further group was administered saline (control). Mean cumulative food intake over the course of 24 hours is shown in comparison to saline in FIG. 41. The analogue demonstrates a potent and long acting suppression of food intake in comparison to the saline control. The food intake suppression continues for the whole 24 hour period; that is to say that the food intake over the 24 hour period is lower than in the saline control. It is also lower than in the control group treated with native oxyntomodulin.

It will be appreciated that throughout the above examples, compounds of the invention are capable of inhibiting food intake at doses markedly lower than that of the native peptide used in the comparator experiments.

SEQUENCE LISTING

```
<160> NUMBER OF SEQ ID NOS: 383

<210> SEQ ID NO 1
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 1

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 2

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30
```

Lys Asn Asn Ile Ala
        35

<210> SEQ ID NO 3
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 3

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Met Asn Thr Lys Arg Asn
            20                  25                  30

Lys Asn Asn Ile Ala
        35

<210> SEQ ID NO 4
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 4

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 5
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 5

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 6
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 6

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 7
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 7

His Ser Gln Gly Thr Phe Thr Ser Asp Tyr Ser Lys Tyr Leu Glu Glu
1               5                   10                  15

Glu Leu Val Lys Tyr Phe Ile Glu Trp Leu Lys Asn Ala Gly Pro Ser
            20                  25                  30

Lys Asn Asn Ile Ala
        35

<210> SEQ ID NO 8
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 8

His Ser Gln Gly Thr Phe Thr Ser Asp Tyr Ser Lys Tyr Leu Glu Glu
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 9
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 9

His Ser Gln Gly Thr Phe Thr Ser Asp Tyr Ser Lys Tyr Leu Glu Glu
1               5                   10                  15

Glu Leu Val Lys Tyr Phe Ile Glu Trp Leu Met Asn Thr Lys Arg Asn
            20                  25                  30

Lys Asn Asn Ile Ala
        35

<210> SEQ ID NO 10
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 10

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

```
Lys Asn Asn Ile Ala
        35

<210> SEQ ID NO 11
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 11

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 12
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 12

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 13
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 13

His Ser Gln Gly Thr Phe Thr Ser Asp Tyr Ser Lys Tyr Leu Glu Glu
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 14
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 14

His Ser Gln Gly Thr Phe Thr Ser Asp Tyr Ser Lys Tyr Leu Glu Glu
1               5                   10                  15

Glu Ile Val Lys Tyr Phe Leu Glu Trp Leu Lys Asn Gly Gly Pro Ser
            20                  25                  30
```

```
Lys Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 15

His Ser Gln Gly Thr Phe Thr Ser Asp Tyr Ser Lys Tyr Leu Glu Glu
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 16
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 16

His Ser Gln Gly Thr Phe Thr Ser Asp Tyr Ser Lys Tyr Leu Glu Glu
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 17
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 17

His Ser Gln Gly Thr Phe Thr Ser Asp Tyr Ser Lys Tyr Leu Glu Glu
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 18
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 18

His Ser Gln Gly Thr Phe Thr Ser Asp Tyr Ser Lys Tyr Leu Glu Glu
1               5                   10                  15

Glu Ile Val Lys Tyr Phe Leu Gln Trp Leu Met Asn Thr Lys Arg Asn
            20                  25                  30
```

```
Lys Asn Asn Ile Ala
        35

<210> SEQ ID NO 19
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 19

His Ser Gln Gly Thr Phe Thr Ser Asp Tyr Ser Lys Tyr Leu Glu Glu
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 20
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 20

His Ser Gln Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 21
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 21

His Ser Gln Gly Thr Phe Thr Ser Asp Tyr Ser Lys Tyr Leu Glu Glu
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 22
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 22

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30
```

Lys Asn Asn Ile Ala
        35

<210> SEQ ID NO 23
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 23

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala
        35

<210> SEQ ID NO 24
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 24

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 25
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 25

His Ser Gln Gly Thr Phe Thr Ser Asp Tyr Ser Lys Tyr Leu Glu Gln
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 26
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 26

His Ser Gln Gly Thr Phe Thr Ser Asp Tyr Ser Lys Tyr Leu Glu Gln
1               5                   10                  15

Glu Leu Val Lys Tyr Phe Leu Glu Trp Leu Lys Asn Gly Gly Pro Ser
            20                  25                  30

```
Lys Asn Asn Ile Ala
        35

<210> SEQ ID NO 27
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 27

His Ser Gln Gly Thr Phe Thr Ser Asp Tyr Ser Lys Tyr Leu Glu Gln
1               5                   10                  15

Glu Leu Val Lys Tyr Phe Leu Glu Trp Leu Met Asn Thr Lys Arg Asn
            20                  25                  30

Lys Asn Asn Ile Ala
        35

<210> SEQ ID NO 28
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 28

His Ser Gln Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 29
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 29

His Ser Gln Gly Thr Phe Thr Ser Asp Tyr Ser Lys Tyr Leu Glu Gln
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 30
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 30

His Ser Gln Gly Thr Phe Thr Ser Asp Tyr Ser Lys Tyr Leu Glu Gln
1               5                   10                  15

Glu Leu Val Lys Tyr Phe Leu Gln Trp Leu Met Asn Thr Lys Arg Asn
            20                  25                  30
```

```
Lys Asn Asn Ile Ala
        35

<210> SEQ ID NO 31
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 31

His Ser Gln Gly Thr Phe Thr Ser Asp Tyr Ser Lys Tyr Leu Glu Gln
1               5                   10                  15

Glu Leu Val Lys Tyr Phe Ile Glu Trp Leu Lys Asn Ala Gly Pro Ser
            20                  25                  30

Lys Asn Asn Ile Ala
        35

<210> SEQ ID NO 32
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 32

His Ser Gln Gly Thr Phe Thr Ser Asp Tyr Ser Lys Tyr Leu Glu Gln
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 33
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 33

His Ser Gln Gly Thr Phe Thr Ser Asp Tyr Ser Lys Tyr Leu Glu Gln
1               5                   10                  15

Glu Leu Val Lys Tyr Phe Ile Glu Trp Leu Met Asn Thr Lys Arg Asn
            20                  25                  30

Lys Asn Asn Ile Ala
        35

<210> SEQ ID NO 34
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 34

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30
```

Lys Asn Asn Ile Ala
        35

<210> SEQ ID NO 35
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 35

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 36
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 36

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 37
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 37

His Ser Gln Gly Thr Phe Thr Ser Asp Tyr Ser Lys Tyr Leu Glu Gln
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 38
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 38

His Ser Gln Gly Thr Phe Thr Ser Asp Tyr Ser Lys Tyr Leu Glu Gln
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 39
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 39

His Ser Gln Gly Thr Phe Thr Ser Asp Tyr Ser Lys Tyr Leu Glu Gln
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 40
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 40

His Ser Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 41
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 41

His Ser Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 42
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 42

His Ser Gln Gly Thr Phe Thr Ser Asp Tyr Ser Lys Tyr Leu Glu Gln
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 43
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 43

His Ser Gln Gly Thr Phe Thr Ser Asp Tyr Ser Lys Tyr Leu Glu Gln
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 44
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 44

His Ser Gln Gly Thr Phe Thr Ser Asp Tyr Ser Lys Tyr Leu Glu Gln
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 45
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 45

His Ser Gln Gly Thr Phe Thr Ser Asp Tyr Ser Lys Tyr Leu Glu Gln
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 46
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 46

His Ser Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 47
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 47

His Ser Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asn Asn Ile Ala
        35

<210> SEQ ID NO 48
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 48

His Ser Gln Gly Thr Phe Thr Ser Asp Tyr Ser Lys Tyr Leu Glu Gln
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 49
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 49

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 50
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His -continued

```
<400> SEQUENCE: 50

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 51
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 51

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Met Asn Thr Lys Arg Asn
            20                  25                  30

Lys Asn Asn Ile Ala
        35

<210> SEQ ID NO 52
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 52

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 53
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 53

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Gly Gly Pro Ser
            20                  25                  30
```

Lys Asn Asn Ile Ala
        35

<210> SEQ ID NO 54
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 54

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 55
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 55

His Ser Gln Gly Thr Phe Thr Ser Asp Tyr Ser Lys Tyr Leu Glu Glu
1               5                   10                  15

Glu Leu Val Lys Tyr Phe Ile Glu Trp Leu Lys Asn Ala Gly Pro Ser
            20                  25                  30

Lys Asn Asn Ile Ala
        35

<210> SEQ ID NO 56
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 56

His Ser Gln Gly Thr Phe Thr Ser Asp Tyr Ser Lys Tyr Leu Glu Glu
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 57
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 57

His Ser Gln Gly Thr Phe Thr Ser Asp Tyr Ser Lys Tyr Leu Glu Glu
1               5                   10                  15

Glu Leu Val Lys Tyr Phe Ile Glu Trp Leu Met Asn Thr Lys Arg Asn
            20                  25                  30

Lys Asn Asn Ile Ala
            35

<210> SEQ ID NO 58
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 58

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

Lys Asn Asn Ile Ala
            35

<210> SEQ ID NO 59
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 59

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala
            35

<210> SEQ ID NO 60
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

```
<400> SEQUENCE: 60

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 61
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 61

His Ser Gln Gly Thr Phe Thr Ser Asp Tyr Ser Lys Tyr Leu Glu Glu
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 62
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 62

His Ser Gln Gly Thr Phe Thr Ser Asp Tyr Ser Lys Tyr Leu Glu Glu
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 63
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 63

His Ser Gln Gly Thr Phe Thr Ser Asp Tyr Ser Lys Tyr Leu Glu Glu
1               5                   10                  15

Glu Ile Val Lys Tyr Phe Leu Glu Trp Leu Met Asn Thr Lys Arg Asn
            20                  25                  30
```

```
Lys Asn Asn Ile Ala
        35

<210> SEQ ID NO 64
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 64

His Ser Gln Gly Thr Phe Thr Ser Asp Tyr Ser Lys Tyr Leu Glu Glu
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 65
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 65

His Ser Gln Gly Thr Phe Thr Ser Asp Tyr Ser Lys Tyr Leu Glu Glu
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 66
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 66

His Ser Gln Gly Thr Phe Thr Ser Asp Tyr Ser Lys Tyr Leu Glu Glu
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 67
<211> LENGTH: 37
<212> TYPE: PRT
```

<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 67

His Ser Gln Gly Thr Phe Thr Ser Asp Tyr Ser Lys Tyr Leu Glu Glu
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 68
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 68

His Ser Gln Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 69
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 69

His Ser Gln Gly Thr Phe Thr Ser Asp Tyr Ser Lys Tyr Leu Glu Glu
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 70
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 70

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 71
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 71

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala
        35

<210> SEQ ID NO 72
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 72

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 73
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 73

His Ser Gln Gly Thr Phe Thr Ser Asp Tyr Ser Lys Tyr Leu Glu Gln
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 74
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 74

His Ser Gln Gly Thr Phe Thr Ser Asp Tyr Ser Lys Tyr Leu Glu Gln
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 75
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 75

His Ser Gln Gly Thr Phe Thr Ser Asp Tyr Ser Lys Tyr Leu Glu Gln
1               5                   10                  15

Glu Leu Val Lys Tyr Phe Leu Glu Trp Leu Met Asn Thr Lys Arg Asn
            20                  25                  30

Lys Asn Asn Ile Ala
        35

<210> SEQ ID NO 76
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 76

His Ser Gln Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 77
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 77

His Ser Gln Gly Thr Phe Thr Ser Asp Tyr Ser Lys Tyr Leu Glu Gln
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 78
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 78

His Ser Gln Gly Thr Phe Thr Ser Asp Tyr Ser Lys Tyr Leu Glu Gln
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 79
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 79

His Ser Gln Gly Thr Phe Thr Ser Asp Tyr Ser Lys Tyr Leu Glu Gln
1               5                   10                  15

Glu Leu Val Lys Tyr Phe Ile Glu Trp Leu Lys Asn Ala Gly Pro Ser
            20                  25                  30

Lys Asn Asn Ile Ala
        35

<210> SEQ ID NO 80
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 80

His Ser Gln Gly Thr Phe Thr Ser Asp Tyr Ser Lys Tyr Leu Glu Gln
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 81
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 81

His Ser Gln Gly Thr Phe Thr Ser Asp Tyr Ser Lys Tyr Leu Glu Gln
1               5                   10                  15

Glu Leu Val Lys Tyr Phe Ile Glu Trp Leu Met Asn Thr Lys Arg Asn
            20                  25                  30

Lys Asn Asn Ile Ala
        35

<210> SEQ ID NO 82
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 82

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 83
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 83

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 84
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 84

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 85
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 85

His Ser Gln Gly Thr Phe Thr Ser Asp Tyr Ser Lys Tyr Leu Glu Gln
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 86
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 86

His Ser Gln Gly Thr Phe Thr Ser Asp Tyr Ser Lys Tyr Leu Glu Gln
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 87
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 87

His Ser Gln Gly Thr Phe Thr Ser Asp Tyr Ser Lys Tyr Leu Glu Gln
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 88
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 88

His Ser Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 89
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 89

His Ser Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 90
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 90

His Ser Gln Gly Thr Phe Thr Ser Asp Tyr Ser Lys Tyr Leu Glu Gln
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 91
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 91

His Ser Gln Gly Thr Phe Thr Ser Asp Tyr Ser Lys Tyr Leu Glu Gln
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 92
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 92

His Ser Gln Gly Thr Phe Thr Ser Asp Tyr Ser Lys Tyr Leu Glu Gln
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 93
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 93

His Ser Gln Gly Thr Phe Thr Ser Asp Tyr Ser Lys Tyr Leu Glu Gln
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 94
<211> LENGTH: 37
<212> TYPE: PRT
<213> ORGANISM: Artificial Sequence
<220> FEATURE:
<223> OTHER INFORMATION: /note="Description of Artificial Sequence:
     Synthetic peptide"
<220> FEATURE:
<221> NAME/KEY: MOD_RES
<222> LOCATION: (1)..(1)
<223> OTHER INFORMATION: D-His

<400> SEQUENCE: 94

His Ser Gln Gly Thr Phe Thr Ser Asp Tyr Ser Lys Tyr Leu Glu Gln
1             5                 10               15

Glu Ile Val Lys Tyr Phe Ile Gln Trp Leu Lys Asn Ala Gly Pro Ser
              20               25              30

Lys Asn Asn Ile Ala
        35

<210> SEQ ID NO 95
<211> LENGTH: 37
<212> TYPE: PRT
<213> ORGANISM: Artificial Sequence
<220> FEATURE:
<223> OTHER INFORMATION: /note="Description of Artificial Sequence:
     Synthetic peptide"
<220> FEATURE:
<221> NAME/KEY: MOD_RES
<222> LOCATION: (1)..(1)
<223> OTHER INFORMATION: D-His

<400> SEQUENCE: 95

His Ser Gln Gly Thr Phe Thr Ser Asp Tyr Ser Lys Tyr Leu Glu Gln
1             5                 10               15

Glu Ile Val Lys Tyr Phe Ile Gln Trp Leu Lys Asn Gly Gly Pro Ser
              20               25              30

Lys Asn Asn Ile Ala
        35

<210> SEQ ID NO 96
<211> LENGTH: 37
<212> TYPE: PRT
<213> ORGANISM: Artificial Sequence
<220> FEATURE:
<223> OTHER INFORMATION: /note="Description of Artificial Sequence:
     Synthetic peptide"
<220> FEATURE:
<221> NAME/KEY: MOD_RES
<222> LOCATION: (1)..(1)
<223> OTHER INFORMATION: D-His

<400> SEQUENCE: 96

His Ser Gln Gly Thr Phe Thr Ser Asp Tyr Ser Lys Tyr Leu Glu Gln
1             5                 10               15

Glu Ile Val Lys Tyr Phe Ile Gln Trp Leu Met Asn Thr Lys Arg Asn
              20               25              30

Lys Asn Asn Ile Ala
        35

<210> SEQ ID NO 97
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 97

His Ala Gln Gly Thr Phe Thr Ser Asp Tyr Ser Lys Tyr Leu Glu Glu
1               5                  10                  15

Glu Leu Val Lys Tyr Phe Leu Glu Trp Leu Lys Asn Ala Gly Pro Ser
            20                  25                  30

Lys Asn Asn Ile Ala
            35

<210> SEQ ID NO 98
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 98

His Ala Gln Gly Thr Phe Thr Ser Asp Tyr Ser Lys Tyr Leu Glu Glu
1               5                  10                  15

Glu Leu Val Lys Tyr Phe Leu Glu Trp Leu Lys Asn Gly Gly Pro Ser
            20                  25                  30

Lys Asn Asn Ile Ala
            35

<210> SEQ ID NO 99
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 99

His Ala Gln Gly Thr Phe Thr Ser Asp Tyr Ser Lys Tyr Leu Glu Glu
1               5                  10                  15

Glu Leu Val Lys Tyr Phe Leu Glu Trp Leu Met Asn Thr Lys Arg Asn
            20                  25                  30

Lys Asn Asn Ile Ala
            35

<210> SEQ ID NO 100
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

```
<400> SEQUENCE: 100

His Ala Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 101
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 101

His Ala Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 102
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 102

His Ala Gln Gly Thr Phe Thr Ser Asp Tyr Ser Lys Tyr Leu Glu Glu
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 103
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 103

His Ala Gln Gly Thr Phe Thr Ser Asp Tyr Ser Lys Tyr Leu Glu Glu
1               5                   10                  15

Glu Leu Val Lys Tyr Phe Ile Glu Trp Leu Lys Asn Ala Gly Pro Ser
            20                  25                  30
```

Lys Asn Asn Ile Ala
        35

<210> SEQ ID NO 104
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 104

His Ala Gln Gly Thr Phe Thr Ser Asp Tyr Ser Lys Tyr Leu Glu Glu
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 105
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 105

His Ala Gln Gly Thr Phe Thr Ser Asp Tyr Ser Lys Tyr Leu Glu Glu
1               5                   10                  15

Glu Leu Val Lys Tyr Phe Ile Glu Trp Leu Met Asn Thr Lys Arg Asn
            20                  25                  30

Lys Asn Asn Ile Ala
        35

<210> SEQ ID NO 106
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 106

His Ala Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 107
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 107

His Ala Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 108
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 108

His Ala Gln Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 109
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 109

His Ala Gln Gly Thr Phe Thr Ser Asp Tyr Ser Lys Tyr Leu Glu Glu
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 110
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 110

His Ala Gln Gly Thr Phe Thr Ser Asp Tyr Ser Lys Tyr Leu Glu Glu
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 111
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 111

His Ala Gln Gly Thr Phe Thr Ser Asp Tyr Ser Lys Tyr Leu Glu Glu
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 112
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 112

His Ala Gln Gly Thr Phe Thr Ser Asp Tyr Ser Lys Tyr Leu Glu Glu
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 113
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 113

His Ala Gln Gly Thr Phe Thr Ser Asp Tyr Ser Lys Tyr Leu Glu Glu
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 114
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 114

His Ala Gln Gly Thr Phe Thr Ser Asp Tyr Ser Lys Tyr Leu Glu Glu
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 115
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 115

His Ala Gln Gly Thr Phe Thr Ser Asp Tyr Ser Lys Tyr Leu Glu Glu
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 116
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 116

His Ala Gln Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 117
<211> LENGTH: 37
<212> TYPE: PRT

<213> ORGANISM: Artificial Sequence
<220> FEATURE:
<223> OTHER INFORMATION: /note="Description of Artificial Sequence:
       Synthetic peptide"
<220> FEATURE:
<221> NAME/KEY: MOD_RES
<222> LOCATION: (1)..(1)
<223> OTHER INFORMATION: D-His

<400> SEQUENCE: 117

His Ala Gln Gly Thr Phe Thr Ser Asp Tyr Ser Lys Tyr Leu Glu Glu
1               5                   10                  15

Glu Ile Val Lys Tyr Phe Ile Glu Trp Leu Met Asn Thr Lys Arg Asn
            20                  25                  30

Lys Asn Asn Ile Ala
            35

<210> SEQ ID NO 118
<211> LENGTH: 37
<212> TYPE: PRT
<213> ORGANISM: Artificial Sequence
<220> FEATURE:
<223> OTHER INFORMATION: /note="Description of Artificial Sequence:
       Synthetic peptide"
<220> FEATURE:
<221> NAME/KEY: MOD_RES
<222> LOCATION: (1)..(1)
<223> OTHER INFORMATION: D-His

<400> SEQUENCE: 118

His Ala Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30

Lys Asn Asn Ile Ala
            35

<210> SEQ ID NO 119
<211> LENGTH: 37
<212> TYPE: PRT
<213> ORGANISM: Artificial Sequence
<220> FEATURE:
<223> OTHER INFORMATION: /note="Description of Artificial Sequence:
       Synthetic peptide"
<220> FEATURE:
<221> NAME/KEY: MOD_RES
<222> LOCATION: (1)..(1)
<223> OTHER INFORMATION: D-His

<400> SEQUENCE: 119

His Ala Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala
            35

<210> SEQ ID NO 120
<211> LENGTH: 37
<212> TYPE: PRT
<213> ORGANISM: Artificial Sequence
<220> FEATURE:
<223> OTHER INFORMATION: /note="Description of Artificial Sequence:
       Synthetic peptide"
<220> FEATURE:
<221> NAME/KEY: MOD_RES
<222> LOCATION: (1)..(1)
<223> OTHER INFORMATION: D-His

```
<400> SEQUENCE: 120

His Ala Gln Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 121
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 121

His Ala Gln Gly Thr Phe Thr Ser Asp Tyr Ser Lys Tyr Leu Glu Gln
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 122
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 122

His Ala Gln Gly Thr Phe Thr Ser Asp Tyr Ser Lys Tyr Leu Glu Gln
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 123
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 123

His Ala Gln Gly Thr Phe Thr Ser Asp Tyr Ser Lys Tyr Leu Glu Gln
1               5                   10                  15

Glu Leu Val Lys Tyr Phe Leu Glu Trp Leu Met Asn Thr Lys Arg Asn
            20                  25                  30
```

```
Lys Asn Asn Ile Ala
        35

<210> SEQ ID NO 124
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 124

His Ala Gln Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 125
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 125

His Ala Gln Gly Thr Phe Thr Ser Asp Tyr Ser Lys Tyr Leu Glu Gln
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 126
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 126

His Ala Gln Gly Thr Phe Thr Ser Asp Tyr Ser Lys Tyr Leu Glu Gln
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 127
<211> LENGTH: 37
<212> TYPE: PRT
```

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 127

His Ala Gln Gly Thr Phe Thr Ser Asp Tyr Ser Lys Tyr Leu Glu Gln
1               5                   10                  15

Glu Leu Val Lys Tyr Phe Ile Glu Trp Leu Lys Asn Ala Gly Pro Ser
            20                  25                  30

Lys Asn Asn Ile Ala
            35

<210> SEQ ID NO 128
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 128

His Ala Gln Gly Thr Phe Thr Ser Asp Tyr Ser Lys Tyr Leu Glu Gln
1               5                   10                  15

Glu Leu Val Lys Tyr Phe Ile Glu Trp Leu Lys Asn Gly Gly Pro Ser
            20                  25                  30

Lys Asn Asn Ile Ala
            35

<210> SEQ ID NO 129
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 129

His Ala Gln Gly Thr Phe Thr Ser Asp Tyr Ser Lys Tyr Leu Glu Gln
1               5                   10                  15

Glu Leu Val Lys Tyr Phe Ile Glu Trp Leu Met Asn Thr Lys Arg Asn
            20                  25                  30

Lys Asn Asn Ile Ala
            35

<210> SEQ ID NO 130
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

```
<400> SEQUENCE: 130

His Ala Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asn Asn Ile Ala
            35

<210> SEQ ID NO 131
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 131

His Ala Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala
            35

<210> SEQ ID NO 132
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 132

His Ala Gln Gly Thr Phe Thr Ser Asp Tyr Ser Lys Tyr Leu Glu Gln
1               5                   10                  15

Glu Leu Val Lys Tyr Phe Ile Gln Trp Leu Met Asn Thr Lys Arg Asn
            20                  25                  30

Lys Asn Asn Ile Ala
            35

<210> SEQ ID NO 133
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 133

His Ala Gln Gly Thr Phe Thr Ser Asp Tyr Ser Lys Tyr Leu Glu Gln
1               5                   10                  15

Glu Ile Val Lys Tyr Phe Leu Glu Trp Leu Lys Asn Ala Gly Pro Ser
            20                  25                  30
```

Lys Asn Asn Ile Ala
        35

<210> SEQ ID NO 134
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 134

His Ala Gln Gly Thr Phe Thr Ser Asp Tyr Ser Lys Tyr Leu Glu Gln
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 135
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 135

His Ala Gln Gly Thr Phe Thr Ser Asp Tyr Ser Lys Tyr Leu Glu Gln
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 136
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 136

His Ala Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 137
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 137

His Ala Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 138
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 138

His Ala Gln Gly Thr Phe Thr Ser Asp Tyr Ser Lys Tyr Leu Glu Gln
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 139
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 139

His Ala Gln Gly Thr Phe Thr Ser Asp Tyr Ser Lys Tyr Leu Glu Gln
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 140
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

```
<400> SEQUENCE: 140

His Ala Gln Gly Thr Phe Thr Ser Asp Tyr Ser Lys Tyr Leu Glu Gln
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 141
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 141

His Ala Gln Gly Thr Phe Thr Ser Asp Tyr Ser Lys Tyr Leu Glu Gln
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 142
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 142

His Ala Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 143
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 143

His Ala Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30
```

-continued

Lys Asn Asn Ile Ala
        35

<210> SEQ ID NO 144
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 144

His Ala Gln Gly Thr Phe Thr Ser Asp Tyr Ser Lys Tyr Leu Glu Gln
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 145
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 145

His Ala Asp Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 146
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 146

His Ala Asp Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 147
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 147

His Ala Asp Gly Thr Phe Thr Ser Asp Tyr Ser Lys Tyr Leu Glu Glu
1               5                   10                  15

Glu Leu Val Lys Tyr Phe Leu Glu Trp Leu Met Asn Thr Lys Arg Asn
            20                  25                  30

Lys Asn Asn Ile Ala
        35

<210> SEQ ID NO 148
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 148

His Ala Asp Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 149
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 149

His Ala Asp Gly Thr Phe Thr Ser Asp Tyr Ser Lys Tyr Leu Glu Glu
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 150
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 150

His Ala Asp Gly Thr Phe Thr Ser Asp Tyr Ser Lys Tyr Leu Glu Glu
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 151
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 151

His Ala Asp Gly Thr Phe Thr Ser Asp Tyr Ser Lys Tyr Leu Glu Glu
1               5                   10                  15

Glu Leu Val Lys Tyr Phe Ile Glu Trp Leu Lys Asn Ala Gly Pro Ser
            20                  25                  30

Lys Asn Asn Ile Ala
        35

<210> SEQ ID NO 152
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 152

His Ala Asp Gly Thr Phe Thr Ser Asp Tyr Ser Lys Tyr Leu Glu Glu
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 153
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 153

His Ala Asp Gly Thr Phe Thr Ser Asp Tyr Ser Lys Tyr Leu Glu Glu
1               5                   10                  15

Glu Leu Val Lys Tyr Phe Ile Glu Trp Leu Met Asn Thr Lys Arg Asn
            20                  25                  30

Lys Asn Asn Ile Ala
        35

<210> SEQ ID NO 154
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 154

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 155
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 155

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 156
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 156

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 157
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 157

His Ala Asp Gly Thr Phe Thr Ser Asp Tyr Ser Lys Tyr Leu Glu Glu
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 158
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 158

His Ala Asp Gly Thr Phe Thr Ser Asp Tyr Ser Lys Tyr Leu Glu Glu
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 159
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 159

His Ala Asp Gly Thr Phe Thr Ser Asp Tyr Ser Lys Tyr Leu Glu Glu
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 160
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 160

His Ala Asp Gly Thr Phe Thr Ser Asp Tyr Ser Lys Tyr Leu Glu Glu
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 161
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 161

His Ala Asp Gly Thr Phe Thr Ser Asp Tyr Ser Lys Tyr Leu Glu Glu
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 162
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 162

His Ala Asp Gly Thr Phe Thr Ser Asp Tyr Ser Lys Tyr Leu Glu Glu
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 163
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 163

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Lys Asn Ala Gly Pro Ser
            20                  25                  30

```
Lys Asn Asn Ile Ala
        35

<210> SEQ ID NO 164
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 164

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 165
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 165

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 166
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 166

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 167
<211> LENGTH: 37
<212> TYPE: PRT
```

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 167

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala
        35

<210> SEQ ID NO 168
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 168

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 169
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 169

His Ala Asp Gly Thr Phe Thr Ser Asp Tyr Ser Lys Tyr Leu Glu Gln
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 170
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 170

His Ala Asp Gly Thr Phe Thr Ser Asp Tyr Ser Lys Tyr Leu Glu Gln
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 171
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 171

His Ala Asp Gly Thr Phe Thr Ser Asp Tyr Ser Lys Tyr Leu Glu Gln
1               5                   10                  15

Glu Leu Val Lys Tyr Phe Leu Glu Trp Leu Met Asn Thr Lys Arg Asn
            20                  25                  30

Lys Asn Asn Ile Ala
        35

<210> SEQ ID NO 172
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 172

His Ala Asp Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 173
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 173

His Ala Asp Gly Thr Phe Thr Ser Asp Tyr Ser Lys Tyr Leu Glu Gln
1               5                   10                  15

Glu Leu Val Lys Tyr Phe Leu Gln Trp Leu Lys Asn Gly Gly Pro Ser
            20                  25                  30

Lys Asn Asn Ile Ala
        35

<210> SEQ ID NO 174
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 174

His Ala Asp Gly Thr Phe Thr Ser Asp Tyr Ser Lys Tyr Leu Glu Gln
1               5                   10                  15

Glu Leu Val Lys Tyr Phe Leu Gln Trp Leu Met Asn Thr Lys Arg Asn
            20                  25                  30

Lys Asn Asn Ile Ala
        35

<210> SEQ ID NO 175
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 175

His Ala Asp Gly Thr Phe Thr Ser Asp Tyr Ser Lys Tyr Leu Glu Gln
1               5                   10                  15

Glu Leu Val Lys Tyr Phe Ile Glu Trp Leu Lys Asn Ala Gly Pro Ser
            20                  25                  30

Lys Asn Asn Ile Ala
        35

<210> SEQ ID NO 176
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 176

His Ala Asp Gly Thr Phe Thr Ser Asp Tyr Ser Lys Tyr Leu Glu Gln
1               5                   10                  15

Glu Leu Val Lys Tyr Phe Ile Glu Trp Leu Lys Asn Gly Gly Pro Ser
            20                  25                  30

Lys Asn Asn Ile Ala
        35

<210> SEQ ID NO 177
<211> LENGTH: 37
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 177

His Ala Asp Gly Thr Phe Thr Ser Asp Tyr Ser Lys Tyr Leu Glu Gln
1               5                   10                  15

Glu Leu Val Lys Tyr Phe Ile Glu Trp Leu Met Asn Thr Lys Arg Asn
            20                  25                  30

Lys Asn Asn Ile Ala
        35

<210> SEQ ID NO 178
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 178

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 179
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 179

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 180
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

<400> SEQUENCE: 180

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 181
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 181

His Ala Asp Gly Thr Phe Thr Ser Asp Tyr Ser Lys Tyr Leu Glu Gln
1               5                   10                  15

Glu Ile Val Lys Tyr Phe Leu Glu Trp Leu Lys Asn Ala Gly Pro Ser
            20                  25                  30

Lys Asn Asn Ile Ala
        35

<210> SEQ ID NO 182
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 182

His Ala Asp Gly Thr Phe Thr Ser Asp Tyr Ser Lys Tyr Leu Glu Gln
1               5                   10                  15

Glu Ile Val Lys Tyr Phe Leu Glu Trp Leu Lys Asn Gly Gly Pro Ser
            20                  25                  30

Lys Asn Asn Ile Ala
        35

<210> SEQ ID NO 183
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 183

His Ala Asp Gly Thr Phe Thr Ser Asp Tyr Ser Lys Tyr Leu Glu Gln
1               5                   10                  15

Glu Ile Val Lys Tyr Phe Leu Glu Trp Leu Met Asn Thr Lys Arg Asn
            20                  25                  30

Lys Asn Asn Ile Ala
        35

<210> SEQ ID NO 184
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 184

His Ala Asp Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 185
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 185

His Ala Asp Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 186
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 186

His Ala Asp Gly Thr Phe Thr Ser Asp Tyr Ser Lys Tyr Leu Glu Gln
1               5                   10                  15

Glu Ile Val Lys Tyr Phe Leu Gln Trp Leu Met Asn Thr Lys Arg Asn
            20                  25                  30

Lys Asn Asn Ile Ala
        35

<210> SEQ ID NO 187
<211> LENGTH: 37
<212> TYPE: PRT

<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 187

His Ala Asp Gly Thr Phe Thr Ser Asp Tyr Ser Lys Tyr Leu Glu Gln
1               5                   10                  15

Glu Ile Val Lys Tyr Phe Ile Glu Trp Leu Lys Asn Ala Gly Pro Ser
            20                  25                  30

Lys Asn Asn Ile Ala
        35

<210> SEQ ID NO 188
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 188

His Ala Asp Gly Thr Phe Thr Ser Asp Tyr Ser Lys Tyr Leu Glu Gln
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 189
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 189

His Ala Asp Gly Thr Phe Thr Ser Asp Tyr Ser Lys Tyr Leu Glu Gln
1               5                   10                  15

Glu Ile Val Lys Tyr Phe Ile Glu Trp Leu Met Asn Thr Lys Arg Asn
            20                  25                  30

Lys Asn Asn Ile Ala
        35

<210> SEQ ID NO 190
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 190

His Ala Asp Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 191
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 191

His Ala Asp Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asn Asn Ile Ala
        35

<210> SEQ ID NO 192
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 192

His Ala Asp Gly Thr Phe Thr Ser Asp Tyr Ser Lys Tyr Leu Glu Gln
1               5                   10                  15

Glu Ile Val Lys Tyr Phe Ile Gln Trp Leu Met Asn Thr Lys Arg Asn
            20                  25                  30

Lys Asn Asn Ile Ala
        35

<210> SEQ ID NO 193
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 193

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

-continued

<210> SEQ ID NO 194
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 194

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Gly Gly Pro Ser
            20                  25                  30

Lys Asn Asn Ile Ala
        35

<210> SEQ ID NO 195
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 195

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

<210> SEQ ID NO 196
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 196

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Gly Gly Pro Ser
            20                  25                  30

Lys Asn Asn Ile Ala
        35

<210> SEQ ID NO 197
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

```
<400> SEQUENCE: 197

His Ala Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

<210> SEQ ID NO 198
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 198

His Ala Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Gly Gly Pro Ser
            20                  25                  30

Lys Asn Asn Ile Ala
        35

<210> SEQ ID NO 199
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 199

His Ala Asp Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

<210> SEQ ID NO 200
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 200

His Ala Asp Gly Thr Phe Thr Ser Asp Tyr Ser Lys Tyr Leu Asp Ser
1               5                   10                  15

Arg Arg Ala Gln Asp Phe Val Gln Trp Leu Lys Asn Gly Gly Pro Ser
            20                  25                  30
```

Lys Asn Asn Ile Ala
        35

<210> SEQ ID NO 201
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 201

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 202
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 202

His Ala Asp Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 203
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 203

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asn Asn Ile Ala Lys
        35

<210> SEQ ID NO 204
<211> LENGTH: 38
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 204

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Lys
            35

<210> SEQ ID NO 205
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 205

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala Lys
            35

<210> SEQ ID NO 206
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-myristoyl

<400> SEQUENCE: 206

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
            35                  40

<210> SEQ ID NO 207
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
```

```
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-palmitoyl

<400> SEQUENCE: 207

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 208
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-stearoyl

<400> SEQUENCE: 208

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 209
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-arachidoyl

<400> SEQUENCE: 209

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 210
<211> LENGTH: 40
<212> TYPE: PRT
```

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 210

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 211
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-myristoyl

<400> SEQUENCE: 211

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 212
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-myristoyl

<400> SEQUENCE: 212

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 213
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
```

```
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-palmitoyl

<400> SEQUENCE: 213

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 214
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-arachidoyl

<400> SEQUENCE: 214

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 215
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 215

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asp Asn Ile Ala
        35

<210> SEQ ID NO 216
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

```
<220> FEATURE:
<221> NAME/KEY: MOD_RES
<222> LOCATION: (1)..(1)
<223> OTHER INFORMATION: D-His

<400> SEQUENCE: 216

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asp Asn Ile Ala
        35

<210> SEQ ID NO 217
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 217

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30

Lys Asp Asn Ile Ala
        35

<210> SEQ ID NO 218
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 218

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala
        35

<210> SEQ ID NO 219
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 219

His Ser Gln Gly Thr Phe Thr Ser Asp Tyr Ser Lys Tyr Leu Glu Glu
```

| 1 | | | | 5 | | | | | 10 | | | | | 15 | |
|---|---|---|---|---|---|---|---|---|---|---|---|---|---|---|---|

Glu Ile Val Lys Tyr Phe Ile Gln Trp Leu Lys Asn Ala Gly Pro Ser
          20              25              30

Lys Asp Asn Ile Ala
        35

<210> SEQ ID NO 220
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 220

His Ser Gln Gly Thr Phe Thr Ser Asp Tyr Ser Lys Tyr Leu Glu Glu
1             5                10              15

Glu Leu Val Lys Tyr Phe Leu Gln Trp Leu Lys Asn Ala Gly Pro Ser
          20              25              30

Lys Asp Asn Ile Ala
        35

<210> SEQ ID NO 221
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 221

His Ser Gln Gly Thr Phe Thr Ser Asp Tyr Ser Lys Tyr Leu Glu Glu
1             5                10              15

Glu Leu Val Lys Tyr Phe Ile Gln Trp Leu Lys Asn Ala Gly Pro Ser
          20              25              30

Lys Asp Asn Ile Ala
        35

<210> SEQ ID NO 222
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 222

His Ser Gln Gly Thr Phe Thr Ser Asp Tyr Ser Lys Tyr Leu Glu Glu
1             5                10              15

Glu Leu Val Lys Tyr Phe Ile Gln Trp Leu Met Asn Thr Lys Arg Asn
          20              25              30

Lys Asp Asn Ile Ala
        35

```
<210> SEQ ID NO 223
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 223

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asp Asn Ile Ala
        35

<210> SEQ ID NO 224
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 224

His Ser Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asp Asn Ile Ala
        35

<210> SEQ ID NO 225
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 225

His Ala Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala
        35

<210> SEQ ID NO 226
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

```
<220> FEATURE:
<221> NAME/KEY: MOD_RES
<222> LOCATION: (1)..(1)
<223> OTHER INFORMATION: D-His

<400> SEQUENCE: 226

His Ala Gln Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asp Asn Ile Ala
        35

<210> SEQ ID NO 227
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 227

His Ala Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asp Asn Ile Ala
        35

<210> SEQ ID NO 228
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 228

His Ala Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asp Asn Ile Ala
        35

<210> SEQ ID NO 229
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 229

His Ala Gln Gly Thr Phe Thr Ser Asp Tyr Ser Lys Tyr Leu Glu Gln
```

```
                1               5                   10                  15
Glu Ile Val Lys Tyr Phe Leu Gln Trp Leu Lys Asn Gly Gly Pro Ser
                20                  25                  30

Lys Asp Asn Ile Ala
            35

<210> SEQ ID NO 230
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 230

His Ala Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
                20                  25                  30

Lys Asp Asn Ile Ala
            35

<210> SEQ ID NO 231
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 231

His Ala Asp Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
                20                  25                  30

Lys Asp Asn Ile Ala
            35

<210> SEQ ID NO 232
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 232

His Ala Asp Gly Thr Phe Thr Ser Asp Tyr Ser Lys Tyr Leu Glu Glu
1               5                   10                  15

Glu Leu Val Lys Tyr Phe Ile Glu Trp Leu Met Asn Thr Lys Arg Asn
                20                  25                  30

Lys Asp Asn Ile Ala
            35
```

<210> SEQ ID NO 233
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 233

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala
        35

<210> SEQ ID NO 234
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 234

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asp Asn Ile Ala
        35

<210> SEQ ID NO 235
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 235

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asp Asn Ile Ala
        35

<210> SEQ ID NO 236
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

```
<220> FEATURE:
<221> NAME/KEY: MOD_RES
<222> LOCATION: (1)..(1)
<223> OTHER INFORMATION: D-His

<400> SEQUENCE: 236

His Ala Asp Gly Thr Phe Thr Ser Asp Tyr Ser Lys Tyr Leu Glu Gln
1               5                   10                  15
Glu Leu Val Lys Tyr Phe Leu Gln Trp Leu Lys Asn Ala Gly Pro Ser
            20                  25                  30
Lys Asp Asn Ile Ala
        35

<210> SEQ ID NO 237
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 237

His Ala Asp Gly Thr Phe Thr Ser Asp Tyr Ser Lys Tyr Leu Glu Gln
1               5                   10                  15
Glu Leu Val Lys Tyr Phe Ile Gln Trp Leu Lys Asn Ala Gly Pro Ser
            20                  25                  30
Lys Asp Asn Ile Ala
        35

<210> SEQ ID NO 238
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 238

His Ala Asp Gly Thr Phe Thr Ser Asp Tyr Ser Lys Tyr Leu Glu Gln
1               5                   10                  15
Glu Ile Val Lys Tyr Phe Leu Gln Trp Leu Lys Asn Ala Gly Pro Ser
            20                  25                  30
Lys Asp Asn Ile Ala
        35

<210> SEQ ID NO 239
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 239

His Ser Gln Gly Thr Phe Thr Ser Asp Tyr Ser Lys Tyr Leu Asp Ser
```

```
1               5                   10                  15
Arg Arg Ala Gln Asp Phe Val Gln Trp Leu Lys Asn Ala Gly Pro Ser
            20                  25                  30

Lys Asp Asn Ile Ala
        35

<210> SEQ ID NO 240
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 240

His Ala Asp Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asp Asn Ile Ala
        35

<210> SEQ ID NO 241
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 241

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asp Asn Ile Ala Lys
        35

<210> SEQ ID NO 242
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 242

His Ala Asp Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asp Asn Ile Ala Lys
        35
```

```
<210> SEQ ID NO 243
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 243

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asp Asn Ile Ala Lys
        35

<210> SEQ ID NO 244
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 244

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Lys
        35

<210> SEQ ID NO 245
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 245

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asp Asn Ile Ala Lys
        35

<210> SEQ ID NO 246
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
```

```
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-myristoyl

<400> SEQUENCE: 246

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
            35                  40

<210> SEQ ID NO 247
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-palmitoyl

<400> SEQUENCE: 247

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
            35                  40

<210> SEQ ID NO 248
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-stearoyl

<400> SEQUENCE: 248

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
            35                  40

<210> SEQ ID NO 249
<211> LENGTH: 40
<212> TYPE: PRT
```

<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-arachidoyl

<400> SEQUENCE: 249

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
        35                  40

<210> SEQ ID NO 250
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 250

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 251
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-myristoyl

<400> SEQUENCE: 251

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 252
<211> LENGTH: 40
<212> TYPE: PRT

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-palmitoyl

<400> SEQUENCE: 252

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 253
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-arachidoyl

<400> SEQUENCE: 253

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 254
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 254

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asp Asn Ile Ala
        35

<210> SEQ ID NO 255
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

<400> SEQUENCE: 255

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asp Asn Ile Ala
        35

<210> SEQ ID NO 256
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 256

His Ser Gln Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30

Lys Asp Asn Ile Ala
        35

<210> SEQ ID NO 257
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 257

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala
        35

<210> SEQ ID NO 258
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 258

His Ser Gln Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30

Lys Asp Asn Ile Ala
        35

<210> SEQ ID NO 259
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 259

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala
        35

<210> SEQ ID NO 260
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 260

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

Lys Asp Asn Ile Ala
        35

<210> SEQ ID NO 261
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 261

His Ser Gln Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asp Asn Ile Ala
        35

<210> SEQ ID NO 262
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 262

His Ser Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asp Asn Ile Ala
        35

<210> SEQ ID NO 263
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 263

His Ser Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asp Asn Ile Ala
        35

<210> SEQ ID NO 264
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 264

His Ala Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala
        35

<210> SEQ ID NO 265
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 265

His Ala Gln Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asp Asn Ile Ala
        35

<210> SEQ ID NO 266
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 266

His Ala Gln Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asp Asn Ile Ala
        35

<210> SEQ ID NO 267
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 267

His Ala Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asp Asn Ile Ala
            35

<210> SEQ ID NO 268
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 268

His Ala Gln Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asp Asn Ile Ala
            35

<210> SEQ ID NO 269
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 269

His Ala Gln Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asp Asn Ile Ala
            35

<210> SEQ ID NO 270
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 270

His Ala Asp Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala
            35

<210> SEQ ID NO 271
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 271

His Ala Asp Gly Thr Phe Thr Ser Asp Tyr Ser Lys Tyr Leu Glu Glu
1               5                   10                  15

Glu Leu Val Lys Tyr Phe Ile Glu Trp Leu Met Asn Thr Lys Arg Asn
            20                  25                  30

Lys Asp Asn Ile Ala
        35

<210> SEQ ID NO 272
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 272

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala
        35

<210> SEQ ID NO 273
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 273

His Ala Asp Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asp Asn Ile Ala
        35

<210> SEQ ID NO 274
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 274

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asp Asn Ile Ala
        35

<210> SEQ ID NO 275
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

```
<400> SEQUENCE: 275

His Ala Asp Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asp Asn Ile Ala
        35

<210> SEQ ID NO 276
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 276

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asp Asn Ile Ala
        35

<210> SEQ ID NO 277
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 277

His Ala Asp Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asp Asn Ile Ala
        35

<210> SEQ ID NO 278
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 278

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asp Asn Ile Ala
        35

<210> SEQ ID NO 279
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

<400> SEQUENCE: 279

His Ala Asp Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asp Asn Ile Ala
        35

<210> SEQ ID NO 280
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 280

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asp Asn Ile Ala Lys
        35

<210> SEQ ID NO 281
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 281

His Ala Asp Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asp Asn Ile Ala Lys
        35

<210> SEQ ID NO 282
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 282

His Ala Asp Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asp Asn Ile Ala Lys
        35

<210> SEQ ID NO 283
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 283

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Lys
        35

<210> SEQ ID NO 284
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 284

His Ala Asp Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asp Asn Ile Ala Lys
        35

<210> SEQ ID NO 285
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-myristoyl

<400> SEQUENCE: 285

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
        35                  40

<210> SEQ ID NO 286
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-palmitoyl

<400> SEQUENCE: 286

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
        35                  40

-continued

```
<210> SEQ ID NO 287
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-stearoyl

<400> SEQUENCE: 287

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
        35                  40

<210> SEQ ID NO 288
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-arachidoyl

<400> SEQUENCE: 288

His Ala Asp Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asp Asn Ile Ala Ala Ala Lys
        35                  40

<210> SEQ ID NO 289
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 289

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 290
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-myrostoyl
```

<400> SEQUENCE: 290

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 291
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-palmitoyl

<400> SEQUENCE: 291

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 292
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-arachidoyl

<400> SEQUENCE: 292

His Ser Gln Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asp Asn Ile Ala Glu Ala Lys
        35                  40

<210> SEQ ID NO 293
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 293

His Ala Glu Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 294
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 294

His Ser Glu Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 295
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 295

His Ser Glu Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 296
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 296

His Ser Glu Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 297
<211> LENGTH: 37
<212> TYPE: PRT

<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 297

His Ser Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 298
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 298

His Ser Glu Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 299
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 299

His Ser Glu Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 300
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

```
<400> SEQUENCE: 300

His Ser Glu Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 301
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 301

His Ala Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 302
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 302

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 303
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 303

His Ala Glu Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30
```

```
<210> SEQ ID NO 304
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 304

His Ala Glu Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 305
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 305

His Ala Glu Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 306
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 306

His Ala Glu Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 307
<211> LENGTH: 37
<212> TYPE: PRT
```

```
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 307

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala
            35

<210> SEQ ID NO 308
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 308

His Ala Glu Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asn Asn Ile Ala
            35

<210> SEQ ID NO 309
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 309

His Ser Glu Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
            35

<210> SEQ ID NO 310
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
```

```
<400> SEQUENCE: 310

His Ala Glu Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

<210> SEQ ID NO 311
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 311

His Ala Glu Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 312
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 312

His Ala Glu Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 313
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 313

His Ala Glu Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30
```

Lys Asn Asn Ile Ala Lys
        35

<210> SEQ ID NO 314
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 314

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Lys
        35

<210> SEQ ID NO 315
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 315

His Ala Glu Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala Lys
        35

<210> SEQ ID NO 316
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-myristoyl

<400> SEQUENCE: 316

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

```
<210> SEQ ID NO 317
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-palmitoyl

<400> SEQUENCE: 317

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 318
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-stearoyl

<400> SEQUENCE: 318

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 319
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-arachidoyl

<400> SEQUENCE: 319

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30
```

```
Lys Asn Asn Ile Ala Ala Ala Lys
        35                  40

<210> SEQ ID NO 320
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 320

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 321
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-myristoyl

<400> SEQUENCE: 321

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 322
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-palmitoyl

<400> SEQUENCE: 322

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30
```

```
Lys Asn Asn Ile Ala Glu Ala Lys
        35                  40

<210> SEQ ID NO 323
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His
<220> FEATURE:
<221> NAME/KEY: MOD_RES
<222> LOCATION: (40)..(40)
<223> OTHER INFORMATION: Lys-arachidoyl

<400> SEQUENCE: 323

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 324
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 324

His Ala Glu Gly Thr Phe Thr Ser Asp Tyr Ser Lys Tyr Leu Glu Glu
1               5                   10                  15

Glu Ile Val Lys Tyr Phe Ile Glu Trp Leu Lys Asn Gly Gly Pro Ser
            20                  25                  30

Lys Asn Asn Ile Ala
        35

<210> SEQ ID NO 325
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 325

His Ser Glu Gly Thr Phe Thr Ser Asp Tyr Ser Lys Tyr Leu Glu Glu
1               5                   10                  15

Glu Leu Val Lys Tyr Phe Leu Glu Trp Leu Lys Asn Ala Gly Pro Ser
            20                  25                  30

Lys Asn Asn Ile Ala
        35

<210> SEQ ID NO 326
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

```
<400> SEQUENCE: 326

His Ser Glu Gly Thr Phe Thr Ser Asp Tyr Ser Lys Tyr Leu Glu Glu
1               5                   10                  15

Glu Leu Val Lys Tyr Phe Leu Glu Trp Leu Lys Asn Gly Gly Pro Ser
            20                  25                  30

Lys Asn Asn Ile Ala
        35

<210> SEQ ID NO 327
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 327

His Ser Glu Gly Thr Phe Thr Ser Asp Tyr Ser Lys Tyr Leu Glu Glu
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 328
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 328

His Ser Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 329
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 329

His Ser Glu Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 330
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

<400> SEQUENCE: 330

His Ser Glu Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 331
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 331

His Ser Glu Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 332
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 332

His Ala Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 333
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 333

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Met Asn Thr Lys Arg Asn
            20                  25                  30

Lys Asn Asn Ile Ala
        35

<210> SEQ ID NO 334
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

-continued

```
<400> SEQUENCE: 334

His Ala Glu Gly Thr Phe Thr Ser Asp Tyr Ser Lys Tyr Leu Glu Gln
1               5                   10                  15

Glu Leu Val Lys Tyr Phe Ile Gln Trp Leu Lys Asn Ala Gly Pro Ser
            20                  25                  30

Lys Asn Asn Ile Ala
        35

<210> SEQ ID NO 335
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 335

His Ala Glu Gly Thr Phe Thr Ser Asp Tyr Ser Lys Tyr Leu Glu Gln
1               5                   10                  15

Glu Ile Val Lys Tyr Phe Leu Gln Trp Leu Lys Asn Ala Gly Pro Ser
            20                  25                  30

Lys Asn Asn Ile Ala
        35

<210> SEQ ID NO 336
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 336

His Ala Glu Gly Thr Phe Thr Ser Asp Tyr Ser Lys Tyr Leu Glu Gln
1               5                   10                  15

Glu Ile Val Lys Tyr Phe Leu Gln Trp Leu Lys Asn Gly Gly Pro Ser
            20                  25                  30

Lys Asn Asn Ile Ala
        35

<210> SEQ ID NO 337
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 337

His Ala Glu Gly Thr Phe Thr Ser Asp Tyr Ser Lys Tyr Leu Glu Gln
1               5                   10                  15

Glu Ile Val Lys Tyr Phe Ile Gln Trp Leu Lys Asn Ala Gly Pro Ser
            20                  25                  30

Lys Asn Asn Ile Ala
        35

<210> SEQ ID NO 338
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
```

-continued

```
<400> SEQUENCE: 338

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala
        35

<210> SEQ ID NO 339
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 339

His Ala Glu Gly Thr Phe Thr Ser Asp Tyr Ser Lys Tyr Leu Glu Gln
1               5                   10                  15

Glu Leu Val Lys Tyr Phe Leu Gln Trp Leu Lys Asn Ala Gly Pro Ser
            20                  25                  30

Lys Asn Asn Ile Ala
        35

<210> SEQ ID NO 340
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 340

His Ser Glu Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

<210> SEQ ID NO 341
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 341

His Ala Glu Gly Thr Phe Thr Ser Asp Tyr Ser Lys Tyr Leu Asp Ser
1               5                   10                  15

Arg Arg Ala Gln Asp Phe Val Gln Trp Leu Lys Asn Ala Gly Pro Ser
            20                  25                  30

Lys Asn Asn Ile Ala
        35

<210> SEQ ID NO 342
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
```

```
<400> SEQUENCE: 342

His Ala Glu Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 343
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 343

His Ala Glu Gly Thr Phe Thr Ser Asp Tyr Ser Lys Tyr Leu Glu Gln
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 344
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 344

His Ala Glu Gly Thr Phe Thr Ser Asp Tyr Ser Lys Tyr Leu Glu Glu
1               5                   10                  15

Glu Ile Val Lys Tyr Phe Ile Gln Trp Leu Met Asn Thr Lys Arg Asn
            20                  25                  30

Lys Asn Asn Ile Ala Lys
        35

<210> SEQ ID NO 345
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 345

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Lys
        35

<210> SEQ ID NO 346
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
```

```
<400> SEQUENCE: 346

His Ala Glu Gly Thr Phe Thr Ser Asp Tyr Ser Lys Tyr Leu Glu Gln
1               5                   10                  15

Glu Leu Val Lys Tyr Phe Ile Gln Trp Leu Lys Asn Gly Gly Pro Ser
            20                  25                  30

Lys Asn Asn Ile Ala Lys
        35

<210> SEQ ID NO 347
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-myristoyl

<400> SEQUENCE: 347

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 348
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-palmitoyl

<400> SEQUENCE: 348

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 349
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-stearoyl

<400> SEQUENCE: 349

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30
```

-continued

Lys Asn Asn Ile Ala Ala Ala Lys
        35                  40

<210> SEQ ID NO 350
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-arachidoyl

<400> SEQUENCE: 350

His Ala Glu Gly Thr Phe Thr Ser Asp Tyr Ser Lys Tyr Leu Glu Glu
1               5                   10                  15

Glu Leu Val Lys Tyr Phe Ile Gln Trp Leu Lys Asn Gly Gly Pro Ser
            20                  25                  30

Lys Asn Asn Ile Ala Ala Ala Lys
        35                  40

<210> SEQ ID NO 351
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 351

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 352
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-myristoyl

<400> SEQUENCE: 352

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 353
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"

```
<220> FEATURE:
<221> NAME/KEY: MOD_RES
<222> LOCATION: (40)..(40)
<223> OTHER INFORMATION: Lys-palmitoyl

<400> SEQUENCE: 353

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 354
<211> LENGTH: 40
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (40)..(40)
<223> OTHER INFORMATION: Lys-arachidoyl

<400> SEQUENCE: 354

His Ser Glu Gly Thr Phe Thr Ser Asp Tyr Ser Lys Tyr Leu Glu Glu
1               5                   10                  15

Glu Leu Val Lys Tyr Phe Leu Gln Trp Leu Lys Asn Ala Gly Pro Ser
            20                  25                  30

Lys Asn Asn Ile Ala Glu Ala Lys
        35                  40

<210> SEQ ID NO 355
<211> LENGTH: 38
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: D-His

<400> SEQUENCE: 355

His Ser Glu Gly Thr Phe Thr Ser Asp Tyr Ser Lys Tyr Leu Glu Glu
1               5                   10                  15

Glu Ile Val Lys Tyr Phe Ile Gln Trp Leu Lys Asn Gly Gly Pro Ser
            20                  25                  30

Lys Asn Asn Ile Ala Lys
        35

<210> SEQ ID NO 356
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: Xaa = His or D-His
<220> FEATURE:
<221> NAME/KEY: VARIANT
<222> LOCATION: (2)..(2)
<223> OTHER INFORMATION: Xaa = Ser or Ala
```

```
<220> FEATURE:
<221> NAME/KEY: VARIANT
<222> LOCATION: (3)..(3)
<223> OTHER INFORMATION: Xaa = Gln or Asp or Glu
<220> FEATURE:
<221> NAME/KEY: VARIANT
<222> LOCATION: (15)..(15)
<223> OTHER INFORMATION: Xaa = Glu or Asp
<220> FEATURE:
<221> NAME/KEY: VARIANT
<222> LOCATION: (16)..(16)
<223> OTHER INFORMATION: Xaa = Glu or Gln or Ser
<220> FEATURE:
<221> NAME/KEY: VARIANT
<222> LOCATION: (17)..(17)
<223> OTHER INFORMATION: Xaa = Glu or Arg
<220> FEATURE:
<221> NAME/KEY: VARIANT
<222> LOCATION: (18)..(18)
<223> OTHER INFORMATION: Xaa = Leu or Ile or Arg
<220> FEATURE:
<221> NAME/KEY: VARIANT
<222> LOCATION: (19)..(19)
<223> OTHER INFORMATION: Xaa = Val or Ala
<220> FEATURE:
<221> NAME/KEY: VARIANT
<222> LOCATION: (20)..(20)
<223> OTHER INFORMATION: Xaa = Lys or Gln
<220> FEATURE:
<221> NAME/KEY: VARIANT
<222> LOCATION: (21)..(21)
<223> OTHER INFORMATION: Xaa = Tyr or Asp
<220> FEATURE:
<221> NAME/KEY: VARIANT
<222> LOCATION: (23)..(23)
<223> OTHER INFORMATION: Xaa = Leu or Ile or Val
<220> FEATURE:
<221> NAME/KEY: VARIANT
<222> LOCATION: (24)..(24)
<223> OTHER INFORMATION: Xaa = Gln or Glu
<220> FEATURE:
<221> NAME/KEY: VARIANT
<222> LOCATION: (27)..(27)
<223> OTHER INFORMATION: Xaa = Lys or Met
<220> FEATURE:
<221> NAME/KEY: VARIANT
<222> LOCATION: (29)..(29)
<223> OTHER INFORMATION: Xaa = Thr or Ala or Gly
<220> FEATURE:
<221> NAME/KEY: VARIANT
<222> LOCATION: (30)..(30)
<223> OTHER INFORMATION: Xaa = Gly or Lys
<220> FEATURE:
<221> NAME/KEY: VARIANT
<222> LOCATION: (31)..(31)
<223> OTHER INFORMATION: Xaa = Pro or Arg
<220> FEATURE:
<221> NAME/KEY: VARIANT
<222> LOCATION: (32)..(32)
<223> OTHER INFORMATION: Xaa = Ser or Asn
<220> FEATURE:
<221> NAME/KEY: misc_feature
<222> LOCATION: (15)..(32)
<223> OTHER INFORMATION: /note= If Asp15 Ser16 Arg17 Arg18 Ala19 Gln20
      Asp21 Phe22 Val23 Gln24, then not Met27 Asn28 Thr29 Lys30 Arg31
      Asn32
<220> FEATURE:
<221> NAME/KEY: VARIANT
<222> LOCATION: (34)..(34)
<223> OTHER INFORMATION: Xaa = Asn or Asp

<400> SEQUENCE: 356

Xaa Xaa Xaa Gly Thr Phe Thr Ser Asp Tyr Ser Lys Tyr Leu Xaa Xaa
1               5                   10                  15

Xaa Xaa Xaa Xaa Xaa Phe Xaa Xaa Trp Leu Xaa Asn Xaa Xaa Xaa Xaa
                20                  25                  30

Lys Xaa Asn Ile Ala
```

<210> SEQ ID NO 357
<211> LENGTH: 37
<212> TYPE: PRT
<213> ORGANISM: Homo sapiens

<400> SEQUENCE: 357

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 358
<211> LENGTH: 37
<212> TYPE: PRT
<213> ORGANISM: Bos sp.

<400> SEQUENCE: 358

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Lys Asn Asn Ile Ala
        35

<210> SEQ ID NO 359
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: Xaa = His or D-His
<220> FEATURE:
<221> NAME/KEY: VARIANT
<222> LOCATION: (2)..(2)
<223> OTHER INFORMATION: Xaa = Ser or Ala
<220> FEATURE:
<221> NAME/KEY: VARIANT
<222> LOCATION: (3)..(3)
<223> OTHER INFORMATION: Xaa = Gln or Asp or Glu
<220> FEATURE:
<221> NAME/KEY: VARIANT
<222> LOCATION: (16)..(16)
<223> OTHER INFORMATION: Xaa = Glu or Gln
<220> FEATURE:
<221> NAME/KEY: VARIANT
<222> LOCATION: (18)..(18)
<223> OTHER INFORMATION: Xaa = Leu or Ile
<220> FEATURE:
<221> NAME/KEY: VARIANT
<222> LOCATION: (23)..(23)
<223> OTHER INFORMATION: Xaa = Leu or Ile
<220> FEATURE:
<221> NAME/KEY: VARIANT
<222> LOCATION: (24)..(24)
<223> OTHER INFORMATION: Xaa = Glu or Gln
<220> FEATURE:
<221> NAME/KEY: VARIANT
<222> LOCATION: (27)..(27)
<223> OTHER INFORMATION: Xaa = Lys or Met
<220> FEATURE:
<221> NAME/KEY: VARIANT
<222> LOCATION: (29)..(29)
<223> OTHER INFORMATION: Xaa = Thr or Ala or Gly

```
<220> FEATURE:
<221> NAME/KEY: VARIANT
<222> LOCATION: (30)..(30)
<223> OTHER INFORMATION: Xaa = Gly or Lys
<220> FEATURE:
<221> NAME/KEY: VARIANT
<222> LOCATION: (31)..(31)
<223> OTHER INFORMATION: Xaa = Pro or Arg
<220> FEATURE:
<221> NAME/KEY: VARIANT
<222> LOCATION: (32)..(32)
<223> OTHER INFORMATION: Xaa = Ser or Asn
<220> FEATURE:
<221> NAME/KEY: VARIANT
<222> LOCATION: (34)..(34)
<223> OTHER INFORMATION: Xaa = Asn or Asp

<400> SEQUENCE: 359

Xaa Xaa Xaa Gly Thr Phe Thr Ser Asp Tyr Ser Lys Tyr Leu Glu Xaa
1               5                   10                  15

Glu Xaa Val Lys Tyr Phe Xaa Xaa Trp Leu Xaa Asn Xaa Xaa Xaa Xaa
            20                  25                  30

Lys Xaa Asn Ile Ala
        35

<210> SEQ ID NO 360
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: Xaa = His or D-His
<220> FEATURE:
<221> NAME/KEY: VARIANT
<222> LOCATION: (2)..(2)
<223> OTHER INFORMATION: Xaa = Ser or Ala
<220> FEATURE:
<221> NAME/KEY: VARIANT
<222> LOCATION: (3)..(3)
<223> OTHER INFORMATION: Xaa = Asp or Glu
<220> FEATURE:
<221> NAME/KEY: VARIANT
<222> LOCATION: (15)..(15)
<223> OTHER INFORMATION: Xaa = Glu or Asp
<220> FEATURE:
<221> NAME/KEY: VARIANT
<222> LOCATION: (16)..(16)
<223> OTHER INFORMATION: Xaa = Glu or Gln or Ser
<220> FEATURE:
<221> NAME/KEY: VARIANT
<222> LOCATION: (17)..(17)
<223> OTHER INFORMATION: Xaa = Glu or Arg
<220> FEATURE:
<221> NAME/KEY: VARIANT
<222> LOCATION: (18)..(18)
<223> OTHER INFORMATION: Xaa = Leu or Ile or Arg
<220> FEATURE:
<221> NAME/KEY: VARIANT
<222> LOCATION: (19)..(19)
<223> OTHER INFORMATION: Xaa = Val or Ala
<220> FEATURE:
<221> NAME/KEY: VARIANT
<222> LOCATION: (20)..(20)
<223> OTHER INFORMATION: Xaa = Lys or Gln
<220> FEATURE:
<221> NAME/KEY: VARIANT
<222> LOCATION: (21)..(21)
<223> OTHER INFORMATION: Xaa = Tyr or Asp
<220> FEATURE:
<221> NAME/KEY: VARIANT
<222> LOCATION: (23)..(23)
<223> OTHER INFORMATION: Xaa = Leu or Ile or Val
```

```
<220> FEATURE:
<221> NAME/KEY: VARIANT
<222> LOCATION: (24)..(24)
<223> OTHER INFORMATION: Xaa = Gln or Glu
<220> FEATURE:
<221> NAME/KEY: VARIANT
<222> LOCATION: (27)..(27)
<223> OTHER INFORMATION: Xaa = Lys or Met
<220> FEATURE:
<221> NAME/KEY: VARIANT
<222> LOCATION: (29)..(29)
<223> OTHER INFORMATION: Xaa = Thr or Ala or Gly
<220> FEATURE:
<221> NAME/KEY: VARIANT
<222> LOCATION: (30)..(30)
<223> OTHER INFORMATION: Xaa = Gly or Lys
<220> FEATURE:
<221> NAME/KEY: VARIANT
<222> LOCATION: (31)..(31)
<223> OTHER INFORMATION: Xaa = Pro or Arg
<220> FEATURE:
<221> NAME/KEY: VARIANT
<222> LOCATION: (32)..(32)
<223> OTHER INFORMATION: Xaa = Ser or Asn
<220> FEATURE:
<221> NAME/KEY: misc_feature
<222> LOCATION: (15)..(32)
<223> OTHER INFORMATION: /note= If Asp15 Ser16 Arg17 Arg18 Ala19 Gln20
      Asp21 Phe22 Val23 Gln24 then not Met27 Asn28 Thr29 Lys30 Arg31
      Asn32
<220> FEATURE:
<221> NAME/KEY: VARIANT
<222> LOCATION: (34)..(34)
<223> OTHER INFORMATION: Xaa = Asn or Asp

<400> SEQUENCE: 360

Xaa Xaa Xaa Gly Thr Phe Thr Ser Asp Tyr Ser Lys Tyr Leu Xaa Xaa
1               5                   10                  15

Xaa Xaa Xaa Xaa Xaa Phe Xaa Xaa Trp Leu Xaa Asn Xaa Xaa Xaa Xaa
            20                  25                  30

Lys Xaa Asn Ile Ala
        35

<210> SEQ ID NO 361
<211> LENGTH: 37
<212> TYPE: PRT
<213> ORGANISM: Artificial Sequence
<220> FEATURE:
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: Xaa = His or D-His
<220> FEATURE:
<221> NAME/KEY: VARIANT
<222> LOCATION: (2)..(2)
<223> OTHER INFORMATION: Xaa = Ser or Ala
<220> FEATURE:
<221> NAME/KEY: VARIANT
<222> LOCATION: (3)..(3)
<223> OTHER INFORMATION: Xaa = Gln or Asp or Glu
<220> FEATURE:
<221> NAME/KEY: VARIANT
<222> LOCATION: (15)..(15)
<223> OTHER INFORMATION: Xaa = Glu or Asp
<220> FEATURE:
<221> NAME/KEY: VARIANT
<222> LOCATION: (16)..(16)
<223> OTHER INFORMATION: Xaa = Glu or Gln or Ser
<220> FEATURE:
<221> NAME/KEY: VARIANT
<222> LOCATION: (17)..(17)
<223> OTHER INFORMATION: Xaa = Glu or Arg
<220> FEATURE:
<221> NAME/KEY: VARIANT
```

```
<222> LOCATION: (18)..(18)
<223> OTHER INFORMATION: Xaa = Leu or Ile or Arg
<220> FEATURE:
<221> NAME/KEY: VARIANT
<222> LOCATION: (19)..(19)
<223> OTHER INFORMATION: Xaa = Val or Ala
<220> FEATURE:
<221> NAME/KEY: VARIANT
<222> LOCATION: (20)..(20)
<223> OTHER INFORMATION: Xaa = Lys or Gln
<220> FEATURE:
<221> NAME/KEY: VARIANT
<222> LOCATION: (21)..(21)
<223> OTHER INFORMATION: Xaa = Tyr or Asp
<220> FEATURE:
<221> NAME/KEY: VARIANT
<222> LOCATION: (23)..(23)
<223> OTHER INFORMATION: Xaa = Leu or Ile or Val
<220> FEATURE:
<221> NAME/KEY: VARIANT
<222> LOCATION: (24)..(24)
<223> OTHER INFORMATION: Xaa = Gln or Glu
<220> FEATURE:
<221> NAME/KEY: VARIANT
<222> LOCATION: (29)..(29)
<223> OTHER INFORMATION: Xaa = Ala or Gly
<220> FEATURE:
<221> NAME/KEY: VARIANT
<222> LOCATION: (34)..(34)
<223> OTHER INFORMATION: Xaa = Asn or Asp

<400> SEQUENCE: 361

Xaa Xaa Xaa Gly Thr Phe Thr Ser Asp Tyr Ser Lys Tyr Leu Xaa Xaa
1               5                   10                  15

Xaa Xaa Xaa Xaa Xaa Phe Xaa Xaa Trp Leu Lys Asn Xaa Gly Pro Ser
            20                  25                  30

Lys Xaa Asn Ile Ala
        35

<210> SEQ ID NO 362
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 362

Glu Glu Glu Leu Val Lys Tyr Phe Leu Glu
1               5                   10

<210> SEQ ID NO 363
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 363

Glu Glu Glu Leu Val Lys Tyr Phe Leu Gln
1               5                   10

<210> SEQ ID NO 364
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 364
```

```
Glu Glu Glu Leu Val Lys Tyr Phe Ile Glu
1               5                   10

<210> SEQ ID NO 365
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 365

Glu Glu Glu Leu Val Lys Tyr Phe Ile Gln
1               5                   10

<210> SEQ ID NO 366
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 366

Glu Glu Glu Ile Val Lys Tyr Phe Leu Glu
1               5                   10

<210> SEQ ID NO 367
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 367

Glu Glu Glu Ile Val Lys Tyr Phe Leu Gln
1               5                   10

<210> SEQ ID NO 368
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 368

Glu Glu Glu Ile Val Lys Tyr Phe Ile Glu
1               5                   10

<210> SEQ ID NO 369
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 369

Glu Glu Glu Ile Val Lys Tyr Phe Ile Gln
1               5                   10

<210> SEQ ID NO 370
<211> LENGTH: 10
<212> TYPE: PRT
<213> ORGANISM: Artificial Sequence
<220> FEATURE:
```

-continued

<223> OTHER INFORMATION: /note="Description of Artificial Sequence:
      Synthetic peptide"

<400> SEQUENCE: 370

Glu Gln Glu Leu Val Lys Tyr Phe Leu Glu
1               5                   10

<210> SEQ ID NO 371
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 371

Glu Gln Glu Leu Val Lys Tyr Phe Leu Gln
1               5                   10

<210> SEQ ID NO 372
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 372

Glu Gln Glu Leu Val Lys Tyr Phe Ile Glu
1               5                   10

<210> SEQ ID NO 373
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 373

Glu Gln Glu Leu Val Lys Tyr Phe Ile Gln
1               5                   10

<210> SEQ ID NO 374
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 374

Glu Gln Glu Ile Val Lys Tyr Phe Leu Glu
1               5                   10

<210> SEQ ID NO 375
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 375

Glu Gln Glu Ile Val Lys Tyr Phe Leu Gln
1               5                   10

<210> SEQ ID NO 376

```
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 376

Glu Gln Glu Ile Val Lys Tyr Phe Ile Glu
1               5                   10

<210> SEQ ID NO 377
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 377

Glu Gln Glu Ile Val Lys Tyr Phe Ile Gln
1               5                   10

<210> SEQ ID NO 378
<211> LENGTH: 10
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 378

Asp Ser Arg Arg Ala Gln Asp Phe Val Gln
1               5                   10

<210> SEQ ID NO 379
<211> LENGTH: 6
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 379

Met Asn Thr Lys Arg Asn
1               5

<210> SEQ ID NO 380
<211> LENGTH: 6
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 380

Lys Asn Ala Gly Pro Ser
1               5

<210> SEQ ID NO 381
<211> LENGTH: 6
<212> TYPE: PRT
<213> ORGANISM: Artificial Sequence
<220> FEATURE:
<223> OTHER INFORMATION: /note="Description of Artificial Sequence:
      Synthetic peptide"

<400> SEQUENCE: 381

Lys Asn Gly Gly Pro Ser
```

<210> SEQ ID NO 382
<211> LENGTH: 5
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 382

Asp Asp Asp Asp Tyr
1               5

<210> SEQ ID NO 383
<211> LENGTH: 5
<212> TYPE: PRT
<213> ORGANISM: Artificial Sequence
<220> FEATURE:
<223> OTHER INFORMATION: /note="Description of Artificial Sequence: Synthetic peptide"

<400> SEQUENCE: 383

His Pro Phe His Leu
1               5

The invention claimed is:

1. A peptide comprising the amino acid sequence:

(SEQ ID NO: 356)
Xaa1 Xaa2 Xaa3 Gly4 Thr5 Phe6 Thr7 Ser8 Asp9 Tyr10

Ser11 Lys12 Tyr13 Leu14 Xaa15 Xaa16 Xaa17 Xaa18

Xaa19 Xaa20 Xaa21 Xaa22 Xaa23 Xaa24 Trp25 Leu26

Xaa27 Xaa28 Xaa29 Xaa30 Xaa31 Xaa32 Lys33 Xaa34

Asn35 Ile36 Ala37;

wherein:

Xaa1 is His1 or D-His1,

Xaa2 is Ser2 or Ala2,

Xaa3 is Gln3 or Asp3;

Xaa15 Xaa16 Xaa17 Xaa18 Xaa19 Xaa20 Xaa21 Xaa22

Xaa23 Xaa24 is selected from the group consisting of:

(SEQ ID NO: 362)
Glu15 Glu16 Glu17 Leu18 Val19 Lys20 Tyr21 Phe22
Leu23 Glu24, (SEQ ID NO: 363)
Glu15 Glu16 Glu17 Leu18 Val19 Lys20 Tyr21 Phe22
Leu23 Gln24, (SEQ ID NO: 364)
Glu15 Glu16 Glu17 Leu18 Val19 Lys20 Tyr21 Phe22
Ile23 Glu24, (SEQ ID NO: 365)
Glu15 Glu16 Glu17 Leu18 Val19 Lys20 Tyr21 Phe22
Ile23 Gln24, (SEQ ID NO: 366)
Glu15 Glu16 Glu17 Ile18 Val19 Lys20 Tyr21 Phe22
Leu23 Glu24, (SEQ ID NO: 367)
Glu15 Glu16 Glu17 Ile18 Val19 Lys20 Tyr21 Phe22
Leu23 Gln24, (SEQ ID NO: 368)
Glu15 Glu16 Glu17 Ile18 Val19 Lys20 Tyr21 Phe22
Ile23 Glu24, (SEQ ID NO: 370)
Glu15 Gln16 Glu17 Leu18 Val19 Lys20 Tyr21 Phe22
Leu23 Glu24, (SEQ ID NO: 371)
Glu15 Gln16 Glu17 Leu18 Val19 Lys20 Tyr21 Phe22
Leu23 Gln24, (SEQ ID NO: 372)
Glu15 Gln16 Glu17 Leu18 Val19 Lys20 Tyr21 Phe22
Ile23 Glu24, (SEQ ID NO: 373)
Glu15 Gln16 Glu17 Leu18 Val19 Lys20 Tyr21 Phe22
Ile23 Gln24, (SEQ ID NO: 374)
Glu15 Gln16 Glu17 Ile18 Val19 Lys20 Tyr21 Phe22
Leu23 Glu24, (SEQ ID NO: 375)
Glu15 Gln16 Glu17 Ile18 Val19 Lys20 Tyr21 Phe22
Leu23 Gln24, (SEQ ID NO: 376)
Glu15 Gln16 Glu17 Ile18 Val19 Lys20 Tyr21 Phe22
Ile23 Glu24,
and (SEQ ID NO: 378)
Asp15 Ser16 Arg17 Arg18 Ala19 Gln20 Asp21 Phe22
Val23 Gln24;

Xaa27 Xaa28 Xaa29 Xaa30 Xaa31 Xaa32 is:

(SEQ ID NO: 379)
Met27 Asn28 Thr29 Lys30 Arg31 Asn32,

-continued

Lys27 Asn28 Ala29 Gly30 Pro31 Ser32, (SEQ ID NO: 380)
or

Lys27 Asn28 Gly29 Gly30 Pro31 Ser32; and (SEQ ID NO: 381)

Xaa34 is Asn34 or Asp34;

wherein the peptide optionally comprises a fusion partner;

or a peptide as set out above in which Xaa3 is Glu3;

with the proviso that if

Xaa15 Xaa16 Xaa17 Xaa18 Xaa19 Xaa20 Xaa21 Xaa22 (SEQ ID NO: 378)
Xaa23 Xaa24 is Asp15 Ser16 Arg17 Arg18 Ala19 Gln20
Asp21 Phe22 Val23 Gln24, then Xaa27 Xaa28 Xaa29 Xaa30 Xaa31 Xaa32 is not (SEQ ID NO: 379)
Met27 Asn28 Thr29 Lys30 Arg31 Asn32.

2. The peptide as claimed in claim 1, wherein
Xaa15 Xaa16 Xaa17 Xaa18 Xaa19 Xaa20 Xaa21 Xaa22
Xaa23 Xaa24 is selected from the group consisting of:

```
Glu15 Glu16 Glu17 Leu18 Val19 Lys20 Tyr21 Phe22 Leu23 Glu24,   (SEQ ID NO: 362)

Glu15 Glu16 Glu17 Leu18 Val19 Lys20 Tyr21 Phe22 Leu23 Gln24,   (SEQ ID NO: 363)

Glu15 Glu16 Glu17 Leu18 Val19 Lys20 Tyr21 Phe22 Ile23 Glu24,   (SEQ ID NO: 364)

Glu15 Glu16 Glu17 Leu18 Val19 Lys20 Tyr21 Phe22 Ile23 Glu24,   (SEQ ID NO: 365)

Glu15 Glu16 Glu17 Ile18 Val19 Lys20 Tyr21 Phe22 Leu23 Glu24,   (SEQ ID NO: 366)

Glu15 Glu16 Glu17 Ile18 Val19 Lys20 Tyr21 Phe22 Leu23 Gln24,   (SEQ ID NO: 367)

Glu15 Glu16 Glu17 Ile18 Val19 Lys20 Tyr21 Phe22 Ile23 Glu24,   (SEQ ID NO: 368)

Glu15 Gln16 Glu17 Leu18 Val19 Lys20 Tyr21 Phe22 Leu23 Glu24,   (SEQ ID NO: 370)

Glu15 Gln16 Glu17 Leu18 Val19 Lys20 Tyr21 Phe22 Leu23 Gln24,   (SEQ ID NO: 371)

Glu15 Gln16 Glu17 Leu18 Val19 Lys20 Tyr21 Phe22 Ile23 Glu24,   (SEQ ID NO: 372)

Glu15 Gln16 Glu17 Leu18 Val19 Lys20 Tyr21 Phe22 Ile23 Gln24,   (SEQ ID NO: 373)

Glu15 Gln16 Glu17 Ile18 Val19 Lys20 Tyr21 Phe22 Leu23 Glu24,   (SEQ ID NO: 374)

Glu15 Gln16 Glu17 Ile18 Val19 Lys20 Tyr21 Phe22 Leu23 Gln24,   (SEQ ID NO: 375)

Glu15 Gln16 Glu17 Ile18 Val19 Lys20 Tyr21 Phe22 Ile23 Glu24,   (SEQ ID NO: 376)
and Glu15 Gln16 Glu17 Ile18 Val19 Lys20 Tyr21 Phe22 Ile23 Gln24.   (SEQ ID NO: 377)
```

3. The peptide as claimed in claim 1, wherein Xaa1 Xaa2 Xaa3 is selected from the group consisting of His1 Ser2 Gln3, D-His1 Ser2 Gln3, D-His1 Ala2 Gln3, and D-His1 Ala2 Asp3.

4. The peptide as claimed in claim 1, wherein Xaa27 Xaa28 Xaa29 Xaa30 Xaa31 Xaa32 is selected from the group consisting of Lys27 Asn28 Ala29 Gly30 Pro31 Ser32 (SEQ ID NO:380), and Lys27 Asn28 Gly29 Gly30 Pro31 Ser32 (SEQ ID NO:381).

5. The peptide as claimed in claim 1 having an amino acid sequence selected from the group consisting of:

```
His Ser Gln Gly Thr Phe Thr Ser Asp Tyr Ser Lys Tyr Leu Glu Glu Glu Leu Val   (SEQ ID NO: 1)
Lys Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val   (SEQ ID NO: 2)
Lys Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val   (SEQ ID NO: 3)
Lys Tyr Phe Leu Glu Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Leu Val   (SEQ ID NO: 4)
Lys Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val   (SEQ ID NO: 5)
Lys Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val   (SEQ ID NO: 6)
Lys Tyr Phe Leu Gln Trp Leu Met Asn Thr Lys Arg Asn Lys Asn Asn Ile Ala
```

-continued

```
His Ser Gln Gly Thr Phe Thr Ser Asp Tyr Ser Lys Tyr Leu Glu Glu Glu Leu Val     (SEQ ID NO: 7)
Lys Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val     (SEQ ID NO: 8)
Lys Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val     (SEQ ID NO: 9)
Lys Tyr Phe Ile Glu Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Leu Val     (SEQ ID NO: 10)
Lys Tyr Phe Ile Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Leu Val     (SEQ ID NO: 11)
Lys Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Leu Val     (SEQ ID NO: 12)
Lys Tyr Phe Ile Gln Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Ile Val Lys     (SEQ ID NO: 13)
Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 14)
Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 15)
Tyr Phe Leu Glu Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Ile Val Lys     (SEQ ID NO: 16)
Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 17)
Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 18)
Tyr Phe Leu Gln Trp Leu Met Asn Thr Lys Arg Asn Lys Asn Asn Ile Ala

His Ser Gln Gly Thr Phe Thr Ser Asp Tyr Ser Lys Tyr Leu Glu Glu Glu Ile Val Lys     (SEQ ID NO: 19)
Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 20)
Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Glu Glu Ile Val Lys     (SEQ ID NO: 21)
Tyr Phe Ile Glu Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val     (SEQ ID NO: 25)
Lys Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 26)
Lys Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 27)
Lys Tyr Phe Leu Glu Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val     (SEQ ID NO: 28)
Lys Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 29)
Lys Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 30)
Lys Tyr Phe Leu Gln Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val     (SEQ ID NO: 31)
Lys Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 32)
Lys Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 33)
Lys Tyr Phe Ile Glu Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Leu Val     (SEQ ID NO: 34)
Lys Tyr Phe Ile Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 35)
Lys Tyr Phe Ile Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Leu Val     (SEQ ID NO: 36)
Lys Tyr Phe Ile Gln Trp Leu Met Asn Thr Lys Arg Asn Lys Asn Asn Ile Ala
```

-continued

```
His Ser Gln Gly Thr Phe Thr Ser Asp Tyr Ser Lys Tyr Leu Glu Gln Glu Ile Val Lys     (SEQ ID NO: 37)
Tyr Phe Leu Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 38)
Tyr Phe Leu Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 39)
Tyr Phe Leu Glu Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Ile Val Lys     (SEQ ID NO: 40)
Tyr Phe Leu Gln Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 41)
Tyr Phe Leu Gln Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 42)
Tyr Phe Leu Gln Trp Leu Met Asn Thr Lys Arg Asn Lys Asn Asn Ile Ala

His Ser Gln Gly Thr Phe Thr Ser Asp Tyr Ser Lys Tyr Leu Glu Gln Glu Ile Val Lys     (SEQ ID NO: 43)
Tyr Phe Ile Glu Trp Leu Lys Asn Ala Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 44)
Tyr Phe Ile Glu Trp Leu Lys Asn Gly Gly Pro Ser Lys Asn Asn Ile Ala

His Ser Gln Gly Thr Phe Thr Ser Asp Tyr Ser Lys Tyr Leu Glu Gln Glu Ile Val Lys     (SEQ ID NO: 45)
Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val       (SEQ ID NO: 49)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 50)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 51)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val       (SEQ ID NO: 52)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 53)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 54)
Lys Tyr Phe Leu Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val       (SEQ ID NO: 55)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 56)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 57)
Lys Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Leu Val       (SEQ ID NO: 58)
Lys Tyr Phe Ile Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 59)
Lys Tyr Phe Ile Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Leu Val       (SEQ ID NO: 60)
Lys Tyr Phe Ile Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Ile Val       (SEQ ID NO: 61)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val       (SEQ ID NO: 62)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val       (SEQ ID NO: 63)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Glu Glu Ile Val       (SEQ ID NO: 64)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val       (SEQ ID NO: 65)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val       (SEQ ID NO: 66)
Lys Tyr Phe Leu Gln Trp Leu Met Asn Thr Lys Arg Asn Lys Asn Asn Ile Ala
```

-continued

D-His Ser Gln Gly Thr Phe Thr Ser Asp Tyr Ser Lys Tyr Leu Glu Glu Glu Ile Val   (SEQ ID NO: 67)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Glu Glu Ile Val   (SEQ ID NO: 68)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Glu Glu Ile Val   (SEQ ID NO: 69)
Lys Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val   (SEQ ID NO: 73)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 74)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 75)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val   (SEQ ID NO: 76)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 77)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 78)
Lys Tyr Phe Leu Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val   (SEQ ID NO: 79)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 80)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 81)
Lys Tyr Phe Ile Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Leu Val   (SEQ ID NO: 82)
Lys Tyr Phe Ile Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 83)
Lys Tyr Phe Ile Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Leu Val   (SEQ ID NO: 84)
Lys Tyr Phe Ile Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Ile Val   (SEQ ID NO: 85)
Lys Tyr Phe Leu Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val   (SEQ ID NO: 86)
Lys Tyr Phe Leu Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val   (SEQ ID NO: 87)
Lys Tyr Phe Leu Glu Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Ile Val   (SEQ ID NO: 88)
Lys Tyr Phe Leu Gln Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val   (SEQ ID NO: 89)
Lys Tyr Phe Leu Gln Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val   (SEQ ID NO: 90)
Lys Tyr Phe Leu Gln Trp Leu Met Asn Thr Lys Arg Asn Lys Asn Asn Ile Ala

D-His Ser Gln Gly Thr Phe Thr Ser Asp Tyr Ser Lys Tyr Leu Glu Gln Glu Ile Val   (SEQ ID NO: 91)
Lys Tyr Phe Ile Glu Trp Leu Lys Asn Ala Gly Pro Ser Lys Asn Asn Ile Ala

D-His Ser Gln Gly Thr Phe Thr Ser Asp Tyr Ser Lys Tyr Leu Glu Gln Glu Ile Val   (SEQ ID NO: 92)
Lys Tyr Phe Ile Glu Trp Leu Lys Asn Gly Gly Pro Ser Lys Asn Asn Ile Ala

D-His Ser Gln Gly Thr Phe Thr Ser Asp Tyr Ser Lys Tyr Leu Glu Gln Glu Ile Val   (SEQ ID NO: 93)
Lys Tyr Phe Ile Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Glu Leu Val   (SEQ ID NO: 97)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Glu Leu Val   (SEQ ID NO: 98)
Lys Tyr Phe Leu Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Glu Leu Val   (SEQ ID NO: 99)
Lys Tyr Phe Leu Glu Trp Leu Met Asn Thr Lys Arg Asn Lys Asn Asn Ile Ala

-continued

```
D-His Ala Gln Gly Thr Phe Thr Ser Asp Tyr Ser Lys Tyr Leu Glu Glu Leu Val     (SEQ ID NO: 100)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Leu Val     (SEQ ID NO: 101)
Lys Tyr Phe Leu Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Leu Val     (SEQ ID NO: 102)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Leu Val     (SEQ ID NO: 103)
Lys Tyr Phe Ile Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Leu Val     (SEQ ID NO: 104)
Lys Tyr Phe Ile Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Leu Val     (SEQ ID NO: 105)
Lys Tyr Phe Ile Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Leu Val     (SEQ ID NO: 106)
Lys Tyr Phe Ile Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Leu Val     (SEQ ID NO: 107)
Lys Tyr Phe Ile Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Leu Val     (SEQ ID NO: 108)
Lys Tyr Phe Ile Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Ile Val     (SEQ ID NO: 109)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Ile Val     (SEQ ID NO: 110)
Lys Tyr Phe Leu Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Ile Val     (SEQ ID NO: 111)
Lys Tyr Phe Leu Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Ile Val     (SEQ ID NO: 112)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Ile Val     (SEQ ID NO: 113)
Lys Tyr Phe Leu Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Ile Val     (SEQ ID NO: 114)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Glu Ile Val     (SEQ ID NO: 115)
Lys Tyr Phe Ile Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Glu Ile Val     (SEQ ID NO: 116)
Lys Tyr Phe Ile Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Glu Ile Val     (SEQ ID NO: 117)
Lys Tyr Phe Ile Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Leu Val (SEQ ID NO: 121)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val (SEQ ID NO: 122)
Lys Tyr Phe Leu Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val (SEQ ID NO: 123)
Lys Tyr Phe Leu Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Leu Val (SEQ ID NO: 124)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val (SEQ ID NO: 125)
Lys Tyr Phe Leu Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val (SEQ ID NO: 126)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Leu Val (SEQ ID NO: 127)
Lys Tyr Phe Ile Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val (SEQ ID NO: 128)
Lys Tyr Phe Ile Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val (SEQ ID NO: 129)
Lys Tyr Phe Ile Glu Trp Leu Met Asn Thr Lys Arg Asn Lys Asn Asn Ile Ala
```

-continued

```
D-His Ala Gln Gly Thr Phe Thr Ser Asp Tyr Ser Lys Tyr Leu Glu Gln Glu Leu Val      (SEQ ID NO: 130)
Lys Tyr Phe Ile Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Leu Val      (SEQ ID NO: 131)
Lys Tyr Phe Ile Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Leu Val      (SEQ ID NO: 132)
Lys Tyr Phe Ile Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val      (SEQ ID NO: 133)
Lys Tyr Phe Leu Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val      (SEQ ID NO: 134)
Lys Tyr Phe Leu Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val      (SEQ ID NO: 135)
Lys Tyr Phe Leu Glu Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val      (SEQ ID NO: 136)
Lys Tyr Phe Leu Gln Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val      (SEQ ID NO: 137)
Lys Tyr Phe Leu Gln Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val      (SEQ ID NO: 138)
Lys Tyr Phe Leu Gln Trp Leu Met Asn Thr Lys Arg Asn Lys Asn Asn Ile Ala

D-His Ala Gln Gly Thr Phe Thr Ser Asp Tyr Ser Lys Tyr Leu Glu Gln Glu Ile Val      (SEQ ID NO: 139)
Lys Tyr Phe Ile Glu Trp Leu Lys Asn Ala Gly Pro Ser Lys Asn Asn Ile Ala

D-His Ala Gln Gly Thr Phe Thr Ser Asp Tyr Ser Lys Tyr Leu Glu Gln Glu Ile Val      (SEQ ID NO: 140)
Lys Tyr Phe Ile Glu Trp Leu Lys Asn Gly Gly Pro Ser Lys Asn Asn Ile Ala

D-His Ala Gln Gly Thr Phe Thr Ser Asp Tyr Ser Lys Tyr Leu Glu Gln Glu Ile Val      (SEQ ID NO: 141)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Leu Val      (SEQ ID NO: 145)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 146)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 147)
Lys Tyr Phe Leu Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Leu Val      (SEQ ID NO: 148)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 149)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 150)
Lys Tyr Phe Leu Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Leu Val      (SEQ ID NO: 151)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 152)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 153)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Leu Val      (SEQ ID NO: 154)
Lys Tyr Phe Ile Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 155)
Lys Tyr Phe Ile Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Leu Val      (SEQ ID NO: 156)
Lys Tyr Phe Ile Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Glu Ile Val      (SEQ ID NO: 157)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Glu Ile Val      (SEQ ID NO: 158)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Glu Ile Val      (SEQ ID NO: 159)
Lys Tyr Phe Leu Glu Trp Leu Met Asn Thr Lys Arg Asn Lys Asn Asn Ile Ala
```

```
D-His Ala Asp Gly Thr Phe Thr Ser Asp Tyr Ser Lys Tyr Leu Glu Glu Ile Val      (SEQ ID NO: 160)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Ile Val      (SEQ ID NO: 161)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Ile Val      (SEQ ID NO: 162)
Lys Tyr Phe Leu Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Glu Ile Val      (SEQ ID NO: 163)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Glu Ile Val      (SEQ ID NO: 164)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Glu Ile Val      (SEQ ID NO: 165)
Lys Tyr Phe Ile Glu Trp Leu Met Asn Thr Lys Arg Asn Lys Asn Asn Ile Ala

DD-His Ala Asp Gly Thr Phe Thr Ser Asp Tyr Ser Lys Tyr Leu Glu Gln Glu Leu Val (SEQ ID NO: 169)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 170)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 171)
Lys Tyr Phe Leu Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Leu Val  (SEQ ID NO: 172)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 173)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 174)
Lys Tyr Phe Leu Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Leu Val  (SEQ ID NO: 175)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 176)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 177)
Lys Tyr Phe Ile Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Leu Val  (SEQ ID NO: 178)
Lys Tyr Phe Ile Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 179)
Lys Tyr Phe Ile Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Leu Val  (SEQ ID NO: 180)
Lys Tyr Phe Ile Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val  (SEQ ID NO: 181)
Lys Tyr Phe Leu Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val  (SEQ ID NO: 182)
Lys Tyr Phe Leu Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val  (SEQ ID NO: 183)
Lys Tyr Phe Leu Glu Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val  (SEQ ID NO: 184)
Lys Tyr Phe Leu Gln Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val  (SEQ ID NO: 185)
Lys Tyr Phe Leu Gln Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val  (SEQ ID NO: 186)
Lys Tyr Phe Leu Gln Trp Leu Met Asn Thr Lys Arg Asn Lys Asn Asn Ile Ala

D-His Ala Asp Gly Thr Phe Thr Ser Asp Tyr Ser Lys Tyr Leu Glu Gln Glu Ile Val  (SEQ ID NO: 187)
Lys Tyr Phe Ile Glu Trp Leu Lys Asn Ala Gly Pro Ser Lys Asn Asn Ile Ala

D-His Ala Asp Gly Thr Phe Thr Ser Asp Tyr Ser Lys Tyr Leu Glu Gln Glu Ile Val  (SEQ ID NO: 188)
Lys Tyr Phe Ile Glu Trp Leu Lys Asn Gly Gly Pro Ser Lys Asn Asn Ile Ala

D-His Ala Asp Gly Thr Phe Thr Ser Asp Tyr Ser Lys Tyr Leu Glu Gln Glu Ile Val  (SEQ ID NO: 189)
Lys Tyr Phe Ile Glu Trp Leu Met Asn Thr Lys Arg Asn Lys Asn Asn Ile Ala.
```

6. The peptide as claimed in claim 1, wherein the peptide is a peptide conjugate comprising an additional extension moiety of sequence -A-B-C, wherein:
   A is absent or 1, 2, 3 or 4 Ala residues or 1, 2, 3 or 4 Glu residues
   B is absent or 1, 2, 3 or 4 Ala residues or 1, 2, 3 or 4 Glu residues
provided that A and B do not both comprise Ala residues, and that A and B do not both comprise Glu residues; and
   C is Lys, or Lys with an acid selected from capric acid, lauric acid, myristic acid, palmitic acid, stearic acid and arachidic acid, attached via its —COOH group to the —NH$_2$ group of the Lys side chain by means of a peptide bond.

7. The peptide conjugate as claimed in claim 6, wherein A or B or both A and B are absent.

8. The peptide conjugate as claimed in claim 6, wherein A is one Glu residue, and B is one Ala residue.

9. The peptide conjugate as claimed in claim 6, wherein C is a Lys residue.

10. The peptide conjugate as claimed in claim 6, wherein:
    C is a Lys residue with lauric acid attached via its —COOH group to the —NH2 group of the Lys side chain by means of a peptide bond,
    C is a Lys residue with myristic acid attached via its —COOH group to the —NH2 group of the Lys side chain by means of a peptide bond,
    C is a Lys residue with palmitic acid attached via its —COOH group to the —NH2 group of the Lys side chain by means of a peptide bond,
    C is a Lys residue with stearic acid attached via its —COOH group to the —NH2 group of the Lys side chain by means of a peptide bond,
    C is a Lys residue with arachidic acid attached via its —COOH group to the —NH2 group of the Lys side chain by means of a peptide bond,
    C is a Lys residue with capric acid attached via its —COOH group to the —NH2 group of the Lys side chain by means of a peptide bond.

11. The peptide conjugate according to claim 6 having a structure sequence selected from the group consisting of:

```
D-His Ala Asp Gly Thr Phe Thr Ser Asp Tyr Ser Lys Tyr Leu Glu Glu Glu Leu Val        (SEQ ID NO: 204)
Lys Tyr Phe Ile Gln Trp Leu Lys Asn Gly Gly Pro Ser Lys Asn Asn Ile Ala Lys

D-His Ala Asp Gly Thr Phe Thr Ser Asp Tyr Ser Lys Tyr Leu Glu Gln Glu Leu Val        (SEQ ID NO: 205)
Lys Tyr Phe Ile Gln Trp Leu Lys Asn Gly Gly Pro Ser Lys Asn Asn Ile Ala Lys

D-His Ala Asp Gly Thr Phe Thr Ser Asp Tyr Ser Lys Tyr Leu Glu Glu Glu Leu Val        (SEQ ID NO: 206)
Lys Tyr Phe Ile Gln Trp Leu Lys Asn Gly Gly Pro Ser Lys Asn Asn Ile Ala Ala Ala
Lys-myristoyl D-His Ala Asp Gly Thr Phe Thr Ser Asp Tyr Ser Lys Tyr Leu Glu Glu Glu Leu Val        (SEQ ID NO: 207)
Lys Tyr Phe Ile Gln Trp Leu Lys Asn Gly Gly Pro Ser Lys Asn Asn Ile Ala Ala Ala
Lys-palmitoyl D-His Ala Asp Gly Thr Phe Thr Ser Asp Tyr Ser Lys Tyr Leu Glu Glu Glu Leu Val        (SEQ ID NO: 208)
Lys Tyr Phe Ile Gln Trp Leu Lys Asn Gly Gly Pro Ser Lys Asn Asn Ile Ala Ala Ala
Lys-stearoyl D-His Ala Asp Gly Thr Phe Thr Ser Asp Tyr Ser Lys Tyr Leu Glu Glu Glu Leu Val        (SEQ ID NO: 209)
Lys Tyr Phe Ile Gln Trp Leu Lys Asn Gly Gly Pro Ser Lys Asn Asn Ile Ala Ala Ala
Lys-arachidoyl D-His Ser Gln Gly Thr Phe Thr Ser Asp Tyr Ser Lys Tyr Leu Glu Glu Glu Leu Val        (SEQ ID NO: 210)
Lys Tyr Phe Leu Gln Trp Leu Lys Asn Ala Gly Pro Ser Lys Asn Asn Ile Ala Glu
Ala Lys D-His Ser Gln Gly Thr Phe Thr Ser Asp Tyr Ser Lys Tyr Leu Glu Glu Glu Leu Val        (SEQ ID NO: 211)
Lys Tyr Phe Leu Gln Trp Leu Lys Asn Ala Gly Pro Ser Lys Asn Asn Ile Ala Glu
Ala Lys-myristoyl L-His Ser Gln Gly Thr Phe Thr Ser Asp Tyr Ser Lys Tyr Leu Glu Glu Glu Leu Val        (SEQ ID NO: 212)
Lys Tyr Phe Leu Gln Trp Leu Lys Asn Ala Gly Pro Ser Lys Asn Asn Ile Ala Glu
Ala Lys-myristoyl D-His Ser Gln Gly Thr Phe Thr Ser Asp Tyr Ser Lys Tyr Leu Glu Glu Glu Leu Val        (SEQ ID NO: 213)
Lys Tyr Phe Leu Gln Trp Leu Lys Asn Ala Gly Pro Ser Lys Asn Asn Ile Ala Glu
Ala Lys-palmitoyl D-His Ser Gln Gly Thr Phe Thr Ser Asp Tyr Ser Lys Tyr Leu Glu Glu Glu Leu Val        (SEQ ID NO: 214)
Lys Tyr Phe Leu Gln Trp Leu Lys Asn Ala Gly Pro Ser Lys Asn Asn Ile Ala Glu
Ala Lys-arachidoyl.
```

12. The peptide according to claim 1 having a structure sequence selected from the group consisting of:

```
D-His Ala Asp Gly Thr Phe Thr Ser Asp Tyr Ser Lys Tyr Leu Glu Glu Glu Ile Val        (SEQ ID NO: 215)
Lys Tyr Phe Ile Glu Trp Leu Lys Asn Gly Gly Pro Ser Lys Asp Asn Ile Ala

D-His Ser Gln Gly Thr Phe Thr Ser Asp Tyr Ser Lys Tyr Leu Glu Glu Glu Leu Val        (SEQ ID NO: 216)
Lys Tyr Phe Leu Glu Trp Leu Lys Asn Ala Gly Pro Ser Lys Asp Asn Ile Ala

D-His Ser Gln Gly Thr Phe Thr Ser Asp Tyr Ser Lys Tyr Leu Glu Glu Glu Leu Val        (SEQ ID NO: 217)
```

-continued

Lys Tyr Phe Leu Glu Trp Leu Lys Asn Gly Gly Pro Ser Lys Asp Asn Ile Ala

D-His Ser Gln Gly Thr Phe Thr Ser Asp Tyr Ser Lys Tyr Leu Glu Glu Glu Leu Val    (SEQ ID NO: 218)
Lys Tyr Phe Leu Gln Trp Leu Lys Asn Ala Gly Pro Ser Lys Asp Asn Ile Ala

D-His Ser Gln Gly Thr Phe Thr Ser Asp Tyr Ser Lys Tyr Leu Glu Glu Glu Leu Val    (SEQ ID NO: 220)
Lys Tyr Phe Leu Gln Trp Leu Lys Asn Ala Gly Pro Ser Lys Asp Asn Ile Ala

D-His Ser Gln Gly Thr Phe Thr Ser Asp Tyr Ser Lys Tyr Leu Glu Glu Glu Leu Val    (SEQ ID NO: 221)
Lys Tyr Phe Ile Gln Trp Leu Lys Asn Ala Gly Pro Ser Lys Asp Asn Ile Ala

D-His Ser Gln Gly Thr Phe Thr Ser Asp Tyr Ser Lys Tyr Leu Glu Glu Glu Leu Val    (SEQ ID NO: 222)
Lys Tyr Phe Ile Gln Trp Leu Met Asn Thr Lys Arg Asn Lys Asp Asn Ile Ala

D-His Ser Gln Gly Thr Phe Thr Ser Asp Tyr Ser Lys Tyr Leu Glu Gln Glu Leu Val    (SEQ ID NO: 223)
Lys Tyr Phe Ile Gln Trp Leu Lys Asn Ala Gly Pro Ser Lys Asp Asn Ile Ala

D-His Ala Gln Gly Thr Phe Thr Ser Asp Tyr Ser Lys Tyr Leu Glu Glu Glu Leu Val    (SEQ ID NO: 225)
Lys Tyr Phe Leu Gln Trp Leu Lys Asn Ala Gly Pro Ser Lys Asp Asn Ile Ala

D-His Ala Gln Gly Thr Phe Thr Ser Asp Tyr Ser Lys Tyr Leu Glu Glu Glu Leu Val    (SEQ ID NO: 226)
Lys Tyr Phe Ile Gln Trp Leu Met Asn Thr Lys Arg Asn Lys Asp Asn Ile Ala

D-His Ala Gln Gly Thr Phe Thr Ser Asp Tyr Ser Lys Tyr Leu Glu Gln Glu Leu Val    (SEQ ID NO: 227)
Lys Tyr Phe Ile Gln Trp Leu Lys Asn Ala Gly Pro Ser Lys Asp Asn Ile Ala

D-His Ala Gln Gly Thr Phe Thr Ser Asp Tyr Ser Lys Tyr Leu Glu Gln Glu Ile Val    (SEQ ID NO: 228)
Lys Tyr Phe Leu Gln Trp Leu Lys Asn Ala Gly Pro Ser Lys Asp Asn Ile Ala

D-His Ala Gln Gly Thr Phe Thr Ser Asp Tyr Ser Lys Tyr Leu Glu Gln Glu Ile Val    (SEQ ID NO: 229)
Lys Tyr Phe Leu Gln Trp Leu Lys Asn Gly Gly Pro Ser Lys Asp Asn Ile Ala

D-His Ala Asp Gly Thr Phe Thr Ser Asp Tyr Ser Lys Tyr Leu Glu Glu Glu Leu Val    (SEQ ID NO: 231)
Lys Tyr Phe Leu Gln Trp Leu Lys Asn Ala Gly Pro Ser Lys Asp Asn Ile Ala

D-His Ala Asp Gly Thr Phe Thr Ser Asp Tyr Ser Lys Tyr Leu Glu Glu Glu Leu Val    (SEQ ID NO: 232)
Lys Tyr Phe Ile Glu Trp Leu Met Asn Thr Lys Arg Asn Lys Asp Asn Ile Ala

D-His Ala Asp Gly Thr Phe Thr Ser Asp Tyr Ser Lys Tyr Leu Glu Glu Glu Leu Val    (SEQ ID NO: 233)
Lys Tyr Phe Ile Gln Trp Leu Lys Asn Gly Gly Pro Ser Lys Asp Asn Ile Ala

D-His Ala Asp Gly Thr Phe Thr Ser Asp Tyr Ser Lys Tyr Leu Glu Glu Glu Ile Val    (SEQ ID NO: 234)
Lys Tyr Phe Ile Glu Trp Leu Lys Asn Gly Gly Pro Ser Lys Asp Asn Ile Ala

D-His Ala Asp Gly Thr Phe Thr Ser Asp Tyr Ser Lys Tyr Leu Glu Gln Glu Leu Val    (SEQ ID NO: 236)
Lys Tyr Phe Leu Gln Trp Leu Lys Asn Ala Gly Pro Ser Lys Asp Asn Ile Ala

D-His Ala Asp Gly Thr Phe Thr Ser Asp Tyr Ser Lys Tyr Leu Glu Gln Glu Leu Val    (SEQ ID NO: 237)
Lys Tyr Phe Ile Gln Trp Leu Lys Asn Ala Gly Pro Ser Lys Asp Asn Ile Ala

D-His Ala Asp Gly Thr Phe Thr Ser Asp Tyr Ser Lys Tyr Leu Glu Gln Glu Ile Val    (SEQ ID NO: 238)
Lys Tyr Phe Leu Gln Trp Leu Lys Asn Ala Gly Pro Ser Lys Asp Asn Ile Ala

D-His Ser Gln Gly Thr Phe Thr Ser Asp Tyr Ser Lys Tyr Leu Asp Ser Arg Arg Ala    (SEQ ID NO: 239)
Gln Asp Phe Val Gln Trp Leu Lys Asn Ala Gly Pro Ser Lys Asp Asn Ile Ala

D-His Ala Asp Gly Thr Phe Thr Ser Asp Tyr Ser Lys Tyr Leu Asp Ser Arg Arg Ala    (SEQ ID NO: 240)
Gln Asp Phe Val Gln Trp Leu Lys Asn Ala Gly Pro Ser Lys Asp Asn Ile Ala

D-His Ala Asp Gly Thr Phe Thr Ser Asp Tyr Ser Lys Tyr Leu Glu Glu Glu Leu Val    (SEQ ID NO: 244)
Lys Tyr Phe Ile Gln Trp Leu Lys Asn Gly Gly Pro Ser Lys Asp Asn Ile Ala Lys

D-His Ala Asp Gly Thr Phe Thr Ser Asp Tyr Ser Lys Tyr Leu Glu Gln Glu Leu Val    (SEQ ID NO: 245)
Lys Tyr Phe Ile Gln Trp Leu Lys Asn Gly Gly Pro Ser Lys Asp Asn Ile Ala Lys

D-His Ala Asp Gly Thr Phe Thr Ser Asp Tyr Ser Lys Tyr Leu Glu Glu Glu Leu Val    (SEQ ID NO: 246)
Lys Tyr Phe Ile Gln Trp Leu Lys Asn Gly Gly Pro Ser Lys Asp Asn Ile Ala Ala Ala
Lys-myristoyl D-His Ala Asp Gly Thr Phe Thr Ser Asp Tyr Ser Lys Tyr Leu Glu Glu Glu Leu Val    (SEQ ID NO: 247)
Lys Tyr Phe Ile Gln Trp Leu Lys Asn Gly Gly Pro Ser Lys Asp Asn Ile Ala Ala Ala
Lys-palmitoyl D-His Ala Asp Gly Thr Phe Thr Ser Asp Tyr Ser Lys Tyr Leu Glu Glu Glu Leu Val    (SEQ ID NO: 248)
Lys Tyr Phe Ile Gln Trp Leu Lys Asn Gly Gly Pro Ser Lys Asp Asn Ile Ala Ala Ala
Lys-stearoyl D-His Ala Asp Gly Thr Phe Thr Ser Asp Tyr Ser Lys Tyr Leu Glu Glu Glu Leu Val    (SEQ ID NO: 249)
Lys Tyr Phe Ile Gln Trp Leu Lys Asn Gly Gly Pro Ser Lys Asp Asn Ile Ala Ala Ala
Lys-arachidoyl -continued D-His Ser Gln Gly Thr Phe Thr Ser Asp Tyr Ser Lys Tyr Leu Glu Glu Glu Leu Val  (SEQ ID NO: 250)
Lys Tyr Phe Leu Gln Trp Leu Lys Asn Ala Gly Pro Ser Lys Asp Asn Ile Ala Glu
Ala Lys D-His Ser Gln Gly Thr Phe Thr Ser Asp Tyr Ser Lys Tyr Leu Glu Glu Glu Leu Val  (SEQ ID NO: 251)
Lys Tyr Phe Leu Gln Trp Leu Lys Asn Ala Gly Pro Ser Lys Asp Asn Ile Ala Glu
Ala Lys-myristoyl D-His Ser Gln Gly Thr Phe Thr Ser Asp Tyr Ser Lys Tyr Leu Glu Glu Glu Leu Val  (SEQ ID NO: 252)
Lys Tyr Phe Leu Gln Trp Leu Lys Asn Ala Gly Pro Ser Lys Asp Asn Ile Ala Glu
Ala Lys-palmitoyl D-His Ser Gln Gly Thr Phe Thr Ser Asp Tyr Ser Lys Tyr Leu Glu Glu Glu Leu Val  (SEQ ID NO: 253)
Lys Tyr Phe Leu Gln Trp Leu Lys Asn Ala Gly Pro Ser Lys Asp Asn Ile Ala Glu
Ala Lys-arachidoyl L-His Ala Asp Gly Thr Phe Thr Ser Asp Tyr Ser Lys Tyr Leu Glu Glu Glu Ile Val  (SEQ ID NO: 254)
Lys Tyr Phe Ile Glu Trp Leu Lys Asn Gly Gly Pro Ser Lys Asp Asn Ile Ala L-His Ser Gln Gly Thr Phe Thr Ser Asp Tyr Ser Lys Tyr Leu Glu Glu Glu Leu Val  (SEQ ID NO: 255)
Lys Tyr Phe Leu Glu Trp Leu Lys Asn Ala Gly Pro Ser Lys Asp Asn Ile Ala L-His Ser Gln Gly Thr Phe Thr Ser Asp Tyr Ser Lys Tyr Leu Glu Glu Glu Leu Val  (SEQ ID NO: 256)
Lys Tyr Phe Leu Glu Trp Leu Lys Asn Gly Gly Pro Ser Lys Asp Asn Ile Ala L-His Ser Gln Gly Thr Phe Thr Ser Asp Tyr Ser Lys Tyr Leu Glu Glu Glu Leu Val  (SEQ ID NO: 257)
Lys Tyr Phe Leu Gln Trp Leu Lys Asn Ala Gly Pro Ser Lys Asp Asn Ile Ala L-His Ser Gln Gly Thr Phe Thr Ser Asp Tyr Ser Lys Tyr Leu Glu Glu Glu Leu Val  (SEQ ID NO: 259)
Lys Tyr Phe Leu Gln Trp Leu Lys Asn Ala Gly Pro Ser Lys Asp Asn Ile Ala L-His Ser Gln Gly Thr Phe Thr Ser Asp Tyr Ser Lys Tyr Leu Glu Glu Glu Leu Val  (SEQ ID NO: 260)
Lys Tyr Phe Ile Gln Trp Leu Lys Asn Ala Gly Pro Ser Lys Asp Asn Ile Ala L-His Ser Gln Gly Thr Phe Thr Ser Asp Tyr Ser Lys Tyr Leu Glu Glu Glu Leu Val  (SEQ ID NO: 261)
Lys Tyr Phe Ile Gln Trp Leu Met Asn Thr Lys Arg Asn Lys Asp Asn Ile Ala L-His Ser Gln Gly Thr Phe Thr Ser Asp Tyr Ser Lys Tyr Leu Glu Gln Glu Leu Val  (SEQ ID NO: 262)
Lys Tyr Phe Ile Gln Trp Leu Lys Asn Ala Gly Pro Ser Lys Asp Asn Ile Ala L-His Ala Gln Gly Thr Phe Thr Ser Asp Tyr Ser Lys Tyr Leu Glu Glu Glu Leu Val  (SEQ ID NO: 264)
Lys Tyr Phe Leu Gln Trp Leu Lys Asn Ala Gly Pro Ser Lys Asp Asn Ile Ala L-His Ala Gln Gly Thr Phe Thr Ser Asp Tyr Ser Lys Tyr Leu Glu Glu Glu Leu Val  (SEQ ID NO: 265)
Lys Tyr Phe Ile Gln Trp Leu Met Asn Thr Lys Arg Asn Lys Asp Asn Ile Ala L-His Ala Gln Gly Thr Phe Thr Ser Asp Tyr Ser Lys Tyr Leu Glu Gln Glu Leu Val  (SEQ ID NO: 266)
Lys Tyr Phe Ile Gln Trp Leu Lys Asn Ala Gly Pro Ser Lys Asp Asn Ile Ala L-His Ala Gln Gly Thr Phe Thr Ser Asp Tyr Ser Lys Tyr Leu Glu Gln Glu Ile Val  (SEQ ID NO: 267)
Lys Tyr Phe Leu Gln Trp Leu Lys Asn Ala Gly Pro Ser Lys Asp Asn Ile Ala L-His Ala Gln Gly Thr Phe Thr Ser Asp Tyr Ser Lys Tyr Leu Glu Gln Glu Ile Val  (SEQ ID NO: 268)
Lys Tyr Phe Leu Gln Trp Leu Lys Asn Gly Gly Pro Ser Lys Asp Asn Ile Ala L-His Ala Asp Gly Thr Phe Thr Ser Asp Tyr Ser Lys Tyr Leu Glu Glu Glu Leu Val  (SEQ ID NO: 270)
Lys Tyr Phe Leu Gln Trp Leu Lys Asn Ala Gly Pro Ser Lys Asp Asn Ile Ala L-His Ala Asp Gly Thr Phe Thr Ser Asp Tyr Ser Lys Tyr Leu Glu Glu Glu Leu Val  (SEQ ID NO: 271)
Lys Tyr Phe Ile Glu Trp Leu Met Asn Thr Lys Arg Asn Lys Asp Asn Ile Ala L-His Ala Asp Gly Thr Phe Thr Ser Asp Tyr Ser Lys Tyr Leu Glu Glu Glu Leu Val  (SEQ ID NO: 272)
Lys Tyr Phe Ile Gln Trp Leu Lys Asn Gly Gly Pro Ser Lys Asp Asn Ile Ala L-His Ala Asp Gly Thr Phe Thr Ser Asp Tyr Ser Lys Tyr Leu Glu Glu Glu Ile Val  (SEQ ID NO: 273)
Lys Tyr Phe Ile Glu Trp Leu Lys Asn Gly Gly Pro Ser Lys Asp Asn Ile Ala L-His Ala Asp Gly Thr Phe Thr Ser Asp Tyr Ser Lys Tyr Leu Glu Gln Glu Leu Val  (SEQ ID NO: 275)
Lys Tyr Phe Leu Gln Trp Leu Lys Asn Ala Gly Pro Ser Lys Asp Asn Ile Ala L-His Ala Asp Gly Thr Phe Thr Ser Asp Tyr Ser Lys Tyr Leu Glu Gln Glu Leu Val  (SEQ ID NO: 276)
Lys Tyr Phe Ile Gln Trp Leu Lys Asn Ala Gly Pro Ser Lys Asp Asn Ile Ala L-His Ala Asp Gly Thr Phe Thr Ser Asp Tyr Ser Lys Tyr Leu Glu Gln Glu Ile Val  (SEQ ID NO: 277)
Lys Tyr Phe Leu Gln Trp Leu Lys Asn Ala Gly Pro Ser Lys Asp Asn Ile Ala L-His Ser Gln Gly Thr Phe Thr Ser Asp Tyr Ser Lys Tyr Leu Asp Ser Arg Arg Ala  (SEQ ID NO: 278)
Gln Asp Phe Val Gln Trp Leu Lys Asn Ala Gly Pro Ser Lys Asp Asn Ile Ala L-His Ala Asp Gly Thr Phe Thr Ser Asp Tyr Ser Lys Tyr Leu Asp Ser Arg Arg Ala  (SEQ ID NO: 279)
Gln Asp Phe Val Gln Trp Leu Lys Asn Ala Gly Pro Ser Lys Asp Asn Ile Ala -continued

```
L-His Ala Asp Gly Thr Phe Thr Ser Asp Tyr Ser Lys Tyr Leu Glu Glu Glu Leu Val        (SEQ ID NO: 283)
Lys Tyr Phe Ile Gln Trp Leu Lys Asn Gly Gly Pro Ser Lys Asp Asn Ile Ala Lys

L-His Ala Asp Gly Thr Phe Thr Ser Asp Tyr Ser Lys Tyr Leu Glu Gln Glu Leu Val        (SEQ ID NO: 284)
Lys Tyr Phe Ile Gln Trp Leu Lys Asn Gly Gly Pro Ser Lys Asp Asn Ile Ala Lys

L-His Ala Asp Gly Thr Phe Thr Ser Asp Tyr Ser Lys Tyr Leu Glu Glu Glu Leu Val        (SEQ ID NO: 285)
Lys Tyr Phe Ile Gln Trp Leu Lys Asn Gly Gly Pro Ser Lys Asp Asn Ile Ala Ala Ala
Lys-myristoyl L-His Ala Asp Gly Thr Phe Thr Ser Asp Tyr Ser Lys Tyr Leu Glu Glu Glu Leu Val        (SEQ ID NO: 286)
Lys Tyr Phe Ile Gln Trp Leu Lys Asn Gly Gly Pro Ser Lys Asp Asn Ile Ala Ala Ala
Lys-palmitoyl L-His Ala Asp Gly Thr Phe Thr Ser Asp Tyr Ser Lys Tyr Leu Glu Glu Glu Leu Val        (SEQ ID NO: 287)
Lys Tyr Phe Ile Gln Trp Leu Lys Asn Gly Gly Pro Ser Lys Asp Asn Ile Ala Ala Ala
Lys-stearoyl L-His Ala Asp Gly Thr Phe Thr Ser Asp Tyr Ser Lys Tyr Leu Glu Glu Glu Leu Val        (SEQ ID NO: 288)
Lys Tyr Phe Ile Gln Trp Leu Lys Asn Gly Gly Pro Ser Lys Asp Asn Ile Ala Ala Ala
Lys-arachidoyl L-His Ser Gln Gly Thr Phe Thr Ser Asp Tyr Ser Lys Tyr Leu Glu Glu Glu Leu Val        (SEQ ID NO: 289)
Lys Tyr Phe Leu Gln Trp Leu Lys Asn Ala Gly Pro Ser Lys Asp Asn Ile Ala Glu
Ala Lys L-His Ser Gln Gly Thr Phe Thr Ser Asp Tyr Ser Lys Tyr Leu Glu Glu Glu Leu Val        (SEQ ID NO: 290)
Lys Tyr Phe Leu Gln Trp Leu Lys Asn Ala Gly Pro Ser Lys Asp Asn Ile Ala Glu
Ala Lys-myristoyl L-His Ser Gln Gly Thr Phe Thr Ser Asp Tyr Ser Lys Tyr Leu Glu Glu Glu Leu Val        (SEQ ID NO: 291)
Lys Tyr Phe Leu Gln Trp Leu Lys Asn Ala Gly Pro Ser Lys Asp Asn Ile Ala Glu
Ala Lys-palmitoyl
and L-His Ser Gln Gly Thr Phe Thr Ser Asp Tyr Ser Lys Tyr Leu Glu Glu Glu Leu Val        (SEQ ID NO: 292)
Lys Tyr Phe Leu Gln Trp Leu Lys Asn Ala Gly Pro Ser Lys Asp Asn Ile Ala Glu
Ala Lys-arachidoyl.
```

13. The peptide according to claim 1 having a structure sequence selected from the group comprising:

```
D-His Ala Glu Gly Thr Phe Thr Ser Asp Tyr Ser Lys Tyr Leu Glu Glu Glu Ile Val        (SEQ ID NO: 293)
Lys Tyr Phe Ile Glu Trp Leu Lys Asn Gly Gly Pro Ser Lys Asn Asn Ile Ala

D-His Ser Glu Gly Thr Phe Thr Ser Asp Tyr Ser Lys Tyr Leu Glu Glu Glu Leu Val        (SEQ ID NO: 294)
Lys Tyr Phe Leu Glu Trp Leu Lys Asn Ala Gly Pro Ser Lys Asn Asn Ile Ala

D-His Ser Glu Gly Thr Phe Thr Ser Asp Tyr Ser Lys Tyr Leu Glu Glu Glu Leu Val        (SEQ ID NO: 295)
Lys Tyr Phe Leu Glu Trp Leu Lys Asn Gly Gly Pro Ser Lys Asn Asn Ile Ala

D-His Ser Glu Gly Thr Phe Thr Ser Asp Tyr Ser Lys Tyr Leu Glu Glu Glu Leu Val        (SEQ ID NO: 297)
Lys Tyr Phe Ile Gln Trp Leu Lys Asn Ala Gly Pro Ser Lys Asn Asn Ile Ala

D-His Ser Glu Gly Thr Phe Thr Ser Asp Tyr Ser Lys Tyr Leu Glu Glu Glu Leu Val        (SEQ ID NO: 298)
Lys Tyr Phe Ile Gln Trp Leu Met Asn Thr Lys Arg Asn Lys Asn Asn Ile Ala

D-His Ser Glu Gly Thr Phe Thr Ser Asp Tyr Ser Lys Tyr Leu Glu Gln Glu Leu Val        (SEQ ID NO: 299)
Lys Tyr Phe Ile Gln Trp Leu Lys Asn Ala Gly Pro Ser Lys Asn Asn Ile Ala

D-His Ala Glu Gly Thr Phe Thr Ser Asp Tyr Ser Lys Tyr Leu Glu Glu Glu Leu Val        (SEQ ID NO: 301)
Lys Tyr Phe Leu Gln Trp Leu Lys Asn Ala Gly Pro Ser Lys Asn Asn Ile Ala

D-His Ala Glu Gly Thr Phe Thr Ser Asp Tyr Ser Lys Tyr Leu Glu Glu Glu Leu Val        (SEQ ID NO: 302)
Lys Tyr Phe Ile Gln Trp Leu Met Asn Thr Lys Arg Asn Lys Asn Asn Ile Ala

D-His Ala Glu Gly Thr Phe Thr Ser Asp Tyr Ser Lys Tyr Leu Glu Gln Glu Leu Val        (SEQ ID NO: 303)
Lys Tyr Phe Ile Gln Trp Leu Lys Asn Ala Gly Pro Ser Lys Asn Asn Ile Ala

D-His Ala Glu Gly Thr Phe Thr Ser Asp Tyr Ser Lys Tyr Leu Glu Gln Glu Ile Val        (SEQ ID NO: 304)
Lys Tyr Phe Leu Gln Trp Leu Lys Asn Ala Gly Pro Ser Lys Asn Asn Ile Ala

D-His Ala Glu Gly Thr Phe Thr Ser Asp Tyr Ser Lys Tyr Leu Glu Gln Glu Ile Val        (SEQ ID NO: 305)
Lys Tyr Phe Leu Gln Trp Leu Lys Asn Gly Gly Pro Ser Lys Asn Asn Ile Ala

D-His Ala Glu Gly Thr Phe Thr Ser Asp Tyr Ser Lys Tyr Leu Glu Glu Glu Leu Val        (SEQ ID NO: 307)
Lys Tyr Phe Ile Gln Trp Leu Lys Asn Gly Gly Pro Ser Lys Asn Asn Ile Ala
```

-continued

D-His Ala Glu Gly Thr Phe Thr Ser Asp Tyr Ser Lys Tyr Leu Glu Gln Glu Leu Val     (SEQ ID NO: 308)
Lys Tyr Phe Leu Gln Trp Leu Lys Asn Ala Gly Pro Ser Lys Asn Asn Ile Ala

D-His Ser Glu Gly Thr Phe Thr Ser Asp Tyr Ser Lys Tyr Leu Asp Ser Arg Arg Ala     (SEQ ID NO: 309)
Gln Asp Phe Val Gln Trp Leu Lys Asn Ala Gly Pro Ser Lys Asn Asn Ile Ala

D-His Ala Glu Gly Thr Phe Thr Ser Asp Tyr Ser Lys Tyr Leu Asp Ser Arg Arg Ala     (SEQ ID NO: 310)
Gln Asp Phe Val Gln Trp Leu Lys Asn Ala Gly Pro Ser Lys Asn Asn Ile Ala

D-His Ala Glu Gly Thr Phe Thr Ser Asp Tyr Ser Lys Tyr Leu Glu Glu Glu Leu Val     (SEQ ID NO: 314)
Lys Tyr Phe Ile Gln Trp Leu Lys Asn Gly Gly Pro Ser Lys Asn Asn Ile Ala Lys

D-His Ala Glu Gly Thr Phe Thr Ser Asp Tyr Ser Lys Tyr Leu Glu Gln Glu Leu Val     (SEQ ID NO: 315)
Lys Tyr Phe Ile Gln Trp Leu Lys Asn Gly Gly Pro Ser Lys Asn Asn Ile Ala Lys

D-His Ala Glu Gly Thr Phe Thr Ser Asp Tyr Ser Lys Tyr Leu Glu Glu Glu Leu Val     (SEQ ID NO: 316)
Lys Tyr Phe Ile Gln Trp Leu Lys Asn Gly Gly Pro Ser Lys Asn Asn Ile Ala Ala Ala
Lys-myristoyl D-His Ala Glu Gly Thr Phe Thr Ser Asp Tyr Ser Lys Tyr Leu Glu Glu Glu Leu Val     (SEQ ID NO: 317)
Lys Tyr Phe Ile Gln Trp Leu Lys Asn Gly Gly Pro Ser Lys Asn Asn Ile Ala Ala Ala
Lys-palmitoyl D-His Ala Glu Gly Thr Phe Thr Ser Asp Tyr Ser Lys Tyr Leu Glu Glu Glu Leu Val     (SEQ ID NO: 318)
Lys Tyr Phe Ile Gln Trp Leu Lys Asn Gly Gly Pro Ser Lys Asn Asn Ile Ala Ala Ala
Lys-stearoyl D-His Ala Glu Gly Thr Phe Thr Ser Asp Tyr Ser Lys Tyr Leu Glu Glu Glu Leu Val     (SEQ ID NO: 319)
Lys Tyr Phe Ile Gln Trp Leu Lys Asn Gly Gly Pro Ser Lys Asn Asn Ile Ala Ala Ala
Lys-arachidoyl D-His Ser Glu Gly Thr Phe Thr Ser Asp Tyr Ser Lys Tyr Leu Glu Glu Glu Leu Val     (SEQ ID NO: 320)
Lys Tyr Phe Leu Gln Trp Leu Lys Asn Ala Gly Pro Ser Lys Asn Asn Ile Ala Glu
Ala Lys D-His Ser Glu Gly Thr Phe Thr Ser Asp Tyr Ser Lys Tyr Leu Glu Glu Glu Leu Val     (SEQ ID NO: 321)
Lys Tyr Phe Leu Gln Trp Leu Lys Asn Ala Gly Pro Ser Lys Asn Asn Ile Ala Glu
Ala Lys-myristoyl D-His Ser Glu Gly Thr Phe Thr Ser Asp Tyr Ser Lys Tyr Leu Glu Glu Glu Leu Val     (SEQ ID NO: 322)
Lys Tyr Phe Leu Gln Trp Leu Lys Asn Ala Gly Pro Ser Lys Asn Asn Ile Ala Glu
Ala Lys-palmitoyl D-His Ser Glu Gly Thr Phe Thr Ser Asp Tyr Ser Lys Tyr Leu Glu Glu Glu Leu Val     (SEQ ID NO: 323)
Lys Tyr Phe Leu Gln Trp Leu Lys Asn Ala Gly Pro Ser Lys Asn Asn Ile Ala Glu
Ala Lys-arachidoyl L-His Ala Glu Gly Thr Phe Thr Ser Asp Tyr Ser Lys Tyr Leu Glu Glu Glu Ile Val     (SEQ ID NO: 324)
Lys Tyr Phe Ile Glu Trp Leu Lys Asn Gly Gly Pro Ser Lys Asn Asn Ile Ala L-His Ser Glu Gly Thr Phe Thr Ser Asp Tyr Ser Lys Tyr Leu Glu Glu Glu Leu Val     (SEQ ID NO: 325)
Lys Tyr Phe Leu Glu Trp Leu Lys Asn Ala Gly Pro Ser Lys Asn Asn Ile Ala L-His Ser Glu Gly Thr Phe Thr Ser Asp Tyr Ser Lys Tyr Leu Glu Glu Glu Leu Val     (SEQ ID NO: 326)
Lys Tyr Phe Leu Glu Trp Leu Lys Asn Gly Gly Pro Ser Lys Asn Asn Ile Ala L-His Ser Glu Gly Thr Phe Thr Ser Asp Tyr Ser Lys Tyr Leu Glu Glu Glu Leu Val     (SEQ ID NO: 328)
Lys Tyr Phe Ile Gln Trp Leu Lys Asn Ala Gly Pro Ser Lys Asn Asn Ile Ala L-His Ser Glu Gly Thr Phe Thr Ser Asp Tyr Ser Lys Tyr Leu Glu Glu Glu Leu Val     (SEQ ID NO: 329)
Lys Tyr Phe Ile Gln Trp Leu Met Asn Thr Lys Arg Asn Lys Asn Ile Ala L-His Ser Glu Gly Thr Phe Thr Ser Asp Tyr Ser Lys Tyr Leu Glu Gln Glu Leu Val     (SEQ ID NO: 330)
Lys Tyr Phe Ile Gln Trp Leu Lys Asn Ala Gly Pro Ser Lys Asn Asn Ile Ala L-His Ala Glu Gly Thr Phe Thr Ser Asp Tyr Ser Lys Tyr Leu Glu Glu Glu Leu Val     (SEQ ID NO: 332)
Lys Tyr Phe Leu Gln Trp Leu Lys Asn Ala Gly Pro Ser Lys Asn Asn Ile Ala L-His Ala Glu Gly Thr Phe Thr Ser Asp Tyr Ser Lys Tyr Leu Glu Glu Glu Leu Val     (SEQ ID NO: 333)
Lys Tyr Phe Ile Gln Trp Leu Met Asn Thr Lys Arg Asn Lys Asn Asn Ile Ala L-His Ala Glu Gly Thr Phe Thr Ser Asp Tyr Ser Lys Tyr Leu Glu Gln Glu Leu Val     (SEQ ID NO: 334)
Lys Tyr Phe Ile Gln Trp Leu Lys Asn Ala Gly Pro Ser Lys Asn Asn Ile Ala L-His Ala Glu Gly Thr Phe Thr Ser Asp Tyr Ser Lys Tyr Leu Glu Gln Glu Ile Val     (SEQ ID NO: 335)
Lys Tyr Phe Leu Gln Trp Leu Lys Asn Ala Gly Pro Ser Lys Asn Asn Ile Ala L-His Ala Glu Gly Thr Phe Thr Ser Asp Tyr Ser Lys Tyr Leu Glu Gln Glu Ile Val     (SEQ ID NO: 336)
Lys Tyr Phe Leu Gln Trp Leu Lys Asn Gly Gly Pro Ser Lys Asn Asn Ile Ala

```
L-His Ala Glu Gly Thr Phe Thr Ser Asp Tyr Ser Lys Tyr Leu Glu Glu Glu Leu Val      (SEQ ID NO: 338)
Lys Tyr Phe Ile Gln Trp Leu Lys Asn Gly Gly Pro Ser Lys Asn Asn Ile Ala

L-His Ala Glu Gly Thr Phe Thr Ser Asp Tyr Ser Lys Tyr Leu Glu Gln Glu Leu Val      (SEQ ID NO: 339)
Lys Tyr Phe Leu Gln Trp Leu Lys Asn Ala Gly Pro Ser Lys Asn Asn Ile Ala

L-His Ser Glu Gly Thr Phe Thr Ser Asp Tyr Ser Lys Tyr Leu Asp Ser Arg Arg Ala      (SEQ ID NO: 340)
Gln Asp Phe Val Gln Trp Leu Lys Asn Ala Gly Pro Ser Lys Asn Asn Ile Ala

L-His Ala Glu Gly Thr Phe Thr Ser Asp Tyr Ser Lys Tyr Leu Asp Ser Arg Arg Ala      (SEQ ID NO: 341)
Gln Asp Phe Val Gln Trp Leu Lys Asn Ala Gly Pro Ser Lys Asn Asn Ile Ala

L-His Ala Glu Gly Thr Phe Thr Ser Asp Tyr Ser Lys Tyr Leu Glu Glu Glu Leu Val      (SEQ ID NO: 345)
Lys Tyr Phe Ile Gln Trp Leu Lys Asn Gly Gly Pro Ser Lys Asn Asn Ile Ala Lys

L-His Ala Glu Gly Thr Phe Thr Ser Asp Tyr Ser Lys Tyr Leu Glu Gln Glu Leu Val      (SEQ ID NO: 346)
Lys Tyr Phe Ile Gln Trp Leu Lys Asn Gly Gly Pro Ser Lys Asn Asn Ile Ala Lys

L-His Ala Glu Gly Thr Phe Thr Ser Asp Tyr Ser Lys Tyr Leu Glu Glu Glu Leu Val
Lys Tyr Phe Ile Gln Trp Leu Lys Asn Gly Gly Pro Ser Lys Asn Asn Ile Ala Ala Ala   (SEQ ID NO: 347)
Lys-myristoyl L-His Ala Glu Gly Thr Phe Thr Ser Asp Tyr Ser Lys Tyr Leu Glu Glu Glu Leu Val      (SEQ ID NO: 348)
Lys Tyr Phe Ile Gln Trp Leu Lys Asn Gly Gly Pro Ser Lys Asn Asn Ile Ala Ala Ala
Lys-palmitoyl L-His Ala Glu Gly Thr Phe Thr Ser Asp Tyr Ser Lys Tyr Leu Glu Glu Glu Leu Val      (SEQ ID NO: 349)
Lys Tyr Phe Ile Gln Trp Leu Lys Asn Gly Gly Pro Ser Lys Asn Asn Ile Ala Ala Ala
Lys-stearoyl L-His Ala Glu Gly Thr Phe Thr Ser Asp Tyr Ser Lys Tyr Leu Glu Glu Glu Leu Val      (SEQ ID NO: 350)
Lys Tyr Phe Ile Gln Trp Leu Lys Asn Gly Gly Pro Ser Lys Asn Asn Ile Ala Ala Ala
Lys-arachidoyl L-His Ser Glu Gly Thr Phe Thr Ser Asp Tyr Ser Lys Tyr Leu Glu Glu Glu Leu Val      (SEQ ID NO: 351)
Lys Tyr Phe Leu Gln Trp Leu Lys Asn Ala Gly Pro Ser Lys Asn Asn Ile Ala Glu
Ala Lys L-His Ser Glu Gly Thr Phe Thr Ser Asp Tyr Ser Lys Tyr Leu Glu Glu Glu Leu Val      (SEQ ID NO: 352)
Lys Tyr Phe Leu Gln Trp Leu Lys Asn Ala Gly Pro Ser Lys Asn Asn Ile Ala Glu
Ala Lys-myristoyl L-His Ser Glu Gly Thr Phe Thr Ser Asp Tyr Ser Lys Tyr Leu Glu Glu Glu Leu Val      (SEQ ID NO: 353)
Lys Tyr Phe Leu Gln Trp Leu Lys Asn Ala Gly Pro Ser Lys Asn Asn Ile Ala Glu
Ala Lys-palmitoyl
and L-His Ser Glu Gly Thr Phe Thr Ser Asp Tyr Ser Lys Tyr Leu Glu Glu Glu Leu Val      (SEQ ID NO: 354)
Lys Tyr Phe Leu Gln Trp Leu Lys Asn Ala Gly Pro Ser Lys Asn Asn Ile Ala Glu
Ala Lys-arachidoyl.
```

14. A pharmaceutical composition comprising a peptide as claimed in claim 1 and one or more pharmaceutically acceptable carriers.

15. The pharmaceutical composition as claimed in claim 14 which is for peripheral administration.

16. The pharmaceutical composition as claimed in claim 14 which is for administration subcutaneously, intravenously, intramuscularly, intranasally, transdermally, transmucosally, orally, bucally, sublingually or via the lungs.

17. A method of treating obesity in a subject in need thereof comprising administering to the subject a peptide according to claim 1.

18. A method of reducing appetite in a subject in need thereof comprising administering to the subject a peptide according to claim 1.

19. The method as claimed in claim 18, wherein the subject is overweight.

20. The method as claimed in claim 18, wherein the subject is obese.

21. The method as claimed in claim 18, wherein the subject is diabetic.

22. The method of claim 17, wherein the peptide is administered peripherally.

23. The method of claim 17, wherein the peptide is administered subcutaneously, intravenously, intramuscularly, intranasally, transdermally, transmucosally, orally, bucally, sublingually or via the lungs.

24. The method of any one of claims 20 to 21, wherein the peptide is administered peripherally.

25. The method of any one of claims 20 to 21, wherein the peptide is administered subcutaneously, intravenously, intramuscularly, intranasally, transdermally, transmucosally, orally, bucally, sublingually or via the lungs.

26. The peptide of claim 1, further comprising a fusion partner.

27. The peptide of claim 26, wherein the fusion partner is an antibody or fragment thereof.

28. A pharmaceutical composition comprising a peptide as claimed in claim 5 and one or more pharmaceutically acceptable carriers.

29. A method of treating obesity or reducing appetite in a subject in need thereof, comprising administering to the subject a peptide according to claim 5.

30. The method of claim 29, wherein the subject is overweight.

31. The method of claim 29, wherein the subject is obese.
32. The method of claim 29, wherein the subject is diabetic.
33. The method of claim 29, wherein the peptide is administered peripherally.
34. The peptide as claimed in claim 1 having an amino acid sequence selected from the group consisting of:

```
                                       (SEQ ID NO: 60)
D-His Ser Gln Gly Thr Phe Thr Ser Asp Tyr Ser

Lys Tyr Leu Glu Glu Glu Leu Val Lys Tyr Phe

Ile Gln Trp Leu Met Asn Thr Lys Arg Asn Lys

Asn Asn Ile Ala (SEQ ID NO: 100)
D-His Ala Gln Gly Thr Phe Thr Ser Asp Tyr Ser

Lys Tyr Leu Glu Glu Glu Leu Val Lys Tyr Phe

Leu Gln Trp Leu Lys Asn Ala Gly Pro Ser Lys

Asn Asn Ile Ala (SEQ ID NO: 130)
D-His Ala Gln Gly Thr Phe Thr Ser Asp Tyr Ser

Lys Tyr Leu Glu Gln Glu Leu Val Lys Tyr Phe

Ile Gln Trp Leu Lys Asn Ala Gly Pro Ser Lys

Asn Asn Ile Ala (SEQ ID NO: 148)
D-His Ala Asp Gly Thr Phe Thr Ser Asp Tyr Ser

Lys Tyr Leu Glu Glu Glu Leu Val Lys Tyr Phe

Leu Gln Trp Leu Lys Asn Ala Gly Pro Ser Lys

Asn Asn Ile Ala (SEQ ID NO: 155)
D-His Ala Asp Gly Thr Phe Thr Ser Asp Tyr Ser

Lys Tyr Leu Glu Glu Glu Leu Val Lys Tyr Phe

Ile Gln Trp Leu Lys Asn Gly Gly Pro Ser Lys

Asn Asn Ile Ala.
```

35. The peptide of claim 34, wherein the peptide comprises a fusion partner, which is an antibody or fragment thereof.
36. A pharmaceutical composition comprising a peptide as claimed in claim 34 and one or more pharmaceutically acceptable carriers.
37. A method of treating obesity or reducing appetite in a subject in need thereof, comprising administering to the subject a peptide according to claim 34.
38. The method of claim 37, wherein the subject is overweight.
39. The method of claim 37, wherein the subject is obese.
40. The method of claim 37, wherein the subject is diabetic.
41. The method of claim 37, wherein the peptide is administered peripherally.

* * * * *